(12) United States Patent
Reithofer et al.

(10) Patent No.: US 10,117,946 B2
(45) Date of Patent: Nov. 6, 2018

(54) SELF-ASSEMBLING ULTRASHORT PEPTIDES MODIFIED WITH BIOACTIVE AGENTS BY CLICK CHEMISTRY

(71) Applicant: Agency for Science, Technology and Research, Singapore (SG)

(72) Inventors: Michael R. Reithofer, Singapore (SG); Charlotte A. E. Hauser, Singapore (SG); Kiat Hwa Chan, Singapore (SG); Archana Mishra, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/655,223

(22) PCT Filed: Dec. 24, 2013

(86) PCT No.: PCT/SG2013/000549
§ 371 (c)(1),
(2) Date: Jun. 24, 2015

(87) PCT Pub. No.: WO2014/104974
PCT Pub. Date: Jul. 3, 2014

(65) Prior Publication Data
US 2015/0352220 A1 Dec. 10, 2015

(30) Foreign Application Priority Data
Dec. 24, 2012 (SG) ................. 201209527-9

(51) Int. Cl.
| | | |
|---|---|---|
| *A01N 55/02* | (2006.01) | |
| *A61K 31/28* | (2006.01) | |
| *A61K 47/48* | (2006.01) | |
| *A61K 31/282* | (2006.01) | |
| *A61K 38/08* | (2006.01) | |
| *A61K 31/555* | (2006.01) | |

(52) U.S. Cl.
CPC ...... *A61K 47/48246* (2013.01); *A61K 31/282* (2013.01); *A61K 31/555* (2013.01); *A61K 38/08* (2013.01)

(58) Field of Classification Search
CPC .... A61K 31/282; A61K 31/555; A61K 38/08; A61K 47/48246
See application file for complete search history.

(56) References Cited

U.S. PATENT DOCUMENTS

2010/0240594 A1* 9/2010 Pellecchia ............... C07K 7/08
514/19.3

FOREIGN PATENT DOCUMENTS

| WO | WO 2003/006043 A1 | 1/2003 | |
|---|---|---|---|
| WO | WO 2008/134761 A2 | 11/2008 | |
| WO | WO 2011123061 A1 * | 10/2011 | ............. A61K 8/042 |
| WO | WO 2014/104974 A2 | 7/2014 | |

OTHER PUBLICATIONS

Wenska et al. "An activated triple bond linker enables 'click' attachment of peptides to oligonucleotides on solid support" Nucleic Acids Research, 2011, 1-13. Published Jul. 27, 2011.*
Mukhopadhyay et al. "Conjugated Platinum(IV)-Peptide Complexes for Targeting Angiogenic Tumor Vasculature" Bioconjugate Chemistry 19:39-49. Published Jan. 2008.*
Loo et al. "From short peptides to nanofibers to macromolecular assemblies in biomedicine" Biotechnology Advances 30:593-603. (Year: 2011).*
International Search Report and Written Opinion for PCT/SG2013/000549 dated Feb. 26, 2014.
International Preliminary Report on Patentability for PCT/SG2013/000549 dated Jun. 2, 2016.
Dirks et al., Synthesis and aggregation behavior of biohybrid amphiphiles composed of a tripeptidic head group and a polystyrene tail. Soft Matter. Apr. 2009;5(8):1692-1704.

* cited by examiner

*Primary Examiner* — Christina Bradley
*Assistant Examiner* — Zachary J Miknis
(74) *Attorney, Agent, or Firm* — Wolf, Greenfield & Sacks, P.C.

(57) ABSTRACT

The present invention relates to hydrogels comprising a first peptide with a covalently linked bioactive agent and optionally a second peptide. The present invention further relates to uses of the hydrogel for delivery of the bioactive agent or as an implant. The present invention further relates to drug delivery devices, implant, pharmaceutical or cosmetic compositions comprising the hydrogel. The present invention further relates to methods of local treatment of diseases and to methods for preparing the first peptide and the hydrogels.

33 Claims, 16 Drawing Sheets
Specification includes a Sequence Listing.

SELF-ASSEMBLING ULTRASHORT PEPTIDES MODIFIED WITH BIOACTIVE AGENTS BY CLICK CHEMISTRY

RELATED APPLICATIONS

This application is a U.S. National Stage application under 35 U.S.C. § 371 based on International Application No. PCT/SG2013/000549, filed Dec. 24, 2013, which claims priority to Singapore Patent Application No. 201209527-9, filed Dec. 24, 2012, each of which is incorporated by reference herein in its entirety.

FIELD OF THE INVENTION

The present invention relates to hydrogels comprising a first peptide with a covalently linked bioactive agent and optionally a second peptide. The present invention further relates to uses of the hydrogel for delivery of the bioactive agent or as an implant. The present invention further relates to drug delivery devices, implant, pharmaceutical or cosmetic compositions comprising the hydrogel. The present invention further relates to methods of local treatment of diseases and to methods for preparing the first peptide and the hydrogels.

BACKGROUND OF THE INVENTION

Self-assembly is an elegant and expedient "bottom-up" approach towards designing ordered, three-dimensional and biocompatible nanobiomaterials. Reproducible macromolecular nanostructures can be obtained due to the highly specific interactions between the building blocks. These intermolecular associations organize the supramolecular architecture and are mainly non-covalent electrostatic interactions, hydrogen bonds, van der Waals forces, etc. Supramolecular chemistry or biology gathers a vast body of two or three dimensional complex structures and entities formed by association of chemical or biological species. These associations are governed by the principles of molecular complementarity or molecular recognition and self-assembly. The knowledge of the rules of intermolecular association can be used to design polymolecular assemblies in form of membranes, films, layers, micelles, tubules, gels for a variety of biomedical or technological applications (J.-M. Lehn, Science, 295, 2400-2403, 2002).

Peptides are versatile building blocks for fabricating supramolecular architectures. Their ability to adopt specific secondary structures, as prescribed by amino acid sequence, provides a unique platform for the design of self-assembling biomaterials with hierarchical three-dimensional (3D) macromolecular architectures, nanoscale features and tuneable physical properties (S. Zhang, Nature Biotechnology, 21, 1171-1178, 2003). Peptides are for instance able to assemble into nanotubes (U.S. Pat. No. 7,179,784) or into supramolecular hydrogels consisting of three dimensional scaffolds with a large amount of around 98-99% immobilized water or aqueous solution. The peptide-based biomaterials are powerful tools for potential applications in biotechnology, medicine and even technical applications. Depending on the individual properties these peptide-based hydrogels are thought to serve in the development of new materials for tissue engineering, regenerative medicine, as drug and vaccine delivery vehicles or as peptide chips for pharmaceutical research and diagnosis (E. Place et al., Nature Materials, 8, 457-470, 2009). There is also a strong interest to use peptide-based self-assembled biomaterial such as gels for the development of molecular electronic devices (A. R. Hirst et al. Angew. Chem. Int. Ed., 47, 8002-8018, 2008).

A variety of "smart peptide hydrogels" have been generated that react on external manipulations such as temperature, pH, mechanical influences or other stimuli with a dynamic behavior of swelling, shrinking or decomposing. Nevertheless, these biomaterials are still not "advanced" enough to mimic the biological variability of natural tissues as for example the extracellular matrix (ECM) or cartilage tissue or others. The challenge for a meaningful use of peptide hydrogels is to mimic the replacing natural tissues not only as "space filler" or mechanical scaffold, but to understand and cope with the biochemical signals and physiological requirements that keep the containing cells in the right place and under "in vivo" conditions (R. Fairman and K. Akerfeldt, Current Opinion in Structural Biology, 15, 453-463, 2005).

Much effort has been undertaken to understand and control the relationship between peptide sequence and structure for a rational design of suitable hydrogels. In general hydrogels contain macroscopic structures such as fibers that entangle and form meshes. Most of the peptide-based hydrogels utilize β-pleated sheets which assemble to fibers as building blocks (S. Zhang et al., PNAS, 90, 3334-3338, 1993; A. Aggeli et al., Nature, 386, 259-262, 1997, etc.). It is also possible to obtain self-assembled hydrogels from α-helical peptides besides β-sheet structure-based materials (W. A. Petka et al., Science, 281, 389-392, 1998; C. Wang et al., Nature, 397, 417-420, 1999; C. Gribbon et al., Biochemistry, 47, 10365-10371, 2008; E. Banwell et al., Nature Materials, 8, 596-600, 2009, etc.).

The inventors have previously described ultra-short short peptide sequences (3-7 residues) capable of self-assembly into helical fibers that ultimately result in hydrogel formation. These hydrogels show remarkable properties with regards to mechanical stiffness, elasticity and biocompatibility and we demonstrated its wide application as biomimetic material (see e.g. WO 2011/123061 A1; C. A. E. Hauser, R. Deng, A. Mishra, Y. Loo, U. Khoe, F. Zhuang, D. W. Cheong, A. Accardo, M. B. Sullivan, C. Riekel, J. Y. Ying, U. A. Hauser, Proceedings of the National Academy of Sciences 2011, 108, 1361-1366; A. Mishra, Y. Loo, R. Deng, Y. J. Chuah, H. T. Hee, J. Y. Ying, C. A. E. Hauser, Nano Today 2011, 6, 232-239.).

Platinum based anticancer therapeutics are one of the most widely used in clinics today for the treatment of different types of cancers. So far, three platinum(II) compounds have been approved by the FDA, namely cisplatin, carboplatin and oxaliplatin (J. Graham, M. Muhsin, P. Kirkpatrick, Nat Rev Drug Discov 2004, 3, 11-12; L. Kelland, Nat Rev Cancer 2007, 7, 573-584; B. Rosenberg, L. Van Camp, T. Krigas, Nature 1965, 205, 698-699; B. Rosenberg, L. Vancamp, J. E. Trosko, V. H. Mansour, Nature 1969, 222, 385-386.) These drugs are widely used against a number of solid tumours including prostate, breast, colorectal, non-small-cell lung, and genitourinary cancers (L. Kelland, Nat Rev Cancer 2007, 7, 573-584; A. Horwich, J. Shipley, R. Huddart, The Lancet, 367, 754-765; H. M. Keys, B. N. Bundy, F. B. Stehman, L. I. Muderspach, W. E. Chafe, C. L. Suggs, J. L. Walker, D. Gersell, New England Journal of Medicine 1999, 340, 1154-1161.) The drugs are administered intravenously, whereby only a small amount of the given dosage can reach the target (D. Wang, S. J. Lippard, Nat Rev Drug Discov 2005, 4, 307-320.), the majority of the drug gets excreted and can cause severe side effects ranging from nausea and ototoxicity to nephrotoxicity and neurotoxicity (P. J. O'Dwyer, J. P. Stevenson, S. W. Johnson,

*Drugs* 2000, 59, 19-27.). Reducing side effects and enhancing drug uptake and efficacy is currently one of the great challenges in medicinal chemistry, especially in the development of anti-cancer therapeutics (M. Galanski, B. K. Keppler, *Anti-Cancer Agents in Medicinal Chemistry (Formerly Current Medicinal Chemistry—Anti-Cancer Agents)* 2007, 7, 55-73.)

Localized treatment is routinely used in clinic for a number of malignancies. For example, high-grade malignant glioma is treated by placing carmustine-containing synthetic copolymer wafers (Gliadel Wafer) at the site of tumor resection (H. Brem, S. Piantadosi, P. C. Burger, M. Walker, R. Selker, N. A. Vick, K. Black, M. Sisti, S. Brem, G. Mohr, P. Muller, R. Morawetz, S. C. Schold, *The Lancet* 1995, 345, 1008-1012; M. Westphal, Z. Ram, V. Riddle, D. Hilt, E. Bortey, *Acta Neurochir (Wien)* 2006, 148, 269-275; discussion 275.). Also, irinotecan-loaded drug-eluting beads injected into the hepatic artery have shown a significant improvement in a phase III study for treatment of hepatic metastases from colorectal cancer in comparison to intravenous therapy (G. Fiorentini, C. Aliberti, M. Tilli, L. Mulazzani, F. Graziano, P. Giordani, A. Mambrini, F. Montagnani, P. Alessandroni, V. Catalano, P. Cosciera, *Anticancer Research* 2012, 32, 1387-1395.).

A number of hydrogel-based delivery systems are currently in development for localized treatment. Such systems include poly(organophosphazane) polymers (A. M. Al-Abd, K.-Y. Hong, S.-C. Song, H.-J. Kuh, *Journal of Controlled Release* 2010, 142, 101-107.), PLGA-PEG-PLGA (PLGA, polylactide-co-glycolice acid) triblock compolymers (G. Chang, T. Ci, L. Yu, J. Ding, *Journal of Controlled Release* 2011, 156, 21-27.), poly(ester-carbonate)-composites (J. B. Wolinsky, R. Liu, J. Walpole, L. R. Chirieac, Y. L. Colson, M. W. Grinstaff, *Journal of Controlled Release* 2010, 144, 280-287.) and self-assembling silk hydrogels (F. P. Seib, E. M. Pritchard, D. L. Kaplan, *Advanced Functional Materials* 2012, n/a-n/a.). A major drawback of many synthetic polymeric hydrogels is the requirement of a crosslinking step that necessitates the use of potentially harmful agents such as organic solvents or chemical initiators. The residual presence of such agents decreases the biocompatibility of the hydrogels. On the other hand, UV-crosslinked polymers are often incompatible with many anticancer drugs (e.g. doxorubicin, daunorubicin, cyclophosphamide).

There is a need in the art for improved means and methods for delivery of bioactive agents and moieties, which are particularly suitable for the localized treatment of diseases, such as cancer, and/or for the controlled release of the bioactive agents.

SUMMARY OF THE INVENTION

The objects of the present invention are solved by a hydrogel comprising a first peptide having the general formula $$B^*\text{-}Z_p\text{-}(X)_m\text{-}(Y)_n\text{-}Z'_q \text{ or } Z_p\text{-}(X)_m\text{-}(Y)_n\text{-}Z'_q\text{-}B^* \text{ or } B^*\text{-}Z_p\text{-}(X)_m\text{-}(Y)_n\text{-}Z'_q\text{-}B^*$$

wherein
- B* is a bioactive agent;
- X is, at each occurrence, independently selected from an aliphatic amino acid, an aliphatic amino acid derivative and a glycine;
- Y is, at each occurrence, independently selected from a polar amino acid and a polar amino acid derivative;
- Z is an N-terminal protecting group;
- Z' is a C-terminal protecting group;
- m is an integer selected from 2 to 6;
- n is selected from 1 or 2; and
- p and q are independently selected from 0 or 1, wherein, preferably, p is 0, wherein said bioactive agent is covalently linked to the N-terminus and/or the C-terminus of said first peptide by means of a click chemistry reaction.

The objects of the present invention are solved by the use of a hydrogel of the present invention for delivery of said bioactive agent, preferably for sustained or controlled release delivery of said bioactive agent.

The objects of the present invention are solved by the use of a hydrogel of the present invention as an implant.

The objects of the present invention are solved by a device for drug delivery, preferably sustained or controlled release drug delivery, comprising a hydrogel of the present invention.

The objects of the present invention are solved by an implant comprising a hydrogel of the present invention.

The objects of the present invention are solved by a pharmaceutical or cosmetic composition comprising a hydrogel of the present invention.

The objects of the present invention are solved by a method of local treatment of a disease, said method comprising the steps of
- providing a hydrogel the present invention at a place in a body where treatment is intended; and
- allowing said hydrogel to release said bioactive agent.

The objects of the present invention are solved by a kit comprising a first container with a first peptide as defined in the present invention and a second container with an aqueous solution.

The objects of the present invention are solved by a method of preparing a first peptide of the present invention, said method comprising the steps of
- providing a peptide having the general formula $Z_p\text{-}(X)_m\text{-}(Y)_n\text{-}Z'_q$, preferably $(X)_m\text{-}(Y)_n\text{-}Z'_q$;
- functionalizing the N-terminus and/or the C-terminus of said peptide with a first functional group;
- reacting said peptide comprising said first functional group at its N-terminus and/or C-terminus with a moiety comprising said bioactive agent and a second functional group under conditions suitable for forming said first peptide, wherein said first functional group is selected from the group consisting of an alkyne group, a cyclooctyne group, an alkene group and a maleimide group, and said second functional group is selected from the group consisting of an azide group, a nitrile-oxide group, a diazo-alkane group, an allene group, a nitrone group, a thiol group, a vinyl sulfone group and a diene group, or vice versa.

The objects of the present invention are solved by a method of preparing a hydrogel of the present invention, said method comprising the step of dissolving a first peptide the present invention or a first peptide obtained by the method of the present invention and, optionally, a second peptide the present invention in an aqueous solution.

DESCRIPTION OF THE PREFERRED EMBODIMENTS OF THE INVENTION

Hydrogels Comprising Peptides Bound to Bioactive Agent(s)

As discussed above, the present invention provides a hydrogel comprising a first peptide having the general formula $$B^*\text{-}Z_p\text{-}(X)_m\text{-}(Y)_n\text{-}Z'_q$$

or $$Z_p\text{-}(X)_m\text{-}(Y)_n\text{-}Z'_q\text{-}B^*$$

or $$B^*\text{-}Z_p\text{-}(X)_m\text{-}(Y)_n\text{-}Z'_q\text{-}B^*$$

wherein
B* is a bioactive agent;
X is, at each occurrence, independently selected from an aliphatic amino acid, an aliphatic amino acid derivative and a glycine;
Y is, at each occurrence, independently selected from a polar amino acid and a polar amino acid derivative;
Z is an N-terminal protecting group;
Z' is a C-terminal protecting group;
m is an integer selected from 2 to 6;
n is selected from 1 or 2; and
p and q are independently selected from 0 or 1, wherein, preferably, p is 0,
wherein said bioactive agent is covalently linked to the N-terminus and/or the C-terminus of said first peptide by means of a click chemistry reaction.

In a preferred embodiment, said first peptide has the general formula

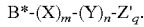
B*-(X)$_m$-(Y)$_n$-Z'$_q$.

In a preferred embodiment, the hydrogel of the present invention further comprises a second peptide having the general formula

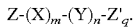
Z-(X)$_m$-(Y)$_n$-Z'$_q$.

Preferably, said bioactive agent is selected from the group consisting of nucleic acids, DNA, RNA, small RNAs, miRNA, mRNA, siRNA, rRNA, snRNA, snoRNA and analogs thereof, (poly)peptides, peptidomimetics, neutral or anionic or cationic polymers, virus particles, (poly)saccharides, oligosaccharides, glycans, vitamins, hormones, steroids, growth factors, sialic acids, antigens, antibiotics, anti-inflammatory molecules, vaccines, drugs, prodrugs, catechols, biotin, lipids and lipid analogs, antibodies, nanoparticles, organometallic compounds and other organic or inorganic compounds, complexes, composites and nanomaterials.

In one embodiment, said bioactive agent is an anti-cancer therapeutic.

In one embodiment, said anti-cancer therapeutic is selected from the group consisting of oxaliplatin, cisplatin, carboplatin, doxorubicin, daunorubicin, clyclophosphamide, 5-fluorouracile, chlorambucil, vincristine, methotrexate, hydroxyurea, bleomecyn, topotecan, irinotecan, dactinomycin, docetaxel, vinblastine, paclitaxel, gleevec, herceptin and other monoclonal or polyclonal antibodies.

In one embodiment, said bioactive agent is covalently linked to the N-terminus and/or the C-terminus of said first peptide via a linking group comprising a moiety selected from the group consisting of a triazole group, a cyclohexene group, a thioether group, a succinimide group, an isoxazole group and analogs thereof, a isoxazolidine group and analogs thereof, and a pyrazoline group.

In one embodiment, said click chemistry reaction is a [3+2] cycloaddition reaction, a Diels-Alder reaction, a thiol-ene reaction, a thiol-Michael addition reaction, a thiol-vinylsulfone reaction, a Staudinger reaction, preferably a 1,3-dipolar cycloaddition reaction, more preferably a Cu(I)-catalyzed or a strained promoted 1,3-dipolar cycloaddition reaction.

In one embodiment, the hydrophobicity decreases from the N-terminus to the C-terminus of said peptide.

In one embodiment, said aliphatic amino acid and aliphatic amino acid derivative are selected from the group consisting of alanine (Ala, A), homoallylglycine, homopropargylglycine, isoleucine (Ile, I), norleucine, leucine (Leu, L) and valine (Val, V).

Preferably, said aliphatic amino acid is selected from the group consisting of alanine (Ala, A), isoleucine (Ile, I), leucine (Leu, L) and valine (Val, V).

In one embodiment, said polar amino acid and polar amino acid derivative are selected from the group consisting of aspartic acid (Asp, D), asparagine (Asn, N), glutamic acid (Glu, E), glutamine (Gln, Q), 5-N-ethyl-glutamine (theanine), citrulline, thio-citrulline, cysteine (Cys, C), homocysteine, methionine (Met, M), ethionine, selenomethionine, telluromethionine, serine (Ser, S), homoserine, arginine (Arg, R), homoarginine, threonine (Thr, T), allo-threonine, lysine (Lys, K), hydroxylysine, N(6)-carboxymethyllysine, ornithine (Orn), 2,4-diaminobutyric acid (Dab), 2,4-diaminopropionic acid (Dap), histidine (His, H), azido-alanine, azido-homoalanine, azido-ornithine and azido-lysine.

Preferably, said polar amino acid and polar amino acid derivative are selected from the group consisting of aspartic acid (Asp, D), glutamic acid (Glu, E), cysteine (Cys, C), serine (Ser, S), threonine (Thr, T), lysine (Lys, K), ornithine (Orn), 2,4-diaminobutyric acid (Dab) and 2,4-diaminopropionic acid (Dap).

In one embodiment, m is selected from 2 to 5.
In one embodiment, m+n is ≤7 or m+n is ≤6.
In one embodiment, (X)$_m$-(Y)$_n$ is selected from the group consisting of

| Sequence | |
|---|---|
| LIVAGDD | SEQ ID NO: 1 |
| LIVAGDE | SEQ ID NO: 2 |
| LIVAGED | SEQ ID NO: 3 |
| LIVAGEE | SEQ ID NO: 4 |
| LIVAGKC | SEQ ID NO: 5 |
| LIVAGSC | SEQ ID NO: 6 |
| AIVAGKC | SEQ ID NO: 7 |
| AIVAGSC | SEQ ID NO: 8 |
| LIVAGC | SEQ ID NO: 9 |
| LIVAGD | SEQ ID NO: 10 |
| ILVAGD | SEQ ID NO: 11 |
| LIVAAD | SEQ ID NO: 12 |
| LAVAGD | SEQ ID NO: 13 |
| AIVAGD | SEQ ID NO: 14 |
| LIVAGE | SEQ ID NO: 15 |
| LIVAGK | SEQ ID NO: 16 |

-continued

| | |
|---|---|
| LIVAGS | SEQ ID NO: 17 |
| ILVAGS | SEQ ID NO: 18 |
| AIVAGS | SEQ ID NO: 19 |
| LIVAGT | SEQ ID NO: 20 |
| AIVAGT | SEQ ID NO: 21 |
| LIVAD | SEQ ID NO: 22 |
| LIVGD | SEQ ID NO: 23 |
| IVAD | SEQ ID NO: 24 |
| IIID | SEQ ID NO: 25 |
| IIIK | SEQ ID NO: 26 |
| IVD | SEQ ID NO: 43 |
| IID | SEQ ID NO: 44 |
| LVE | SEQ ID NO: 45 |
| IVE | SEQ ID NO: 46 |
| LVD | SEQ ID NO: 47 |
| VIE | SEQ ID NO: 48 |
| VID | SEQ ID NO: 49 |
| VLD | SEQ ID NO: 50 |
| VLE | SEQ ID NO: 51 |
| LLE | SEQ ID NO: 52 |
| LLD | SEQ ID NO: 53 |
| IIE | SEQ ID NO: 54 |
| IVK | SEQ ID NO: 55 |
| IV(Orn) | SEQ ID NO: 56 |
| IV(Dab) | SEQ ID NO: 57 |
| IV(Dap) | SEQ ID NO: 58 |
| IVS | SEQ ID NO: 59 |
| LVS | SEQ ID NO: 60 |
| LVK | SEQ ID NO: 61 |
| LV(Orn) | SEQ ID NO: 62 |
| LV(Dab) | SEQ ID NO: 63 |
| LV(Dap) | SEQ ID NO: 64 |
| ILVAGK | SEQ ID NO: 27 |
| ILVAG(Orn) | SEQ ID NO: 28 |
| ILVAG(Dab) | SEQ ID NO: 29 |
| ILVAG(Dap) | SEQ ID NO: 30 |
| ILVAGS | SEQ ID NO: 31 |
| ILVAGKC | SEQ ID NO: 32 |
| AIVAGK | SEQ ID NO: 33 |
| AIVAG(Orn) | SEQ ID NO: 34 |
| AIVAG(Dab) | SEQ ID NO: 35 |
| AIVAG(Dap) | SEQ ID NO: 36 |
| LIVAG(Orn) | SEQ ID NO: 37 |
| LIVAG(Dab) | SEQ ID NO: 38 |
| LIVAG(Dap) | SEQ ID NO: 39 |
| III(Orn) | SEQ ID NO: 40 |
| III(Dab) and | SEQ ID NO: 41 |
| III(Dap). | SEQ ID NO: 42 |

In one embodiment, said N-terminal protecting group has the general formula —C(O)—R, wherein R is selected from the group consisting of H, unsubstituted or substituted alkyls, and unsubstituted or substituted aryls.

Preferably, said N-terminal protecting group is an acetyl group.

In one embodiment, said N-terminal protecting group is a peptidomimetic molecule, including natural and synthetic amino acid derivatives, wherein the N-terminus of said peptidomimetic molecule may be modified with a functional group selected from the group consisting of carboxylic acid, amide, alcohol, aldehyde, amine, imine, nitrile, an urea analog, thiol, phosphate, carbonate, sulfate, nitrate, maleimide, vinyl sulfone, azide, alkyne, alkene, carbohydrate, imide, peroxide, ester, thioester, aryl, ketone, sulphite, nitrite, phosphonate and silane.

Preferably, said C-terminal protecting group is an amide group.

In one embodiment, the C-terminus of said at least one peptide has the formula —CONHR or —CONRR', with R and R' being selected from the group consisting of H, unsubstituted or substituted alkyls, and unsubstituted or substituted aryls.

Preferably, said C-terminal protecting group is an ester group.

In one embodiment, the C-terminus of said at least one peptide has the formula —$CO_2R$, with R being selected from the group consisting of H, unsubstituted or substituted alkyls, and unsubstituted or substituted aryls.

In one embodiment, said C-terminal protecting group is a peptidomimetic molecule, including natural and synthetic amino acid derivatives, wherein the C-terminus of said peptidomimetic molecule may be modified with a functional group selected from the group consisting of carboxylic acid, amide, alcohol, aldehyde, amine, imine, nitrile, an urea analog, thiol, phosphate, carbonate, sulfate, nitrate, maleimide, vinyl sulfone, azide, alkyne, alkene, carbohydrate, imide, peroxide, ester, thioester, aryl, ketone, sulphite, nitrite, phosphonate and silane.

In one embodiment, said second peptide is capable of forming said hydrogel via self-assembly, preferably via antiparallel self-assembly.

In one embodiment, said first peptide is capable of forming said hydrogel via self-assembly, preferably via antiparallel self-assembly.

In one embodiment, the hydrogel is characterized by a storage modulus G' to loss modulus G" ratio that is greater than 2.

In one embodiment, the hydrogel is characterized by a storage modulus G' in the range of from 100 Pa to 100,000 Pa at a frequency in the range of from 0.001 Hz to 16 Hz, preferably 0.01 Hz to 0.2 Hz.

In one embodiment, the hydrogel is injectable and gels in situ.

Uses of the Hydrogels of the Invention

As discussed above, the present invention provides the use of a hydrogel of the present invention for delivery of said bioactive agent, preferably for sustained or controlled release delivery of said bioactive agent.

As discussed above, the present invention provides the use of a hydrogel of the present invention as an implant.

As discussed above, the present invention provides a device for drug delivery, preferably sustained or controlled release drug delivery, comprising a hydrogel of the present invention.

Preferably, the release of the bioactive agent from the hydrogels of the present invention can take place by several different mechanisms, such as by hydrolysis, diffusion and pH change.

As discussed above, the present invention provides an implant comprising a hydrogel of the present invention.

As discussed above, the present invention provides a pharmaceutical or cosmetic composition comprising a hydrogel of the present invention.

Methods of Local Treatment

As discussed above, the present invention provides a method of local treatment of a disease, said method comprising the steps of providing a hydrogel of the present invention at a place in a body where treatment is intended; and allowing said hydrogel to release said bioactive agent.

In one embodiment, step a) is performed by injecting said hydrogel at a place in a body where treatment is intended.

In one embodiment, said disease is cancer.

In one embodiment, said cancer is selected from the group consisting of prostate cancer, breast cancer, colorectal cancer, head and neck tumors, gliomas, liver cancer, bladder cancer, sarcomas, melanomas, non-small-cell lung cancer, genitourinary cancer and other solid tumors.

Kits Comprising the Components of the Hydrogels of the Invention

As discussed above, the present invention provides a kit comprising a first container with a first peptide as defined herein and a second container with an aqueous solution.

In one embodiment, said first container further contains a second peptide as defined herein, or wherein said kit further comprises a third container with a second peptide as defined herein.

Methods for Preparing the Hydrogels of the Invention and its Components

As discussed above, the present invention provides a method of preparing a first peptide as defined herein.

Said method comprises the steps of providing a peptide having the general formula $Z_p$-$(X)_m$-$(Y)_n$-$Z'_q$, preferably $(X)_m$-$(Y)_n$-$Z'_q$;

functionalizing the N-terminus and/or the C-terminus of said peptide with a first functional group;

reacting said peptide comprising said first functional group at its N-terminus and/or C-terminus with a moiety comprising said bioactive agent and a second functional group under conditions suitable for forming said first peptide, wherein said first functional group is selected from the group consisting of an alkyne group, a cyclooctyne group, an alkene group and a maleimide group, and said second functional group is selected from the group consisting of an azide group, a nitrile-oxide group, a diazo-alkane group, an allene group, a nitrone group, a thiol group, a vinyl sulfone group and a diene group, or vice versa.

In one embodiment, said first functional group is an alkyne group or cyclooctyne group, and said second functional group is an azide group, or vice versa.

As discussed above, the present invention provides a method of preparing a hydrogel of the present invention.

Said method comprises the step of dissolving a first peptide as defined herein or a first peptide obtained by the method of the present invention, as defined above, and, optionally, a second peptide as defined herein in an aqueous solution.

In one embodiment, the method further comprises the step(s) of adding at least one buffer, preferably at least one physiologically acceptable buffer; and/or adding at least one compound acting as gelation enhancer.

Preferred Embodiments

The inventors have previously described ultra-short short peptide sequences (3-7 residues) capable of self-assembly into helical fibers that ultimately result in hydrogel formation. See, for example, the international patent application WO 2011/123061 A1 which is enclosed herewith in its entirety.

These hydrogels show remarkable properties with regards to mechanical stiffness, elasticity and biocompatibility and we demonstrated its wide application as biomimetic material. However, when a co-hydrogel, containing a bioactive compound and the peptide was formulated, only a burst release could be observed, a sustained release was never achieved.

The present invention describes a technology that enables to covalently bind bioactive molecules to the peptide. The covalent attachment of bioactive molecules to the hydrogel matrix (the peptide which forms the hydrogel) ensures that the bioactive compound cannot undergo a burst release. In the present disclosure the release of the active compound is triggered via hydrolysis and therefore a sustained release is achieved.

Localized treatment, using in situ gelling delivery systems injected directly into a tumor site are one possible strategy for overcoming problems of poor uptake and systemic effects, as discussed above.

To overcome the problems of the prior art, the present invention utilizes natural biomolecules, namely peptides, which can self-assemble into hydrogels. We recently reported a unique class of ultra-short peptides, which are able to form hydrogels without the need of chemical or UV-crosslinking by simple self-assembly. (See also C. A. E. Hauser, R. Deng, A. Mishra, Y. Loo, U. Khoe, F. Zhuang, D. W. Cheong, A. Accardo, M. B. Sullivan, C. Riekel, J. Y. Ying, U. A. Hauser, *Proceedings of the National Academy of Sciences* 2011, 108, 1361-1366; A. Mishra, Y. Loo, R. Deng, Y. J. Chuah, H. T. Hee, J. Y. Ying, C. A. E. Hauser, *Nano Today* 2011, 6, 232-239.)

The unique character of these ultra-short peptides and their biocompatibility afford them great potential as drug-delivery systems. The ability of these ultra-short peptides to self-assemble into hydrogels via an antiparallel mechanism allows functionalization of the termini of the peptides without interfering with the self-assembling residue. Therefore, the functionalized peptide would still be able to assemble by itself or when mixed with its parent peptide, forming hybrid hydrogels (FIG. 1).

Description of Results

A series of propiolic acid functionalized peptides, namely LIVAGK-NH$_2$ (SEQ ID NO. 16 amidated), IVK-NH$_2$ (SEQ ID NO: 70), LIVAGD-OH (SEQ ID NO. 10) and IVD-OH (SEQ ID NO: 58) were synthesized by standard Fmoc solid phase peptide synthesis. The N-terminus functionalization was performed on the solid phase-bound peptide, using HOBT as coupling reagent without the addition of a base. The beads were washed after the coupling with a solution of 10% DIPEA in DMF. The final coupling was repeated until the Kaiser test showed negative. The alkyne residue allows for a fast and efficient derivatization of the peptides with bioactive cues via click chemistry. We chose cisplatin and oxaliplatin derived precursors as bioactive test compounds. Here, 2-(3-azidopropyl)-2-methylmalonic acid was used as the biscarboxilato ligand yielding carboplatin and oxaliplatin analogues following standard synthetic protocols. The azide functionality on complex 1 and 2 (see FIG. 16 for structure details) allows the attachment to the alkyne functionalized peptide via a Cu(I) catalyzed 1,3-dipolar cycloaddition reaction, as shown in Scheme 1. We investigated different reaction conditions and the best yield was obtained when CuSO$_4$.5H$_2$O was reduced to Cu(I) in situ using sodium ascorbate, and H$_2$O/tBuOH/DMF in a ratio of 10:10:1 as solvent was used. The addition of DMF helps in solubilisation of the starting compounds. Significantly lower yield was observed when CuBr in pure DMF was used as catalyst.

To test the gelation ability of compounds 3-8, they were dissolved in water by vortexing and left to stand overnight. However, even with a concentration of 40 mg/mL, only clear solutions were obtained, and no hydrogel formation was observed. Interestingly, these peptide metal conjugates showed much higher water solubility than either oxaliplatin or cisplatin alone. In contrast, the alkyne-derived peptide P1 gelled in water at a concentration of 30 mg/mL, which is close to the minimal gelation concentration of its parent peptide SEQ ID NO 16 Ac-LIVAGK-NH$_2$ (Ac-LK$_6$-NH$_2$). Compounds P2-P4 showed similar gelation behaviour to P1. We assume, that the derivatization of the peptides with cisplatin or oxaliplatin and a bulky triazole group interferes with their self-assembly by changing the lipophilicity of the N-terminus of the peptide. However, stable hybrid gels could be formed with up to 40 wt % loading when the parent peptide was used as a matrix.

Morphological characterization of the peptide hydrogel scaffolds was done by FESEM and the results for Ac-LIVAGK-NH$_2$(SEQ ID NO. 16), P1 and 3 are shown in FIG. 3. All three compounds show a similar morphology that can be described as mostly flat sheets with fibre-like structures visible on the surface.

Cytotoxicity of all synthesized compounds was evaluated on two human derived cancer cell lines namely HeLa (cervical carcinoma) and SW480 (colon carcinoma). 4T1 mouse breast cancer cells were also used for evaluation. Cells were first treated with different concentrations of the test compounds and incubated for 96 h at 37° C. Subsequently, the cell viability was measured by means of a colorimetric microculture assay (MTS assay). IC$_{50}$ values obtained are listed in Table 1.

TABLE 1

Cytotoxicity of platinum peptide conjugate 3-8 compared to cisplatin and oxaliplatin in three cancer cell lines.

| Compound | IC$_{50}$ [µM] | | |
|---|---|---|---|
| | HeLa | SW480 | 4T1 |
| 3 | 4.4 ± 2.3 | 1.5 ± 0.8 | 2.9 ± 0.8 |
| 4 | 7.7 ± 1.4 | 1.5 ± 0.7 | 6.7 ± 0.9 |
| 5 | 3.4 ± 1.5 | 1.6 ± 1.1 | 2.1 ± 1.0 |
| 6 | 6.2 ± 1.3 | 2.3 ± 1.2 | 4.1 ± 1.0 |
| 7 | 8.7 ± 5.2 | 38.6 ± 8.6 | 38.2 ± 4.0 |
| 8 | 37.4 ± 3.4 | 46.9 ± 21.3 | 12.0 ± 0.1 |
| cisplatin | 1.0 ± 0.8 | 4.0 ± 2.5 | 1.5 ± 0.6 |
| oxaliplatin | 2.0 ± 0.8 | 0.47 ± 0.1 | 1.8 ± 0.5 |

The control compound cisplatin exhibited IC$_{50}$ values of 0.62±0.1 µM and 2.2±0.3 µM for HeLa and 4T1 cells respectively. In contrast, the cisplatin-derived peptide conjugates 7 and 8 showed much lower activity across all cell lines, with IC$_{50}$ values ranging from 2.9-42.3 µM. In general, no significant difference in IC$_{50}$ values between cisplatin-sensitive and cisplatin-resistant cell lines could be observed for compound 7 and 8. We therefore decided to focus on investigations on the oxaliplatin-derived peptide conjugates 3-6. In this case, the observed IC$_{50}$ values were significantly lower than those for the cisplatin analogues and very close to the IC$_{50}$ values of the oxaliplatin control. All four conjugates showed promising IC$_{50}$ values, being most active in SW480 cells (IC$_{50}$=1.7-2.5 µM) which are known to respond very well to oxaliplatin (IC$_{50}$=0.5 µM). In addition, IC$_{50}$ values close to or even better than the control could be detected in the other two cell lines.

To further characterize the in vitro efficacy of 3-6, cell cycle analysis and measurement of caspase activity was conducted after incubation with the drug candidates. Specifically, we compared the response of SW480 cells to that exhibited by 4T1 cells to compounds 3-6. Similar to observations reported in the literature (S. William-Faltaos, D. Rouillard, P. Lechat, G. Bastian, *Fundamental & Clinical Pharmacology* 2007, 21, 165-172.), we found that oxaliplatin induces an arrest in the G2 phase, which can be observed for both SW480 and 4T1 cells (see FIG. 6 and FIG. 7). Oxaliplatin coordinates to DNA nucleotides, preventing the cell from crossing the DNA damage check point. In 4T1 cells about 30% of the cells were apoptotic whereas no apoptotic cells were found in SW480 cells. Compound 3-6 showed similar results in both cell lines where a G2/M arrest was observed. Interestingly, for the 4T1 cells, only about 30% were in G2/M arrest for compound 6 whereas 60-70% of the cells were arrested in G2/M for compound 3-5. This is very close to the oxaliplatin control were about 55% of the cells were in a G2/M arrest. However, the oxaliplatin control also showed about 30% apoptotic cells, which is significantly higher than that observed for compound 3-5; only compound 6 had 25% apoptotic cells. In SW480 cells, about 80% of the oxaliplatin control showed a G2/M arrest. This is significantly higher than that observed for 3-6, where only about 15-25% of the cells were arrested in G2. The fact that all compounds were associated with an increase in the G2/M phase proves that compound 3-6 is able to bind to DNA in the tested cells, although the effect is not as pronounced as in the oxaliplatin control.

We further wanted to confirm that compound 3-6 is able to induce apoptosis and looked into the caspase 3/7 activity. The highest caspase activity was detected after 72 h of incubation with 10 μM of test compound (FIG. 8 and FIG. 9). All tested compounds induced similar caspase 3/7 activity (within error of the measurement) as the control oxaliplatin. No significant difference in caspase 3/7 activity was detected between SW480 and 4T1 cells. Based on the promising in vitro efficacy of all tested oxaliplatin-derived complexes in 4T1 cells, we decided to move forward and evaluate the effects in an in vivo mouse model.

Female BALB/c mice were divided into four groups for treatment (PBS group and Ac-LIVAGK-NH$_2$ (SEQ ID NO. 16 acylated and amidated) hydrogel group as negative controls, oxaliplatin as positive control and test compound 3 as a hybrid hydrogel with Ac-LIVAGK-NH$_2$ (SEQ ID NO. 16 acylated and amidated)). Each group comprised of 9 mice. Tumour growth was initiated via a subcutaneous injection of 1 million 4T1 cells into the mouse flank. Seven days after cell injection, compound 3 was directly injected into the tumor using Ac-LIVAGK-NH$_2$ (SEQ ID NO. 16 acylated and amidated), its parent peptide, as gel matrix. The same volume was accordingly injected into the other three groups. As a first dose 15 mg/kg oxaliplatin was used, which is equivalent to 44 mg/kg of compound 3. A re-injection was performed on day 21 of the experiment. The animals were sacrificed on day 28 and final tumor size was measured.

Results of the tumor size measurements on day 7, day 14, day 21 and day 28 are shown in FIG. 3. Statistical analysis was done using ANOVA to quantitatively discern significant differences among the groups for each time point based on tumor size Significant tumor reduction was observed for the groups treated with oxaliplatin and conjugate 3, seven days post injection, in comparison with the PBS control group. The same holds true for day 21 of the experiment. Oxaliplatin displayed a greater effect on tumor size than conjugate 3. However, oxaliplatin appeared to have a significant deleterious effect on the mice compared to conjugate 3, at the administered dose. This was confirmed by a significant weight difference between the oxaliplatin group and the group treated with compound 3. Therefore, reinjection on day 21 involved only half the initial dose. On day 28 no statistically significant difference between the oxaliplatin group and the mice treated with 3 was found. However, the group treated with the hybrid hydrogel containing compound 3 showed significant tumor growth inhibition when compared to the control group treated with the hydrogels alone. These results clearly prove the potential of this new drug delivery system for a localized cancer treatment.

In conclusion, the technology disclosed herein describes the functionalization of self-assembling ultra-short peptides with platinum anti-cancer drugs by click chemistry. The presented synthetic strategy is a very general approach and can be used to attach a variety of bioactive molecules. We showed that the functionalized peptides can be used for localized cancer therapy using its parent peptide as matrix. Here, the peptide residue of compound 3-6 helps it self-assemble into hydrogels when mixed with its parent peptide sequence. Stable gels could be formed with up to 40% loading by weight. All compounds showed promising in vitro activity, especially the oxaliplatin-derived ones. The possibility of using these compounds for localised in vivo treatment was tested and very promising results have been obtained.

Further Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The term "amino acid" includes compounds in which the carboxylic acid group is shielded by a protecting group in the form of an ester (including an ortho ester), a silyl ester, an amide, a hydrazide, an oxazole, an 1,3-oxazoline or a 5-oxo-1,3,-oxazolidine. The term "amino acid" also includes compounds in which an amino group of the form —NH$_2$ or —NHR$^1$ (supra) is shielded by a protecting group. Suitable amino protecting groups include, but are not limited to, a carbamate, an amide, a sulfonamide, an imine, an imide, histidine, a N-2,5,-dimethylpyrrole, an N-1,1,4,4-tetramethyldisilyl-azacyclopentane adduct, an N-1,1,3,3-tetramethyl-1,3-disilisoindoline, an N-diphenylsilyldiethylene, an 1,3,5-dioxazine, a N-[2-(trimethylsilyl)ethoxy]methylamine, a N-(5,5-dimethyl-3-oxo-1-cyclohexenyl)amine, a N-4,4,4-trifluoro-3-oxo-1-butenylamine, a N-9-borabicyclononane and a nitroamine. A protecting group may also be present that shields both the amino and the carboxylic group such as e.g. in the form of a 2,2-dimethyl-4-alkyl-2-sila-5-oxo-1,3-oxazolidine. The alpha carbon atom of the amino acid typically further carries a hydrogen atom. The so called "side chain" attached to the alpha carbon atom, which is in fact the continuing main chain of the carboxylic acid, is an aliphatic moiety that may be linear or branched. The term "side chain" refers to the presence of the amino acid in a peptide (supra), where a backbone is formed by coupling a plurality of amino acids. An aliphatic moiety bonded to the α carbon atom of an amino acid included in such a peptide then defines a side chain relative to the backbone. As explained above, the same applies to an aliphatic moiety bonded to the amino group of the amino acid, which likewise defines a side chain relative to the backbone of a peptoid.

The term "aliphatic" means, unless otherwise stated, a straight or branched hydrocarbon chain, which may be saturated or mono- or poly-unsaturated and include heteroatoms. The term "heteroatom" as used herein means an atom of any element other than carbon or hydrogen. An unsaturated aliphatic group contains one or more double and/or triple bonds (alkenyl or alkynyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, preferably such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain heteroatoms as for instance N, O, S, Se or Si or carbon atoms may be replaced by these heteroatoms.

An aliphatic moiety may be substituted or unsubstituted with one or more functional groups. Substituents may be any functional group, as for example, but not limited to, amino, amido, azido, carbonyl, carboxyl, keto, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methanesulfonyl.

As should be apparent from the above, the side chain of an amino acid in a peptide described herein may be of a length of 0 to about 5, to about 10, to about 15 or to about 20 carbon atoms. It may be branched and include unsaturated carbon-carbon bonds. In some embodiments one or more natural amino acids are included in the peptide. Such a natural amino acid may be one of the 20 building blocks of naturally occurring proteins.

In a peptide, including a peptide disclosed herein individual amino acids are covalently coupled via amide bonds between a carboxylic group of a first and an amino group of a second amino acid.

The peptides utilized in the present invention comprise an amphiphilic sequence $(X_m)$-$(Y_n)$.

The term "amphiphilic" refers to a compound that is soluble in both polar and non-polar fluids. It also encompasses multiphase compounds. The amphiphilic properties of the peptide are due to the presence of both polar and non-polar moieties within the same peptide. In this regard the peptide may be of surfactant nature. Accordingly, the polar properties of a peptide disclosed herein are based on a polar moiety. Two such moieties are a —COOH side group, in particular in the form of a charged COO⁻ group and an amino group. A further such moiety is a C-terminal —COOH group if it is present in free, unprotected form. Generally, a surfactant molecule includes a polar, typically hydrophilic, head group attached to a non-polar, typically hydrocarbon, moiety. Non-polar moieties of a peptide include a hydrocarbon chain that does not carry a functional group.

An amphiphilic linear sequence included in a peptide disclosed herein thus includes a polar moiety and a non-polar moiety. The polar moiety includes an aliphatic amino acid that carries a polar group such as a hydroxyl group, a thiol group, a seleno group, an amino group, an amide group, an ether group, a thioether group or a seleno ether group. Accordingly, the polar moiety may include an amino acid that carries a functional polar group with a proton such as hydroxyl, thiol, selenol, amine or amide. The polar moiety may also include the C-terminus or the N-terminus of the peptide. The C-terminus or the N-terminus may in such a case be present in the form of the free carboxyl or amino group, respectively, i.e. free of a protecting group.

Generally the polar moiety of a linear amphiphilic sequence of an amphiphilic peptide disclosed herein is defined by a single amino acid or by two consecutive amino acids that is/are coupled to the non-polar moiety of the peptide. Accordingly, in some embodiments the polar moiety of the peptide consists of two amino acids that are covalently coupled via an amide bond, both amino acids carrying a polar peptide side chain. One of these two amino acids may be a terminal amino acid of the peptide, defining its N- or C-terminus. In some embodiments the amphiphilic peptide has a single amino acid with a polar side chain with the residual portion of the peptide defining the non-polar moiety. In some embodiments the amphiphilic peptide has two amino acids with a polar side chain while the residual portion of the peptide defines the non-polar moiety. As three illustrative examples of a respective polar side chain may serve 4-methyl-4-thio-pentyl, 6-ethoxycarbonyl-4,5-dimethyl-hexyl and 6-hydroxy-4-(1-hydroxyethyl)-hexyl groups. As used herein, the numbering of corresponding peptide side chains is started with "1" at the carbon atom that is covalently bonded to the α-carbon atom of the amino acid or to the amino group of the amino acid, respectively. Amino acids included in the polar moiety may be or include, but are not limited to, aspartic acid, asparagine, glutamic acid, 4-fluoro-glutamic acid, 2-aminoadipic acid, γ-carboxy-glutamic acid, 4-tert-butyl aspartic acid, glutamine, 5-N-ethyl-glutamine (theanine), citrulline, thio-citrulline, cysteine, homocysteine, methionine, ethionine, selenomethionine, telluromethionine, threonine, allo-threonine, serine, homoserine, arginine, homoarginine, ornithine, lysine, 5-hydroxylysine and N(6)-carboxymethyllysine. Any such amino acid may be present in the L- or D-form.

The amphiphilic linear sequence of the amphiphilic peptide disclosed herein can be defined as having n amino acids. Where a single amino acid with a polar side chain is included in the amphiphilic linear sequence, the non-polar moiety may then be taken to have n−1 amino acids. In this case the polar moiety consists of exactly one amino acid, such amino acid being selected from any amino acids of the foregoing paragraph. Where two consecutive amino acids with a polar side chain are included in the amphiphilic linear sequence of the peptide, the non-polar moiety may then be taken to have n−2 amino acids. In this case the polar moiety consists of exactly two amino acids. Where three consecutive amino acids with a polar side chain are included in the amphiphilic linear sequence, the non-polar moiety may then be taken to have n−3 amino acids. In this case the polar moiety consists of exactly three amino acids. In embodiments where the polar moiety consists of two amino acids, the polar moiety may have a sequence selected from Asn-Asn, Asp-Asp, Glu-Glu, Gln-Gln, Asn-Gln, Gln-Asn, Asp-Gln, Gln-Asp, Asn-Glu, Glu-Asn, Asp-Glu, Glu-Asp, Gln-Glu, Glu-Gln, Asp-Asn, Asn-Asp, Thr-Thr, Ser-Ser, Thr-Ser, Ser-Thr, Asp-Ser, Ser-Asp, Ser-Asn, Asn-Ser, Gln-Ser, Ser- Gln, Glu-Ser, Ser-Glu, Asp-Thr, Thr-Asp, Thr-Asn, Asn-Thr, Gln-Thr, Thr-Gln, Glu-Thr, Thr-Glu. In embodiments where the polar moiety consists of three amino acids, the polar moiety may have a sequence selected from Asn-Asn-Asn, Asn-Asn-Asp, Asn-Asp-Asn, Asp-Asn-Asn, Asp-Asp-Asn, Asp-Asn-Asp, Asp-Asp-Asp, Asn-Asn-Glu, Asn-Asn-Gln, Asn-Glu-Asn, Asn-Gln-Asn, Glu-Glu-Glu, Gln-Gln-Gln, Asn-Gln-Gln, Asn-Glu-Gln, Asp-Asn-Glu, Gln-Asn-Asn, Gln-Asn-Asn, Glu-Asp-Gln, Asp-Gln-Asp, Asn-Glu-Asp, Glu-Asn-Gln, Asp-Glu-Gln, Asn-Glu-Gln, Glu-Asp-Asn, and Gln-Asp-Asn, Thr-Thr-Thr, Ser-Ser-Ser, Asn-Thr-Thr, Asn-Ser-Ser Asn-Ser-Thr, Asn-Thr-Ser Asp-Asn-Ser, Ser-Asn-Asn, Thr-Asn-Asn, Ser-Asp-Thr, to name a few.

The amphiphilic linear sequence of the peptide has a net charge at physiological pH. The term "physiological pH" is known to those in the art to refer to the pH value of blood, which has typically a pH value of about 7.4. In embodiments where the amphiphilic linear sequence is arranged at the C- or N-terminus of the peptide, the respective terminus may provide the corresponding net charge. In embodiments where the amphiphilic linear sequence is not arranged at the C- or N-terminus of the peptide, the polar moiety of the amphiphilic linear sequence includes one or more amino acids that have a side chain with a functional group that is charged at physiological pH. Illustrative examples of a respective functional group include an amino, a nitro-, a guanidino, a esteryl, a sulfonyl or a carboxyl group. In some embodiments the net charge of the amphiphilic linear sequence is, as a positive or negative charge, equal to or smaller than the number of amino acids included in the polar moiety thereof. In some embodiments the net charge of the amphiphilic linear sequence is one of −3, −2 or −1. In some embodiments the net charge of the amphiphilic linear sequence is one of +1, +2 or +3.

The respective polar side chain of an amino acid of the polar moiety, coupled to the α-carbon atom of the amino acid (supra) and/or to the amino group thereof, may typically be defined by a main chain that includes 1 to about 20, including 1 to about 15, 1 to about 10 or 1 to about 5 carbon atoms. For sake of clarity it is recited that the term "side chain" is used relative to the backbone of the peptide. This peptide side chain may be branched and thus be defined by a main chain and branches. Both the main chain and branches, if present, of the peptide side chain may include one or more double or triple bonds (supra). Examples of side chains include, but are not limited to, methyl, ethyl, propyl, isopropyl, propenyl, propinyl, butyl, butenyl, sec-butyl, tert-butyl, isobutyl, pentyl, neopentyl, isopentyl, pentenyl, hexyl, 3,3 dimethylbutyl, heptyl, octyl, nonyl or decyl groups. The functional polar group is bonded to this the peptide side chain.

In some embodiments the polar moiety of the amphiphilic linear sequence includes two identical amino acids. Where these amino acids are naturally occurring amino acids, they may for example define one of the sequences Lys-Lys, Gln-Gln, Glu-Glu, Asp-Asp, Asn-Asn, Met-Met, Thr-Thr, Arg-Arg or Ser-Ser. The term "naturally occurring" in this context refers to the 20 amino acids into which the genetic code is directly being translated by any organism. Such two identical polar amino acids may for example be adjacent to the non-polar moiety.

In some embodiments the amphiphilic linear sequence of the peptide has a hydrophobic tail of aliphatic amino acids and at least one polar, including a charged, amino acid head group.

The non-polar moiety includes an amino acid, generally at least two amino acids, with a hydrocarbon chain that does not carry a functional group. The respective side chain, coupled to the α-carbon atom of the amino acid (supra), may have a main chain that includes 0 to about 20 or 1 to about 20, including 0 to about 15, 1 to about 15, 0 to about 10, 1 to about 10, 1 to about 5 or 0 to about 5 carbon atoms. The non-polar moiety may thus include an amino acid without side chain, i.e. glycine. The peptide side chain may be branched (supra) and include one or more double or triple bonds (supra). Examples of peptide side chains include, but are not limited to, methyl, ethyl, propyl, isopropyl, propenyl, propinyl, butyl, butenyl, sec-butyl, tert-butyl, isobutyl, pentyl, neopentyl, isopentyl, pentenyl, hexyl, 3,3 dimethylbutyl, heptyl, octyl, nonyl or decyl groups. As a few illustrative examples, the non-polar moiety may include an amino acid of alanine, valine, leucine, isoleucine, norleucine, norvaline, 2-(methylamino)-isobutyric acid, 2-amino-5-hexynoic acid. Such an amino acid may be present in any desired configuration. Bonded to the non-polar moiety may also be the C-terminus or the N-terminus of the peptide. Typically the C-terminus or the N-terminus is in such a case shielded by a protecting group (supra).

In some embodiments the non-polar moiety includes a sequence of amino acids that is arranged in decreasing or increasing size. Hence, a portion of the amino acids of the non-polar moiety may be arranged in a general sequence of decreasing or increasing size. Relative to the direction from N- to C-terminus or from C- to N-terminus this general sequence can thus be taken to be of decreasing size. By the term "general sequence" of decreasing or increasing size is meant that embodiments are included in which adjacent amino acids are of about the same size as long as there is a general decrease or increase in size. Within a general sequence of decreasing size the size of adjacent amino acids of the non-polar moiety is accordingly identical or smaller in the direction of the general sequence of decreasing size. In some embodiments the general sequence of decreasing or increasing size is a non-repetitive sequence.

As an illustrative example, where a respective portion of amino acids is a sequence of five amino acids, the first amino acid may have a 3,4-dimethyl-hexyl side chain. The second amino acid may have a neopentyl side chain. The third amino acid may have a pentyl side chain. The fourth amino acid may have a butyl side chain. The fifth amino acid may be glycine, i.e. have no side chain. Although a neopentyl and a pentyl side chain are of the same size, the general sequence of such a non-polar peptide portion is decreasing in size. As a further illustrative example of a general sequence of decreasing size in a non-polar moiety the respective non-polar portion may be a sequence of three amino acids. The first amino acid may have an n-nonyl side chain. The second amino acid may have a 3-ethyl-2-methyl-pentyl side chain. The third amino acid may have a tert-butyl side chain. As yet a further illustrative example of a general sequence of decreasing size in a non-polar moiety, the non-polar moiety may be a sequence of nine amino acids. The first amino acid may have a 4-propyl-nonyl side chain. The second amino acid may have an n-dodecyl side chain. The third amino acid may have a 6,6-diethyl-3-octenyl side chain. An n-dodecyl side chain and a 6,6-diethyl-3-octenyl side chain both have 12 carbon atoms and thus again have a comparable size, Nevertheless, the 6,6-diethyl-3-octenyl group includes an unsaturated carbon-carbon bond and is thus of slightly smaller size than the dodecyl group. The fourth amino acid may have a 2-methyl-nonyl side chain. The fifth amino acid may have a 3-propyl-hexyl side chain. The sixth amino acid may have an n-hexyl side chain. The seventh amino acid may have a 2-butynyl side chain. The 8th amino acid may have an isopropyl side chain. The ninth amino acid may have a methyl side chain.

Where a portion of the amino acids of the non-polar moiety arranged in a general sequence of decreasing (or increasing) size only contains naturally occurring amino acids (whether in the D- or the L-form), it may for example have a length of five amino acids, such as the sequence leucine-isoleucine-valine-alanine-glycine (SEQ ID NO.43) or isoleucine-leucine-valine-alanine-glycine (SEQ ID NO 44), A general sequence of decreasing size of only natural amino acids may also have a length of four amino acids. Illustrative examples include the sequences isoleucine-leucine-valine-alanine (SEQ ID NO. 45), leucine-isoleucine-valine-alanine (SEQ ID NO. 46), isoleucine-valine-alanine-glycine (SEQ ID NO. 47), leucine-valine-alanine-glycine (SEQ ID NO. 48), leucine-isoleucine-alanine-glycine (SEQ ID NO. 49), leucine-isoleucine-valine-glycine (SEQ ID NO. 50), isoleucine-leucine-alanine-glycine (SEQ ID NO. 51) or isoleucine-leucine-valine-glycine (SEQ ID NO. 52). A general sequence of decreasing size of only natural amino acids may also have a length of three amino acids. Illustrative examples include the sequences isoleucine-valine-alanine, leucine-valine-alanine, isoleucine-valine-glycine, leucine-valine-glycine, leucine-alanine-glycine, isoleucine-alanine-glycine or isoleucine-leucine-alanine. A general sequence of decreasing size of only natural amino acids may also have a length of two amino acids. Illustrative examples include the sequences isoleucine-valine, leucine-valine, isoleucine-alanine, leucine-alanine, leucine-glycine, isoleucine-glycine, valine-alanine, valine-glycine or alanine-glycine.

In some embodiments the direction of decreasing size of the above defined general sequence of decreasing size is the direction toward the polar moiety of the amphiphilic linear sequence. Accordingly, in such embodiments the size of adjacent amino acids within this portion of the non-polar moiety is accordingly identical or smaller in the direction of the polar moiety. Hence, as a general trend in such an embodiment, the closer to the polar moiety of the amphiphilic linear sequence, the smaller is the overall size of a peptide side chain throughout the respective general sequence of decreasing size. In the above illustrative example of a general sequence of three amino acids with a n-nonyl, a 3-ethyl-2-methyl-pentyl and a tert-butyl side chain, the next amino acid may be polar in that it carries a peptide side chain with a polar functional group. As an illustrative example, adjacent to the tert-butyl side chain within the peptide there may be a 3-carboxy-n-butyl side chain.

In some embodiments the entire non-polar moiety of the amphiphilic linear peptide or the amphiphilic linear sequence, respectively, consists of the general sequence of decreasing (or increasing) size. In such an embodiment the general sequence of decreasing (or increasing) size may have a length of n–m amino acids (cf. above). In some embodiments the general sequence of decreasing or increasing size is flanked by further non-polar side chains of the peptide. In one embodiment the general sequence of decreasing (or increasing) size has a length of n–m–1 amino acids. In this embodiment there is one further amino acid included in the peptide, providing a non-polar peptide side chain. This amino acid may be positioned between the general sequence of decreasing (or increasing) size and the polar amino acid, the polar amino acid may be positioned between this additional non-polar amino acid and the general sequence of decreasing (or increasing) size or the general sequence of decreasing (or increasing) size may be positioned between the polar amino acid and this additional non-polar amino acid. Typically the general sequence of decreasing (or increasing) size is positioned between the polar amino acid and this additional non-polar amino acid. The additional non-polar amino acid may for example define the N-terminus of the peptide, which may be shielded by a protecting group such as an amide, e.g. a propionic acyl or an acetyl group. Together with the general sequence of decreasing (or increasing) size as defined above it may define the non-polar portion of the peptide. The polar amino acid may define the C-terminus of the peptide. In this example the general sequence of decreasing (or increasing) size is thus flanked by the polar amino acid on one side and by the additional non-polar amino acid on the other side. In one embodiment where embodiment the general sequence of decreasing (or increasing) size has a length of n–m–1 amino acids, the remaining non-polar amino acid of the non-polar moiety of n–m amino acids is one of alanine and glycine.

As explained above, the polar moiety of the amphiphilic linear sequence may in some embodiments be defined by two consecutive amino acids. The polar moiety includes n aliphatic amino acids. Each of the n aliphatic amino acids is independently selected and carries an independently selected polar group. The symbol n represents an integer selected from 1 and 2. The at least essentially non-polar moiety (supra) accordingly has a number of m–n, i.e. m–1, m–2 amino acids. In some embodiments m is equal to or larger than n+2. In such an embodiment m may thus represent a number of m–2 or smaller.

In an embodiment where the entire non-polar moiety of the amphiphilic linear peptide consists of the general sequence of decreasing (or increasing) size (supra), this non-polar moiety may thus have a length of m–2 amino acids. In an embodiment where the amphiphilic linear peptide has a further non-polar side chain in addition to the non-polar moiety of decreasing (or increasing) size, this additional non-polar side chain may be included in an amino acid that is directly bonded to an amino acid of the general sequence of decreasing (or increasing) size. The non-polar moiety may thus be defined by the non-polar moiety of decreasing (or increasing) size and the respective further amino acid with a non-polar side chain. In one such an embodiment where n=1, the non-polar moiety may thus have a length of m–2 amino acids. The general sequence of decreasing (or increasing) size may be positioned between the two polar amino acids and this additional non-polar amino acid, or the additional non-polar amino acid may be positioned between the general sequence of decreasing (or increasing) size and the two polar amino acids. Typically the general sequence of decreasing (or increasing) size is positioned between the two polar amino acids and this additional non-polar amino acid. As mentioned above, one of the two polar amino acids may define the C-terminus of the peptide. In this example the general sequence of decreasing (or increasing) size may thus be flanked by the two consecutive polar amino acids on one side and by the additional non-polar amino acid on the other side. Again, in some embodiments where n=1 the two consecutive polar amino acids may also be positioned between the general sequence of decreasing (or increasing) size and the additional non-polar amino acid, in which case the non-polar moiety has a first portion with a length of m–3 amino acids and a further portion of one amino acid.

Electrostatic forces, hydrogen bonding and van der Waals forces between amphiphilic linear sequences as defined above, including amphiphilic linear peptides, result in these amphiphilic linear sequences to be coupled to each other.

Without being bound by theory, thereby a cross-linking effect occurs that allows the formation of a hydrogel. In this regard the inventors have observed the formation of fibers based on helical structures.

The fibers formed of amphiphilic linear sequences of amphiphilic peptides disclosed herein typically show high mechanical strength, which renders them particularly useful in tissue regeneration applications, for instance the replacement of damaged tissue. Amphiphilic peptides disclosed herein have been observed to generally assemble into a fiber structure that resembles collagen fibers. Collagen, a component of soft tissue in the animal and human body, is a fibrous protein that provides most of the tensile strength of tissue. The mechanical strength of fibers of amphiphilic peptides disclosed herein has been found to typically be much higher than that of collagen (cf. e.g. Figures) of gelatine, the hydrolysed form of collagen. An amphiphilic peptide disclosed herein may thus be included in a hydrogel that is used as permanent or temporary prosthetic replacement for damaged or diseased tissue.

The amphiphilic linear sequence of the peptide, which may represent the entire amphiphilic peptide (supra) has been found to show remarkable stability at physiological conditions, even at elevated temperatures. It is in some embodiments stable in aqueous solution at physiological conditions at ambient temperature for a period of time in the range from 1 day to 1 month or more. It may in some embodiments be stable in aqueous solution at physiological conditions at 90° C. for at least 1 hour, at least 2 hours, at least 3 hours, at least 4 hours or at least 5 hours An amphiphilic linear sequence of an amphiphilic peptide including an amphiphilic linear peptide, is capable of providing a self assembling α-helical fiber in aqueous solution under physiological conditions. The peptides (typically 3-7-mers) in the L- or D-form can self assemble into supramolecular helical fibers which are organized into mesh-like structures mimicking biological substances such as collagen. It has previously been observed in X-ray crystallography that peptides of a length of 3 to 6 amino acids with repetitive alanine containing sequences and an acetylated C-terminus take a helical conformation (Hatakeyama, Y, et al, Angew. Chem. Int. Ed. (2009) 8695-8698). Using peptides with an amphiphilic sequence, Ac-LD$_6$ (L), the formation of aggregates has for example been observed already at 0.1 mg/ml. As the concentration of peptide is increased to 1 mg/ml, the peptide monomers were found to align to form fibrous structures. With a formation of fibers occurring under physiological conditions at concentrations below 2 mM a peptide is well suited as an injectable hydrogel material that can form a hydrogel under physiological conditions. Also disclosed herein is an amphiphilic linear peptide as defined above for tissue engineering as well as to a tissue engineering method that involves applying, including injecting a respective amphiphilic linear peptide.

A hydrogel is typically characterized by a remarkable rigidity and are generally biocompatible and non-toxic. Depending on the selected peptide sequence these hydrogels can show thermoresponsive or thixotropic character. Reliant on the peptide assembling conditions the fibers differ in thickness and length. Generally rigid hydrogels are obtained that are well suited for cultivation of a variety of primary human cells, providing peptide scaffolds that can be useful in the repair and replacement of various tissues. Disclosed is also a process of preparing these hydrogels. The exemplary usage of these hydrogels in applications such as cell culture, tissue engineering, plastic surgery, drug delivery, oral applications, cosmetics, packaging and the like is described, as well as for technical applications, as for example for use in electronic devices which might include solar or fuel cells.

As an amphiphilic linear sequence of the peptide, a hydrogel shows high stability at physiological conditions, even at elevated temperatures. In some embodiments such a hydrogel is stable in aqueous solution at ambient temperature for a period of at least 7 days, at least 14 days, at least a month or more, such as at least 1 to about 6 months.

According to the invention, the first peptide comprised in a hydrogel disclosed herein is coupled to bioactive agent.

Said bioactive agent is preferably selected from the group consisting of nucleic acids, DNA, RNA, small RNAs, miRNA, mRNA, siRNA, rRNA, snRNA, snoRNA and analogs thereof, (poly)peptides, peptidomimetics, neutral or anionic or cationic polymers, virus particles, (poly)saccharides, oligosaccharides, glycans, vitamins, hormones, steroids, growth factors, sialic acids, antigens, antibiotics, anti-inflammatory molecules, vaccines, drugs, prodrugs, catechols, biotin, lipids and lipid analogs, antibodies, nanoparticles, organometallic compounds and other organic or inorganic compounds, complexes, composites and nanomaterials.

In some embodiments said bioactive agent is a molecule with binding affinity for a selected target molecule, such as a microorganism, a virus particle, a peptide, a peptoid, a protein, a nucleic acid, a peptide, an oligosaccharide, a polysaccharide, an inorganic molecule, a synthetic polymer, a small organic molecule or a drug.

The term "nucleic acid molecule" as used herein refers to any nucleic acid in any possible configuration, such as single stranded, double stranded or a combination thereof. Nucleic acids include for instance DNA molecules (e.g., cDNA or genomic DNA), RNA molecules (e.g., mRNA), analogues of the DNA or RNA generated using nucleotide analogues or using nucleic acid chemistry, locked nucleic acid molecules (LNA), and protein nucleic acids molecules (PNA). DNA or RNA may be of genomic or synthetic origin and may be single or double stranded. In the present method of an embodiment of the invention typically, but not necessarily, an RNA or a DNA molecule will be used. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label. In some embodiments the nucleic acid molecule may be isolated, enriched, or purified. The nucleic acid molecule may for instance be isolated from a natural source by cDNA cloning or by subtractive hybridization. The natural source may be mammalian, such as human, blood, semen, or tissue. The nucleic acid may also be synthesized, e.g. by the triester method or by using an automated DNA synthesizer.

Many nucleotide analogues are known and can be used in nucleic acids and oligonucleotides used in the methods of exemplary embodiments of the invention. A nucleotide analogue is a nucleotide containing a modification at for instance the base, sugar, or phosphate moieties. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases. Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

A peptide may be of synthetic origin or isolated from a natural source by methods well-known in the art. The natural source may be mammalian, such as human, blood, semen, or tissue. A peptide, including a polypeptide may for instance be synthesized using an automated polypeptide synthesizer. Illustrative examples of polypeptides are an antibody, a fragment thereof and a proteinaceous binding molecule with antibody-like functions. Examples of (recombinant) antibody fragments are Fab fragments, Fv fragments, single-chain Fv fragments (scFv), diabodies, triabodies (Iliades, P., et al., FEBS Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). An example of a proteinaceous binding molecule with antibody-like functions is a mutein based on a polypeptide of the lipocalin family (WO 03/029462, Beste et al., Proc. Natl. Acad. Sci. U.S.A. (1999) 96, 1898-1903). Lipocalins, such as the bilin binding protein, the human neutrophil gelatinase-associated lipocalin, human Apolipoprotein D or glycodelin, posses natural ligand-binding sites that can be modified so that they bind to selected small protein regions known as haptens. Examples of other proteinaceous binding molecules are the so-called glubodies (see e.g. internation patent application WO 96/23879), proteins based on the ankyrin scaffold (Mosavi, L. K., et al., Protein Science (2004) 13, 6, 1435-1448) or crystalline scaffold (e.g. internation patent application WO 01/04144) the proteins described in Skerra, J. Mol. Recognit. (2000) 13, 167-187, AdNectins, tetranectins and avimers. Avimers contain so called A-domains that occur as strings of multiple domains in several cell surface receptors (Silverman, J., et al., Nature Biotechnology (2005) 23, 1556-1561). Adnectins, derived from a domain of human fibronectin, contain three loops that can be engineered for immunoglobulin-like binding to targets (Gill, D. S. & Damle, N. K., Current Opinion in Biotechnology (2006) 17, 653-658). Tetranectins, derived from the respective human homotrimeric protein, likewise contain loop regions in a C-type lectin domain that can be engineered for desired binding (ibid.). Where desired, a modifying agent may be used that further increases the affinity of the respective moiety for any or a certain form, class etc. of target matter.

An example of a nucleic acid molecule with antibody-like functions is an aptamer. An aptamer folds into a defined three-dimensional motif and shows high affinity for a given target structure. Using standard techniques of the art such as solid-phase synthesis an aptamer with affinity to a certain target can accordingly be formed and immobilized on a hollow particle of an embodiment of the invention.

As a further illustrative example, a linking moiety such as an affinity tag may be used to immobilise the respective molecule/bioactive agent. Such a linking moiety may be a molecule, e.g. a hydrocarbon-based (including polymeric) molecule that includes nitrogen-, phosphorus-, sulphur-, carben-, halogen- or pseudohalogen groups, or a portion thereof. As an illustrative example, the peptide included in the hydrogel may include functional groups, for instance on a side chain of the peptide, that allow for the covalent attachment of the biomolecule/bioactive agent, for example a molecule such as a protein, a nucleic acid molecule, a polysaccharide or any combination thereof. A respective functional group may be provided in shielded form, protected by a protecting group that can be released under desired conditions. Examples of a respective functional group include, but are not limited to, an amino group, an aldehyde group, a thiol group, a carboxy group, an ester, an anhydride, a sulphonate, a sulphonate ester, an imido ester, a silyl halide, an epoxide, an aziridine, a phosphoramidite and a diazoalkane.

Examples of an affinity tag include, but are not limited to, biotin, dinitrophenol or digoxigenin, oligohistidine, polyhistidine, an immunoglobulin domain, maltose-binding protein, glutathione-S-transferase (GST), calmodulin binding peptide (CBP), FLAG'-peptide, the T7 epitope (Ala-Ser-Met-Thr-Gly-Gly-Gln-Gln-Met-Gly) (SEQ ID NO. 53), maltose binding protein (MBP), the HSV epitope of the sequence Gln-Pro-Glu-Leu-Ala-Pro-Glu-Asp-Pro-Glu-Asp (SEQ ID NO. 54) of herpes simplex virus glycoprotein D, the hemagglutinin (HA) epitope of the sequence Tyr-Pro-Tyr-Asp-Val-Pro-Asp-Tyr-Ala (SEQ ID NO. 56), the "myc" epitope of the transcription factor c-myc of the sequence Glu-Gln-Lys-Leu-Ile-Ser-Glu-Glu-Asp-Leu (SEQ ID NO. 55), or an oligonucleotide tag. Such an oligonucleotide tag may for instance be used to hybridise to an immobilised oligonucleotide with a complementary sequence. A further example of a linking moiety is an antibody, a fragment thereof or a proteinaceous binding molecule with antibody-like functions (see also above).

A further example of linking moiety is a cucurbituril or a moiety capable of forming a complex with a cucurbituril. A cucurbituril is a macrocyclic compound that includes glycoluril units, typically self-assembled from an acid catalyzed condensation reaction of glycoluril and formaldehyde. A cucurbit[n]uril, (CB[n]), that includes n glycoluril units, typically has two portals with polar ureido carbonyl groups. Via these ureido carbonyl groups cucurbiturils can bind ions and molecules of interest. As an illustrative example cucurbit[7]uril (CB[7]) can form a strong complex with ferrocenemethylammonium or adamantylammonium ions. Either the cucurbit[7]uril or e.g. ferrocenemethylammonium may be attached to a biomolecule, while the remaining binding partner (e.g. ferrocenemethylammonium or cucurbit[7]uril respectively) can be bound to a selected surface. Contacting the biomolecule with the surface will then lead to an immobilisation of the biomolecule. Functionalised CB [7] units bound to a gold surface via alkanethiolates have for instance been shown to cause an immobilisation of a protein carrying a ferrocenemethylammonium unit (Hwang, I., et al., J. Am. Chem. Soc. (2007) 129, 4170-4171).

Further examples of a linking moiety include, but are not limited to an oligosaccharide, an oligopeptide, biotin, dinitrophenol, digoxigenin and a metal chelator (cf. also below). As an illustrative example, a respective metal chelator, such as ethylenediamine, ethylenediaminetetraacetic acid (EDTA), ethylene glycol tetraacetic acid (EGTA), diethylenetriaminepentaacetic acid (DTPA), N,N-bis(carboxymethyl)glycine (also called nitrilotriacetic acid, NTA), 1,2-bis(o-aminophenoxy)ethane-N,N,N',N'-tetraacetic acid (BAPTA), 2,3-dimercapto-1-propanol (dimercaprol), porphine or heme may be used in cases where the target molecule is a metal ion. As an example, EDTA forms a complex with most monovalent, divalent, trivalent and tetravalent metal ions, such as e.g. silver ($Ag^+$), calcium ($Ca^{2+}$), manganese ($Mn^{2+}$), copper ($Cu^{2+}$), iron ($Fe^{2+}$), cobalt ($Co^{3+}$) and zirconium ($Zr^{4+}$), while BAPTA is specific for $Ca^{2+}$. In some embodiments a respective metal chelator in a complex with a respective metal ion or metal ions defines the linking moiety. Such a complex is for example a receptor molecule for a peptide of a defined sequence, which may also be included in a protein. As an illustrative example, a standard method used in the art is the formation of a complex between an oligohistidine tag and copper ($Cu^{2+}$), nickel ($Ni^{2+}$), cobalt ($Co^{2+}$), or zink ($Zn^{2+}$) ions, which are presented by means of the chelator nitrilotriacetic acid (NTA).

Avidin or streptavidin may for instance be employed to immobilise a biotinylated nucleic acid, or a biotin containing monolayer of gold may be employed (Shumaker-Parry, J. S., et al., Anal. Chem. (2004) 76, 918). As yet another illustrative example, the biomolecule may be locally deposited, e.g. by scanning electrochemical microscopy, for instance via pyrrole-oligonucleotide patterns (e.g. Fortin, E., et al., Electroanalysis (2005) 17, 495). In other embodiments, in particular where the biomolecule is a nucleic acid, the biomolecule may be directly synthesised on the surface of the immobilisation unit, for example using photoactivation and deactivation. As an illustrative example, the synthesis of nucleic acids or oligonucleotides on selected surface areas (so called "solid phase" synthesis) may be carried out using electrochemical reactions using electrodes. An electrochemical deblocking step as described by Egeland & Southern (Nucleic Acids Research (2005) 33, 14, e125) may for instance be employed for this purpose. A suitable electrochemical synthesis has also been disclosed in US patent application US 2006/0275927. In some embodiments light-directed synthesis of a biomolecule, in particular of a nucleic acid molecule, including UV-linking or light dependent 5'-deprotection, may be carried out.

The molecule that has a binding affinity for a selected target molecule may be immobilised on the nanocrystals by any means. As an illustrative example, an oligo- or polypeptide, including a respective moiety, may be covalently linked to the surface of nanocrystals via a thio-ether-bond, for example by using w functionalized thiols. Any suitable molecule that is capable of linking a nanocrystal of an embodiment of the invention to a molecule having a selected binding affinity may be used to immobilise the same on a nanocrystal. For instance a (bifunctional) linking agent such as ethyl-3-dimethylaminocarbodiimide, N-(3-aminopropyl) 3-mercapto-benzamide, 3-aminopropyl-trimethoxysilane, 3-mercaptopropyl-trimethoxysilane, 3-(trimethoxysilyl) propyl-maleimide, or 3-(trimethoxysilyl) propyl-hydrazide may be used. Prior to reaction with the linking agent, the surface of the nanocrystals can be modified, for example by treatment with glacial mercaptoacetic acid, in order to generate free mercaptoacetic groups which can then employed for covalently coupling with an analyte binding partner via linking agents.

Embodiments of the present invention also include a hydrogel, which can be taken to be a water-swollen water-insoluble polymeric material. The hydrogel includes, including contains and consists of, a peptide as defined above. Since a hydrogel maintains a three-dimensional structure, a hydrogel of an embodiment of the invention may be used for a variety of applications. Since the hydrogel has a high water content and includes amino acids, it is typically of excellent biocompatibility.

A hydrogel according to an embodiment of the invention is formed by self-assembly. The inventors have observed that the peptides assemble into fibers that form mesh-like structures. Without being bound by theory hydrophobic interaction between non-polar portions of peptides are contemplated to assist such self-assembly process.

The method of forming the hydrogel includes dissolving the first and/or second peptide in aqueous solution. Agitation, including mixing such as stirring, and/or sonication may be employed to facilitate dissolving the peptide. In some embodiments the aqueous solution with the peptide therein is exposed to a temperature below ambient temperature, such as a temperature selected from about 2° C. to about 15° C. In some embodiments the aqueous solution with the peptide therein is exposed to an elevated temperature, i.e. a temperature above ambient temperature. Typically the aqueous solution is allowed to attain the temperature to which it is exposed. The aqueous solution may for example be exposed to a temperature from about 25° C. to about 85° C. or higher, such as from about 25° C. to about 75° C., from about 25° C. to about 70° C., from about 30° C. to about 70° C., from about 35° C. to about 70° C., from about 25° C. to about 60° C., from about 30° C. to about 60° C., from about 25° C. to about 50° C., from about 30° C. to about 50° C. or from about 40° C. to about 65° C., such as e.g. a temperature of about 40° C., about 45° C., about 50° C., about 55° C., about 60° C. or about 65° C. The aqueous solution with the peptide therein may be maintained at this temperature for a period of about 5 min to about 10 hours or more, such as about 10 min to about 6 hours, about 10 min to about 4 hours, about 10 min to about 2.5 hours, about 5 min to about 2.5 hours, about 10 min to about 1.5 hours or about 10 min to about 1 hour, such as about 15 min, about 20 min, about 25 min, about 30 min, about 35 min or about 40 min.

In some embodiments a hydrogel disclosed herein is a biocompatible, including a pharmaceutically acceptable hydrogel. The term "biocompatible" (which also can be referred to as "tissue compatible"), as used herein, is a hydrogel that produces little if any adverse biological response when used in vivo. The term thus generally refers to the inability of a hydrogel to promote a measurably adverse biological response in a cell, including in the body of an animal, including a human. A biocompatible hydrogel can have one or more of the following properties: non-toxic, non-mutagenic, non-allergenic, non-carcinogenic, and/or non-irritating. A biocompatible hydrogel, in the least, can be innocuous and tolerated by the respective cell and/or body. A biocompatible hydrogel, by itself, may also improve one or more functions in the body.

Depending on the amino acids that are included in the peptide that is included in a hydrogel, a respective hydrogel may be biodegradable. A biodegradable hydrogel gradually disintegrates or is absorbed in vivo over a period of time, e.g., within months or years. Disintegration may for instance occur via hydrolysis, may be catalysed by an enzyme and may be assisted by conditions to which the hydrogel is exposed in a human or animal body, including a tissue, a blood vessel or a cell thereof. Where a peptide is made up entirely of natural amino acids, a respective peptide can usually be degraded by enzymes of the human/animal body.

A hydrogel according to an embodiment of the invention may also serve as a depot for a pharmaceutically active compound such as a drug. A hydrogel according to an embodiment of the invention may be designed to mimic the natural extracellular matrix of an organism such as the human or animal body. A fiber formed from the peptide of an embodiment of the invention, including a respective hydrogel, may serve as a biological scaffold. A hydrogel of an embodiment of the invention may be included in an implant, in a contact lens or may be used in tissue engineering. In one embodiment, the peptides consist typically of 3-7 amino acids and are able to self-assemble into complex fibrous scaffolds which are seen as hydrogels, when dissolved in water or aqueous solution. These hydrogels can retain water up to 99.9% and possess sufficiently high mechanical strength. Thus, these hydrogels can act as artificial substitutes for a variety of natural tissues without the risk of immunogenicity. The hydrogels in accordance with the present invention may be used for cultivating suitable primary cells and thus establish an injectable cell-matrix compound in order to implant or reimplant the newly formed cell-matrix in vivo. Therefore, the hydrogels in accordance with the present invention are particularly useful for tissue regeneration or tissue engineering applications. As used herein, a reference to an "implant" or "implantation" refers to uses and applications of/for surgical or arthroscopic implantation of a hydrogel containing device into a human or animal, e.g. mammalian, body or limb. Arthroscopic techniques are taken herein as a subset of surgical techniques, and any reference to surgery, surgical, etc., includes arthroscopic techniques, methods and devices. A surgical implant that includes a hydrogel according to an embodiment of the invention may include a peptide scaffold. This the peptide scaffold may be defined by the respective hydrogel. A hydrogel of an embodiment of the invention may also be included in a wound cover such as gauze or a sheet, serving in maintaining the wound in a moist state to promote healing.

Depending on the amino acid sequence used in the peptide the hydrogel may be temperature-sensitive. It may for instance have a lower critical solution temperature or a temperature range corresponding to such lower critical solution temperature, beyond which the gel collapses as hydrogen bonds by water molecules are released as water molecules are released from the gel.

The disclosed subject matter also provides improved chiral amphiphilic natural-based peptides that assemble to peptide hydrogels with very favorable material properties. The advantage of these peptide hydrogels is that they are accepted by a variety of different primary human cells, thus providing peptide scaffolds that can be useful in the repair and replacement of various tissues. Depending on the chirality of the peptide monomer the character of the hydrogels can be designed to be more stable and less prone to degradation though still biocompatible.

A hydrogel and/or a peptide described herein can be administered to an organism, including a human patient per se, or in pharmaceutical compositions where it may include or be mixed with pharmaceutically active ingredients or suitable carriers or excipient(s). Techniques for formulation and administration of respective hydrogels or peptides resemble or are identical to those of low molecular weight compounds well established in the art. Exemplary routes include, but are not limited to, oral, transdermal, and parenteral delivery. A hydrogel or a peptide may be used to fill a capsule or tube, or may be provided in compressed form as a pellet. The peptide or the hydrogel may also be used in injectable or sprayable form, for instance as a suspension of a respective peptide.

A hydrogel of an embodiment of the invention may for instance be applied onto the skin or onto a wound. Further suitable routes of administration may, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections. It is noted in this regard that for administering microparticles a surgical procedure is not required. Where the microparticles include a biodegradable polymer there is no need for device removal after release of the anti-cancer agent. Nevertheless the microparticles may be included in or on a scaffold, a coating, a patch, composite material, a gel or a plaster.

In some embodiments one may administer a hydrogel and/or a peptide in a local rather than systemic manner, for example, via injection.

Pharmaceutical compositions that include a hydrogel and/or a peptide of an embodiment of the present invention may be manufactured in a manner that is itself known, e. g., by means of conventional mixing, dissolving, granulating, dragee-making, levigating, emulsifying, encapsulating, entrapping or lyophilizing processes.

Pharmaceutical compositions for use in accordance with an embodiment of the present invention thus may be formulated in conventional manner using one or more physiologically acceptable carriers including excipients and auxiliaries that facilitate processing of the hydrogel and/or peptide into preparations that can be used pharmaceutically. Proper formulation is dependent upon the route of administration chosen.

For injection, the peptide of an embodiment of the invention may be formulated in aqueous solutions, for instance in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the hydrogel and/or peptide can be formulated readily by combining them with pharmaceutically acceptable carriers well known in the art. Such carriers enable the hydrogel and/or peptide, as well as a pharmaceutically active compound, to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatine, as well as soft, sealed capsules made of gelatine and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the peptides may be suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

The hydrogel and/or peptide may be formulated for parenteral administration by injection, e.g., by intramuscular injections or bolus injection or continuous infusion.

Formulations for injection may be presented in unit dosage form, e. g., in ampules or in multi-dose containers, with an added preservative. The respective compositions may take such forms as suspensions, solutions or emulsions in oily or aqueous vehicles, and may contain formulatory agents such as suspending, stabilizing and/or dispersing agents.

The hydrogel and/or peptide may be formulated for other drug delivery systems like implants, or tranderdermal patches or stents.

BRIEF DESCRIPTION OF THE DRAWINGS

Reference is now made to the figures, wherein.

EXAMPLES

Figure 1:
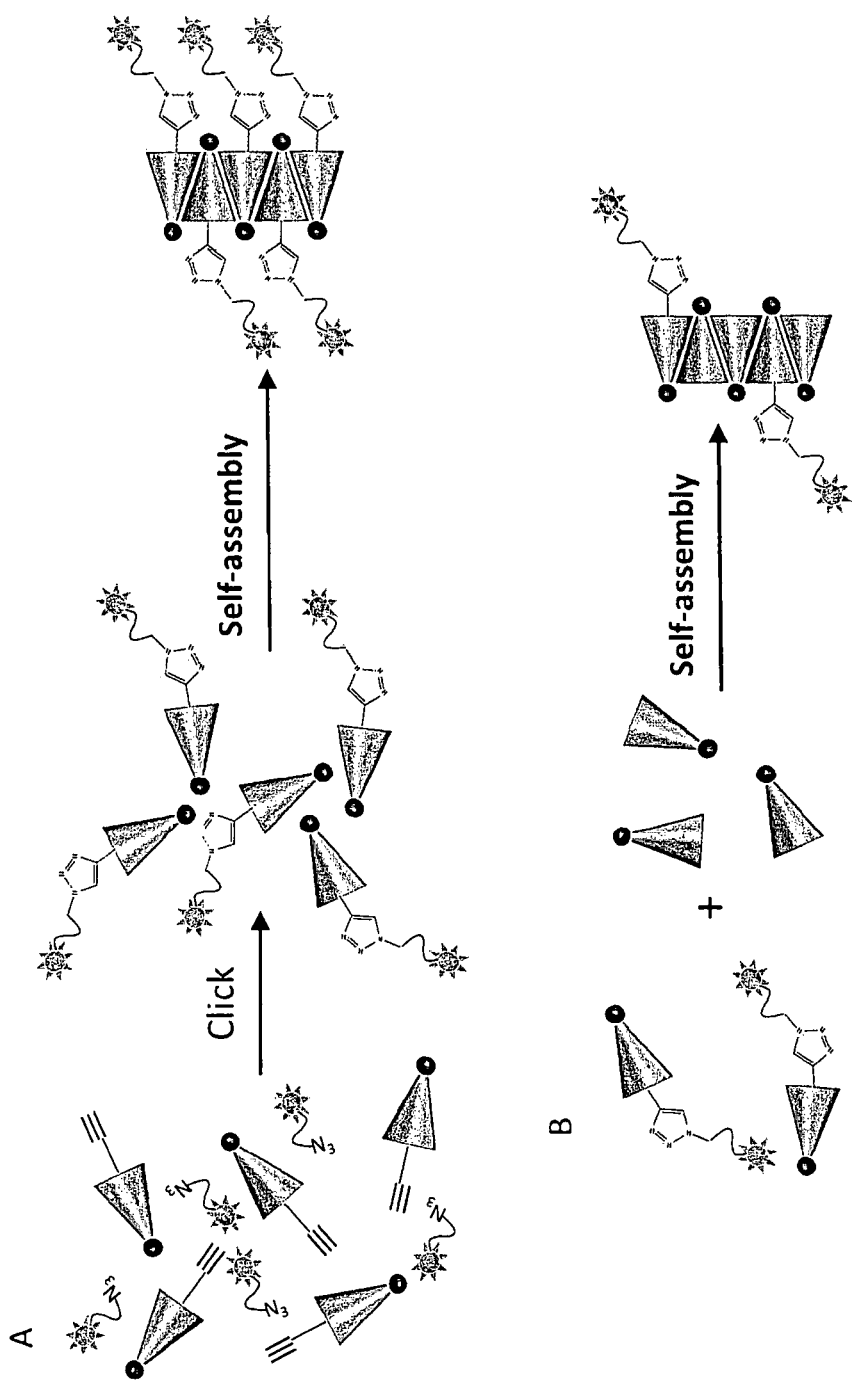
FIG. 1. Schematic drawing of the functionalization and self-assembling of a) peptides which have been functionalized with a bio active cue by click chemistry and b) hybrid peptide gel formation using functionalized ultra-short peptides and the parent peptide itself.
Figure 2:
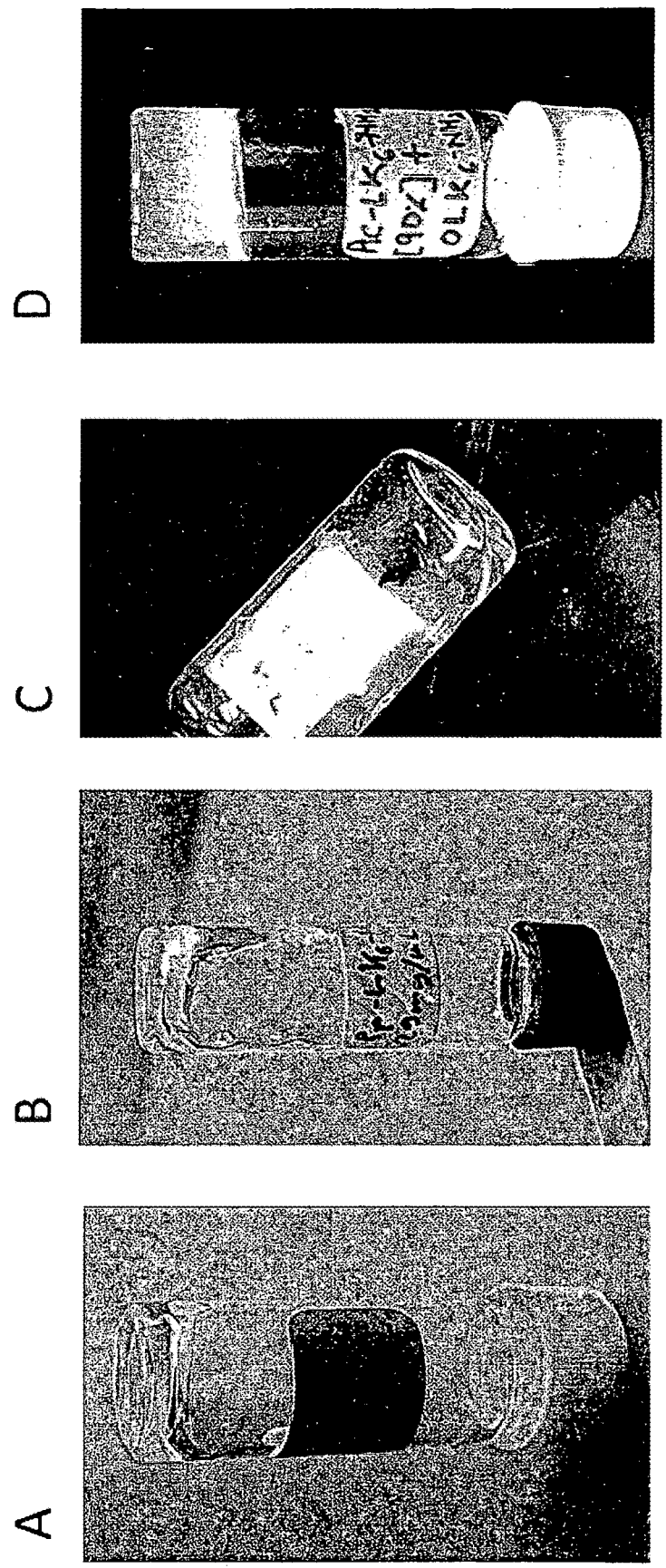
FIG. 2. Pictures of: A) Ac-LIVAGK-NH$_2$ (SEQ ID NO. 16 acylated and amidated) with 25 mg/ml, B) peptide P1 with 29 mg/mL C) solution of complex 3 with 40 mg/mL and D) co-gel of 10 w % of compound 3 and 90 w % of Ac-LIVAGK-NH$_2$ (SEQ ID NO. 16 acylated and amidated).
Figure 3:
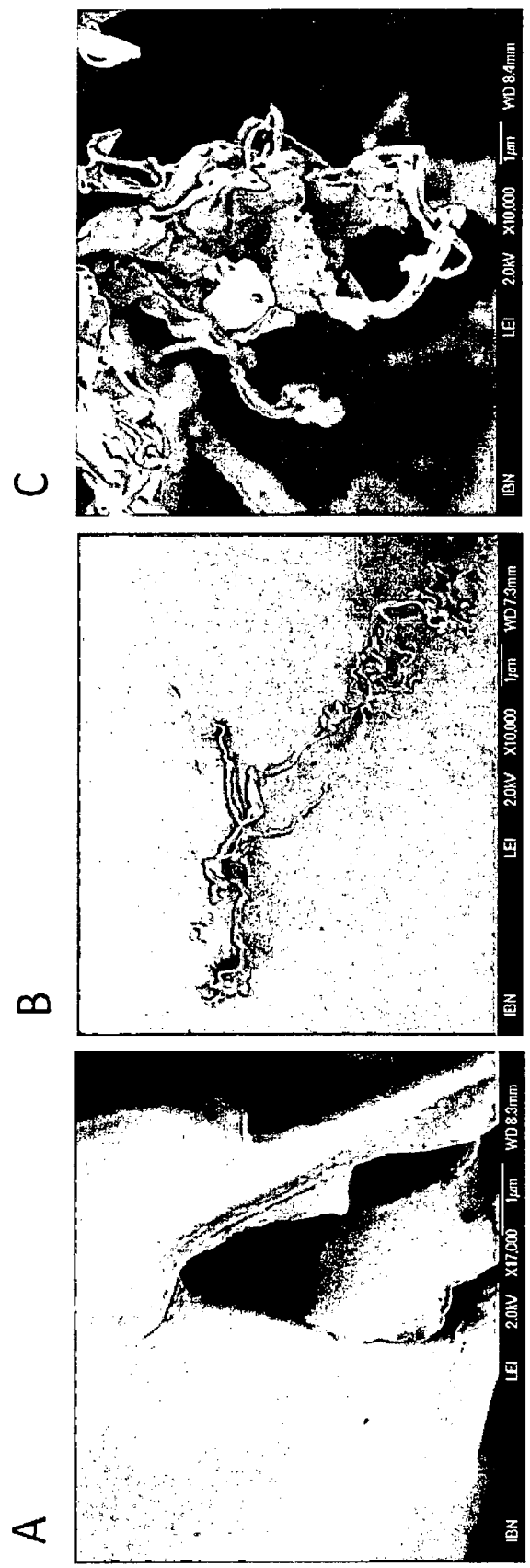
FIG. 3. Morphological characterization of peptide hydrogels by field emission scanning electron microscopy (FE-SEM).
A) Ac-LIVAGK-NH$_2$ (SEQ ID NO. 16 acylated and amidated) with 10 mg/ml, B) peptide P1 with 29 mg/mL C) solution of complex 3 with 40 mg/mL.
Figure 4:
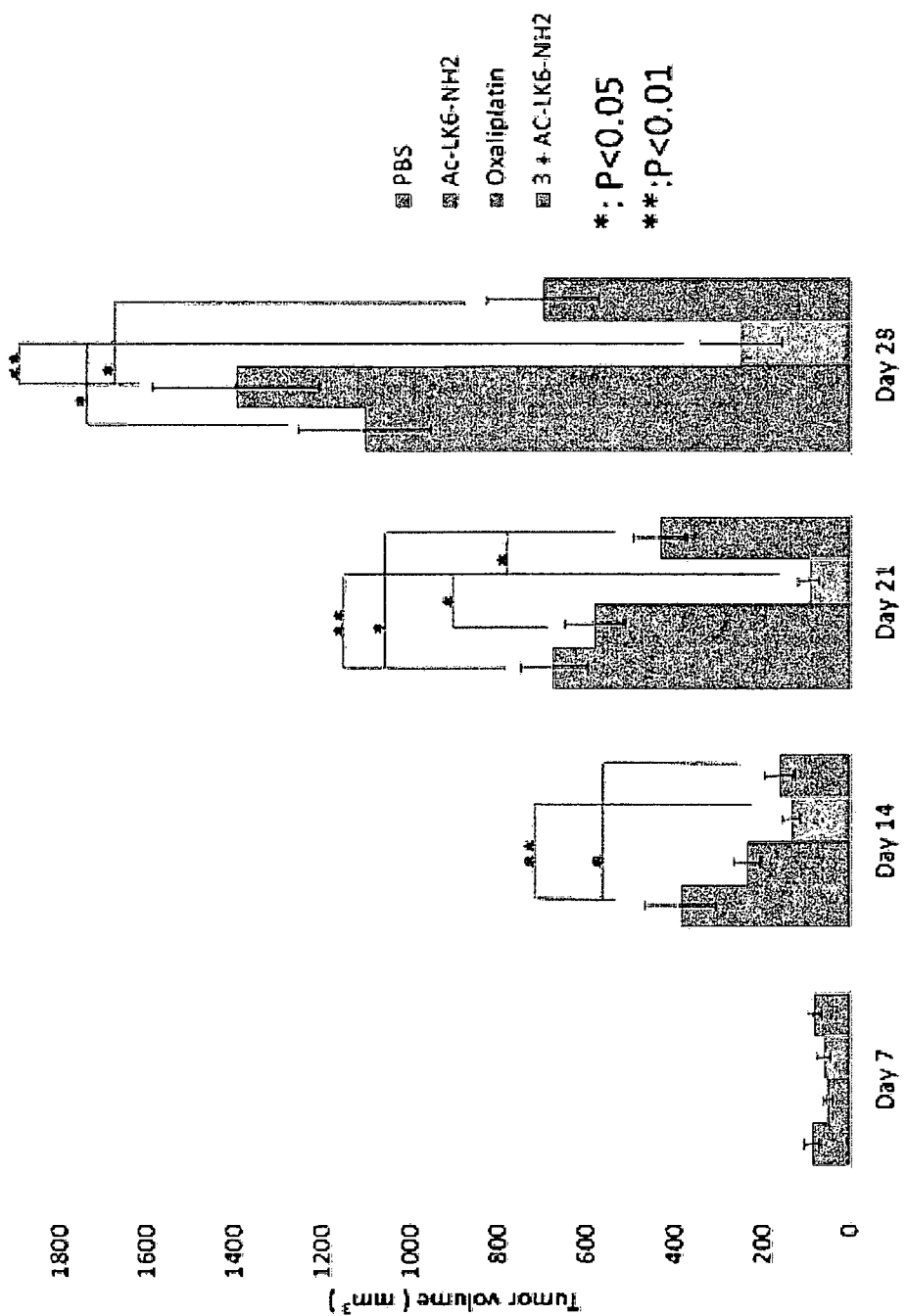
FIG. 4. Effects of tested oxaliplatin-derived complexes on 4T1 breast cancer growth. BALB/c mice after injected with 4T1 breast cancer cells (designated as day 0) were divided into four groups to receive different treatments at day 7. Tumor volume was measured at day 7, 14, 21, and 28 post-tumor inoculation and shown (Mean±SE, n=9 per group). One way ANOVA was performed (*: P<0.05, **: P<0.01) to reveal significant differences among the groups for each time point.
Figure 5:
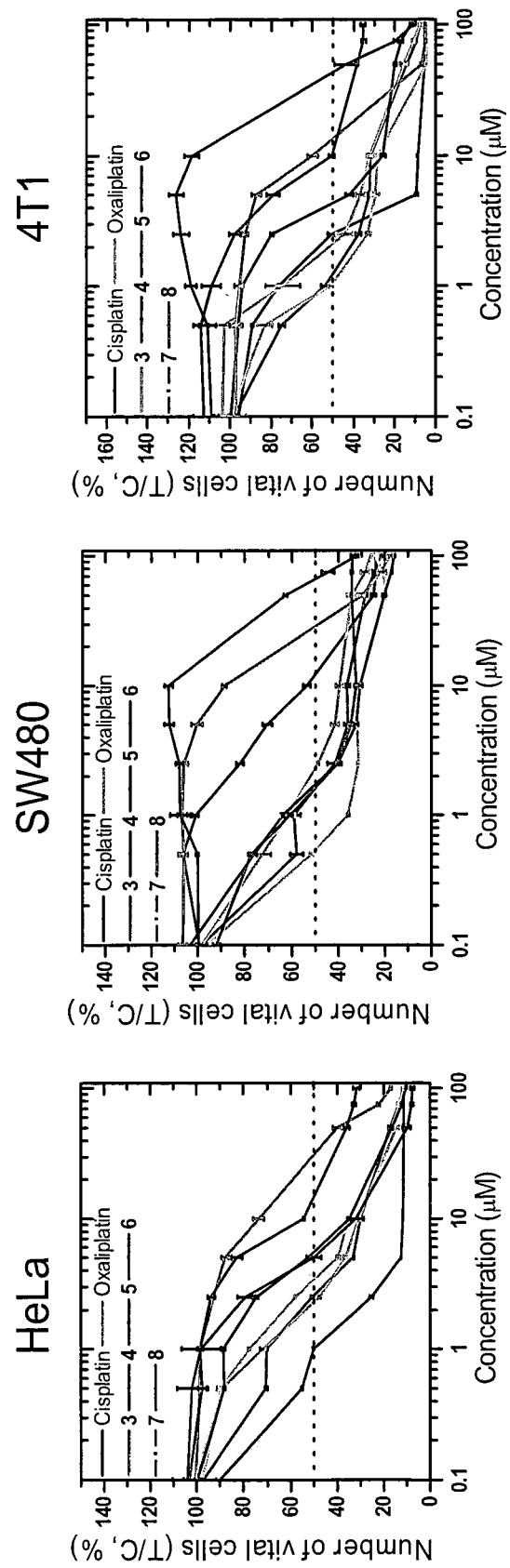
FIG. 5. Concentration effect curve of compound 3-8 in HeLa, SW480 and 4T1 cells in comparison with cisplatin and oxaliplatin FIG. 6. Cell cycle analysis of complex 3 in comparison with untreated cells (negative control) and oxaliplatin (positive control) for SW480 cells. The concentration used was 10 μM for both compound 3 and oxaliplatin.
Figure 6:
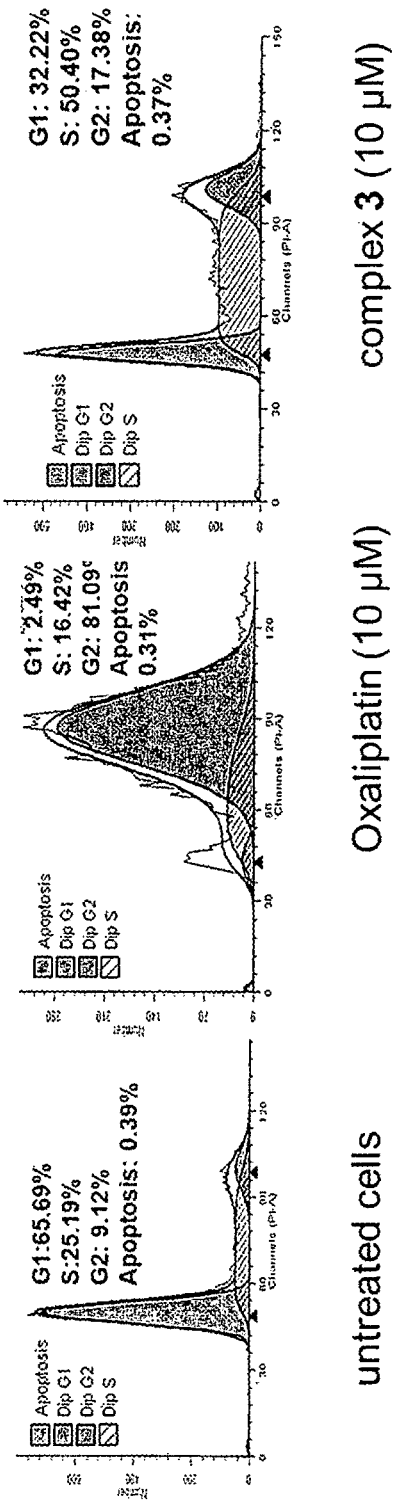
Figure 7:
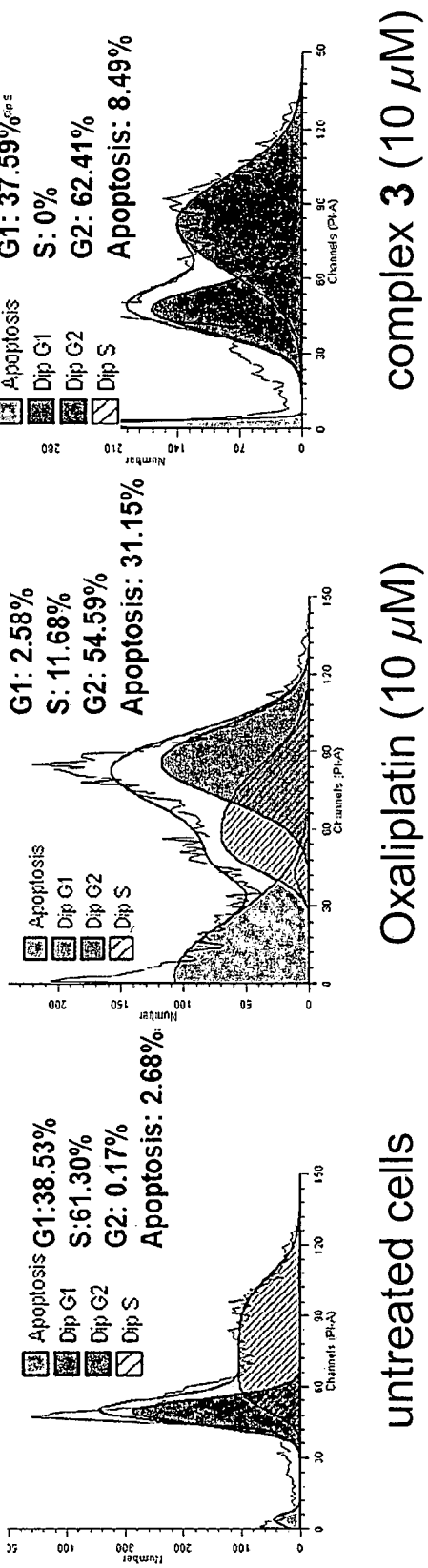
FIG. 7. Cell cycle analysis of complex 3 in comparison with untreated cells (negative control) and oxaliplatin (positive control) for 4T1 cells. The concentration used was 10 μM for both compound 3 and oxaliplatin.
Figure 8:
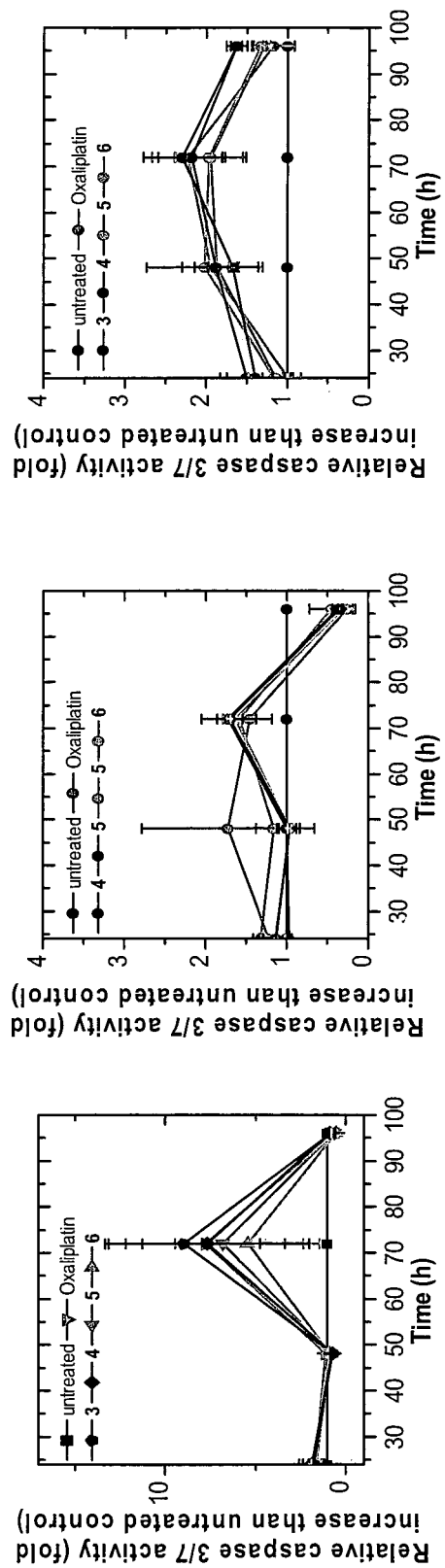
FIG. 8. Time dependence of caspase 3/7 activity in HeLa, SW480 and 4T1 cells. The concentration used for the oxaliplatin control as well as for complex 3-6 was 10 μM.
Figure 9:
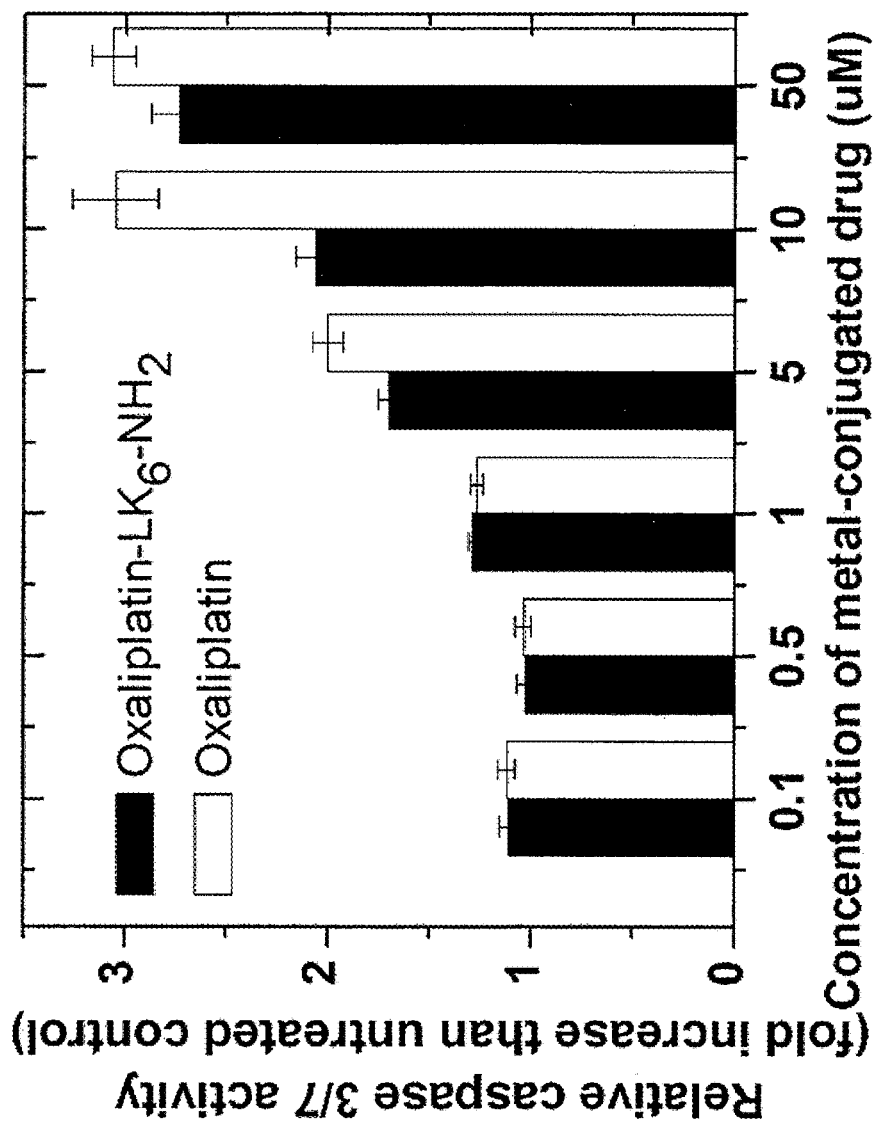
FIG. 9. Effect of concentration on caspase 3/7 activity using different concentrations of complex 3 in comparison to oxaliplatin. Luminescence reading was taken after 72 h of drug exposure.
Figure 10:
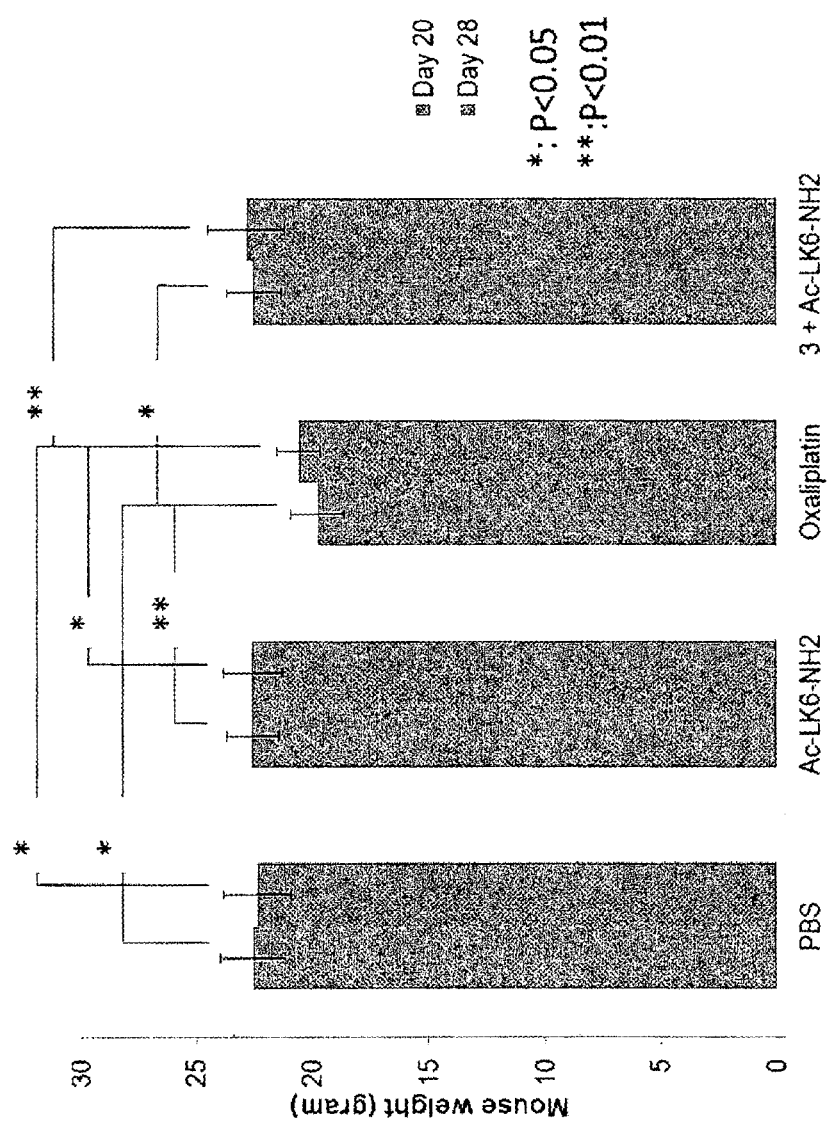
FIG. 10. Weight comparison between all four groups on day 20 and day 28.

Experiments have been performed to illustrate the technical aspects of exemplary embodiments of the present invention. The following examples are described in the Experimental Methods and Results. The skilled artisan will readily recognize that the examples are intended to be illustrative and are not intended to limit the scope of the present invention.

Experimental Methods

All reagents and solvents were obtained from commercial suppliers, and used as received. The starting compounds (SP-4-2)-diamminediiodoplatinum(II), (SP-4-2)-(trans-(R, R)-1,2-diaminocyclohexane)diiodoplatinum(II), and dimethyl-2-(3-bromopropyl)-2-methylmalonate were synthesized according to standard literature procedures (J.-M. Lehn, Science, 295, 2400-2403, 2002; G. M. Whitesides, B. Grzybowski, *Science* 2002, 295, 2418-2421). (SP-4-2)-(trans-(R,R)-1,2-diaminocyclohexane) diiodoplatinum(II) was synthesized using a method similar to the one described for (SP-4-2)-diamminediiodoplatinum(II); using 1R,2R-DACH instead of ammonia as the ligand. All peptide based compounds were purified on an Agilent 1260 Infinity preparative HPLC system equipped with a Zorbax SB-C18 column (21.2×150 mm 7 μM). The HPLC was coupled over an active splitter to a SQ-MS for mass triggered fraction collection. MilliQ water and HPLC grade acetonitrile, both containing 0.1% formic acid, were used as eluents. $^1$H and $^{13}$C NMR spectra were recorded on a Bruker AV-400 (400 MHz) instrument and all signals were referenced to the solvent residual peak.

1. Peptide Synthesis

The solid phase peptide synthesis of IVD-OH (SEQ IDN O: 58) and LIVAGD-OH (SEQ ID NO. 13) commenced with Fmoc-Asp(O$^t$Bu)-functionalised Wang resin (GL Biochem) and the SPPS of LIVAGKK-NH$_2$ (SEQ ID NO. 57) commenced with Fmoc-Lys(Boc)-functionalised Rink amide resin (GL Biochem) following standard peptide synthesis protocols (C. A. E. Hauser, R. Deng, A. Mishra, Y. Loo, U. Khoe, F. Zhuang, D. W. Cheong, A. Accardo, M. B. Sullivan, C. Riekel, J. Y. Ying, U. A. Hauser, *Proceedings of the National Academy of Sciences* 2011, 108, 1361-1366; A. Lakshmanan, C. A. E. Hauser, *International Journal of Molecular Sciences* 2011, 12, 5736-5746; A. Mishra, Y. Loo, R. Deng, Y. J. Chuah, H. T. Hee, J. Y. Ying, C. A. E. Hauser, *Nano Today* 2011, 6, 232-239). The de-protection of Fmoc was achieved by treating the resin with piperidine in DMF. The supernatant was filtered off and the resin washed with DMF. Coupling of the appropriate Fmoc-protected amino acid to the resin was done by treating the resin with a combined solution of the amino acid (3 equivalent), TBTU (3 equivalent) and DIPEA (3 equivalent) in DMF. The filtering-cum-washing, de-protection, and coupling cycle was then repeated until all the amino acids of the peptide were linked. In the final step, coupling of an alkyne group to the N-terminus was achieved by treating the resin with a combined solution of propiolic acid (2 equivalent) and HATU (2 equivalent) in DMF without the addition of DIPEA. After coupling, the resin was washed with a 10 wt % solution of DIPEA in DMF.[4] The final coupling step was repeated until the Kaiser test showed negative. After final washing of the resin with DMF and $CH_2Cl_2$, the resin was dried in vacuum. Subsequently, the N-propiolyl-peptide was cleaved from the resin by treating it with TFA. This step removed the $O^tBu$ protecting groups on Asp and Lys as well. The N-propiolyl-peptide was then precipitated from TFA by the addition of diethyl ether. After filtration, the N-propiolyl-peptide was further purified by HPLC.

Peptide P1: Yield: 384 mg (from 2 g of K(Boc)-Rink amide resin)

$^1$H-NMR ($d_6$-DMSO): 8.92 (1H, d, $^3J_{HH}$=8.1 Hz), 8.16 (1H, t, $^3J_{HH}$=5.5 Hz), 8.04 (1H, d, $^3J_{HH}$=6.7 Hz), 7.97 (1H, d, $^3J_{HH}$=8.7 Hz, NH), 7.89 (1H, d, $^3J_{HH}$=8.1 Hz, NH), 7.82 (1H, d, $^3J_{HH}$=8.7 Hz, NH), 7.37 (1H, s), 7.08 (1H, s), 4.39-4.31 (m, 1H), 4.29-4.22 (m, 1H), 4.21-4.10 (m, 5H), 3.72 (d, 2H, $^3J_{HH}$=5.6 Hz), 2.74 (t, 2H, $^3J_{HH}$=7.4 Hz), 2.54 (s, 1H), 2.00-1.90 (m, 1H), 1.77-1.62 (m, 3H), 1.61-1.33 (m, 7H), 1.32-1.24 (m, 2H), 1.20 (d, 3H, $^3J_{HH}$=6.9 Hz), 1.11-0.98 (m, 2H), 0.90-0.74 (m, 16H) ppm.

$^{13}$C-NMR ($d_6$-DMSO): 173.5, 172.5, 171.2, 171.0, 170.6, 168.6, 151.5, 78.2, 76.4, 57.6, 56.9, 52.1, 51.5, 48.4, 42.1, 40.4, 38.8, 36.3, 31.3, 30.4, 26.9, 24.4, 24.3, 23.0, 22.4, 21.5, 19.2, 18.1, 15.3, 11.0 ppm.

FT-IR: $\nu$=1211 (w), 1507 (m), 1600 (s), 2104 (vw), 2944 (vw), 3277 (w) cm$^{-1}$.

ESI-MS: Calculated for $C_{31}H_{55}N_8O_7$ ([M+H$^+$]$^+$) 651.42, Found: m/z 651.5.

Peptide P2: Yield: 107.2 mg (from 1 g of D(Boc)-Wang resin)

$^1$H NMR (95% $H_2O$/5% $D_2O$): 8.94 (d, 1H, J=5.8 Hz), 8.34 (d, 1H, J=4.6 Hz), 8.30-8.17 (m, 4H), 7.96 (d, 1H, J=8.0 Hz), 4.40-4.32 (m, 1H), 4.29-4.19 (m, 1H), 4.14-4.06 (m, 1H), 4.05-3.97 (m, 1H), 3.85 (d, 2H, J=5.9 Hz), 3.41 (s, 1H), 2.75 (m, 2H), 1.99-1.89 (m, 1H), 1.79-1.69 (m, 1H), 1.55-1.44 (m, 3H), 1.43-1.34 (m, 1H), 1.30 (d, 3H, J=7.4 Hz), 1.16-1.03 (m, 1H), 0.86-0.70 (m, 18H) ppm.

$^{13}$C NMR (95% $H_2O$/5% $D_2O$): 175.24, 173.78, 173.43, 172.90, 170.66, 167.93, 154.32, 77.37, 75.60, 59.22, 58.07, 53.03, 50.64, 49.93, 42.49, 39.57, 38.77, 36.83, 35.67, 30.28, 24.43, 24.34, 21.87, 21.07, 18.41, 17.70, 16.64, 14.69, 9.65 ppm.

FT-IR: $\nu$=1252 (m), 1501 (m), 1524 (s), 1597 (vs), 2100 (w), 2986 (w), 3256 (m) cm$^{-1}$.

ESI-MS: Calculated for $C_{29}H_{47}N_6O_{10}$ ([M+H$^+$]$^+$) 639.33, Found: m/z 639.4.

Peptide P3: Yield: 103 mg (from 2 g of D(Boc)-Wang resin)

$^1$H-NMR ($d_6$-DMSO): 12.54 (bs, 2H, COOH), 8.85 (d, 1H, $^3J_{HH}$=8.6 Hz), 8.20 (d, 1H, 8.2 Hz), 7.83 (d, 1H, 8.6 Hz), 4.51 (m, 1H), 4.19 (m, 1H), 4.15 (s, 1H), 2.67 (m, 1H), 2.56 (m, 1H), 1.96 (m, 1H), 1.74 (m, 1H), 1.40 (m, 1H), 1.10 (m, 1H), 0.82 (m, 12H) ppm.

$^{13}$C-NMR ($d_6$-DMSO): 172.2, 171.5, 170.4, 170.1, 151.5, 78.1, 76.3, 57.4, 57.3, 48.5, 35.9, 35.7, 30.7, 24.5, 19.0, 17.9, 15.2, 10.6 ppm.

FT-IR: $\nu$=1232 (w), 1401 (m), 1503 (s), 1575 (s), 1611 (m), 2102 (vw), 2977 (vw), 3261 (m) cm$^{-1}$.

ESI-MS: Calculated for $C_{18}H_{28}N_3O_7$ ([M+H$^+$]$^+$) 398.19, Found: m/z 398.3.

Peptide P4: Yield: 86.8 mg (from 2 g of K(Boc)-Rink amide resin)

$^1$H NMR (95% $H_2O$/5% $D_2O$): 8.37 (d, 1H, J=7.2 Hz), 8.26 (d, 1H, J=7.2 Hz), 7.49 (s, 1H), 7.01 (s, 1H), 4.22-4.13 (m, 1H), 4.10-4.05 (m, 1H), 4.00 (t, 2H, J=8.7 Hz), 3.43 (s, 1H), 2.89 (t, 2H, J=6.8 Hz), 1.99-1.88 (m, 1H), 1.78-1.52 (m, 5H), 1.45-1.24 (m, 3H), 1.15-1.03 (m, 1H), 0.88-0.72 (m, 12H) ppm.

$^{13}$C NMR (95% $H_2O$/5% $D_2O$): 176.31, 173.25, 173.08, 154.51, 77.41, 75.55, 59.69, 59.13, 53.47, 39.47, 35.99, 30.49, 30.09, 26.45, 24.75, 22.16, 18.44, 17.96, 14.72, 10.19 ppm.

FT-IR: $\nu$=194 (m), 1224 (m), 1501 (m), 1524 (s), 1577 (s), 2100 (vw), 3256 (m) cm$^{-1}$.

ESI-MS: Calculated for $C_{20}H_{36}N_5O_4$ ([M+H$^+$]$^+$) 410.6, Found: m/z 410.2.

2-(3-azidopropyl)-2-methylmalonic acid

Dimethyl 2-(3-bromopropyl)-2-methylmalonate (10.6 g, 39.7 mmol) was dissolved in 80 mL of a 6:1 mixture of acetone/water and solid $NaN_3$ (4.4 g, 67.7 mmol) was added. The resulting suspension was stirred under reflux overnight. Subsequently, the acetone was removed under reduced pressure and the resulting solution was extracted three times with EtOAc. The combined organic layer was dried over $MgSO_4$ filtered and the solvent removed under reduced pressure. The crude product so obtained was immediately dissolved in a mixture of $THF/H_2O$ (1:1) and 3 equivalent NaOH was added. The suspension was stirred at 40° C. overnight and the resulting solution was extracted three times with DCM. Subsequently, the pH of the aqueous phase was adjusted to 1 using a 12M HCl solution. After three rounds of extraction with EtOAc, the combined organic layer was dried over $MgSO_4$ filtered and the solvent was removed under reduced pressure. The title compound was obtained in sufficient purity as a white powder after vacuum drying. Yield: 4.5 g (56%, overall yield)

$^1$H NMR (95% $H_2O$/5% $D_2O$): 3.20 (t, 3H, J=6.6 Hz, $CH_2N_3$), 1.80-1.74 (m, 2H, $CH_2CH_2CH_2N_3$), 1.48-1.39 (m, 2H, $CH_2CH_2N_3$), 1.27 (s, 3H) ppm.

$^{13}$C NMR (95% $H_2O$/5% $D_2O$): 177.36 ($CO_2H$), 53.45 (C(CH2)), 50.92 ($CH_2N_3$), 32.83 ($CH_2CH_2N_3$), 23.62 ($CH_2CH_2N_3$), 19.94 ($CH_3$) ppm.

ESI-MS: Calculated for $C_7H_{11}N_3O_4Na$ ([M+Na$^+$]$^+$) 224.06, Found: m/z 224.1.

(SP-4-2)-Diammino-(2-(3-azidopropyl)-2-methyl-propanedioato-$\kappa O^1$,$\kappa O^3$)-platinum(II)

[PtI2(NH$_3$)$_2$] (250 mg; 0.518 mmol) was suspended in 10 ml of water. After addition of AgNO3 (171 mg; 1.01 mmol) the suspension was stirred overnight in the dark at room temperature. AgI was filtered off, and the filtrate was added to a solution of 2-(3-azidopropyl)-2-methylmalonic acid (102 mg; 0.505 mmol) and 1.0 M NaOH (0.505 ml; 0.505 mmol) in 5 ml of water. The resulting solution was stirred for 10 minutes after which a white solid started to precipitate. The solid was filtered off, washed with water and dried in vacuum. The solid was re-suspended in slightly cool/minimally cooled water, filtered and washed with water.

Yield: 102 mg (47%)

ESI-MS (positive): m/z 430.1 [M+H$^+$]$^+$, 469.2 [M+K$^+$]$^+$ (SP-4-2)-(2-(3-azidopropyl)-2-methylpropanedioato-κO$^1$,κO$^3$)-(trans-(R,R)-1,2-diaminocyclohexane) platinum(II)

[PtI$_2$(DACH)] (1 g; 1.78 mmol) was suspended in 50 ml of water. After addition of AgNO$_3$ (589 mg; 3.47 mmol) the suspension was stirred overnight in the dark at room temperature. AgI was filtered off and the filtrate was added to a solution of 2-(3-azidopropyl)-2-methylmalonic acid (349 mg; 1.74 mmol) and 1.0M NaOH (3.6 ml; 3.6 mmol) in ca. 10 ml of water. The resulting solution was stirred for 1 h at room temperature. Subsequently the solvent was removed, the residual solid was suspended in a minimal amount of water and stored in the fridge overnight, the product was filtered off, washed with water (three times), and dried in vacuum. Alternatively, the pure product can be obtained by preparative HPLC of the supernatant solution.

Yield: 351 mg (40%).

$^1$H NMR (95% H$_2$O/5% D$_2$O): 5.75 (bs, NH$_2$), 3.45 (m, 2H), 3.05 (m, 1H), 2.79 (m, 1H), 2.40 (bs, 2H), 2.05 (m, 2H), 1.61 (m, 4H), 1.40-1.08 (m, 7H) ppm.

$^{13}$C NMR (95% H$_2$O/5% D$_2$O): 181.9, 62.8, 57.0, 51.1, 36.4, 31.8, 24.0, 20.9 ppm.

FT-IR: ν=1493 (s), 1601 (m), 2094 (w) cm$^{-1}$.

ESI-MS: Calculated for C$_{13}$H$_{24}$N$_5$O$_4$Pt ([M+H$^+$]$^+$) 509.15, Found: m/z 509.2.

2. Peptide Ligation Reaction:

General Procedure 1:

An equimolar amount of peptide and metal compound was suspended in a 1:1 mixture of MilliQ water and tBuOH. To increase the solubility about 10% DMF was added. Subsequently 10 mol % of sodium ascorbate dissolved in a minimum of water was added followed by 1 mol % CuSO4.5H2O dissolved water. The resulting suspension was stirred in the dark overnight and purified directly by preparative HPLC.

General Procedure 2:

An equimolar amount of peptide and metal compound was suspended in DMF and 5 mol % CuBr was added. The resulting solution was stirred in the dark overnight. The solution was centrifuged to remove insoluble side products and purification was performed directly on a preparative HPLC system.

Compound 3: Yield: 49 mg (29%).

$^1$H NMR (95% H$_2$O/5% D$_2$O): 8.50 (d, 1H, J=6.7 Hz), 8.39 (s, 1H), 8.34 (d, 1H, J=5.5 Hz), 8.31-8.22 (m, 2H), 8.18 (d, 1H, J=8.5 Hz). 8.09 (d, 1H, J=7.8 Hz), 7.54 (s, 1H), 7.00 (s, 1H), 5.66-5.37 (m, NH$_2$), 4.51-4.35 (m, 2H), 4.24-4.08 (m, 2H) 4.07-3.88 (m, 2H), 3.79 (d, 2H, J=5.6 Hz), 3.54 (s, 3H), 2.91-2.68 (m, 3H), 2.57-2.43 (m, 1H), 2.31-2.13 (m, 1H), 2.09-1.94 (m, 1H), 1.93-0.89 (m, 29H), 0.88-0.60 (m, 18H).

$^{13}$C NMR (95% H$_2$O/5% D$_2$O): 181.2, 181.0, 176.6, 175.4, 174.2, 173.4, 172.9, 171.3, 161.7, 141.5, 127.4, 62.8, 62.3, 59.2, 58.2, 56.4, 53.2, 52.7, 50.6, 49.9, 42.4, 40.1, 39.4, 35.7, 35.5, 31.7, 30.3, 30.1, 26.2, 25.1, 24.6, 24.3, 23.9, 23.8, 22.0, 21.8, 21.2, 20.7, 18.3, 17.7, 16.4, 14.6, 9.7 ppm.

FT-IR: ν=1395 (m), 1414 (m), 1481 (s), 1512 (s), 2951 (w), 3280 (w) cm$^{-1}$.

ESI-MS: Calculated for C$_{44}$H$_{78}$N$_{13}$O$_{11}$Pt ([M+H$^+$]$^+$) 1159.59, Found: m/z 1159.6.

Compound 4: Yield: 3 mg (4.4%).

$^1$H NMR (95% H$_2$O/5% D$_2$O): 8.50 (d, 1H, J=6.3 Hz), 8.39 (s, 1H), 8.33 (d, J=5.7 Hz), 8.29-8.23 (m, 2H), 8.18 (d, 1H, J=8.4 Hz), 7.91 (d, 1H, J=7.8 Hz), 5.60-5.35 (m, NH$_2$), 4.48-4.37 (m, 2H), 4.17 (t, 1H, J=6.3 Hz), 4.04 (t, 1H, J=8.5 Hz), 3.95 (t, 1H, J=8.3 Hz), 3.80 (d, 1H, J=5.8 Hz), 2.80-2.70 (m, 2H), 2.73 (d, 1H, J=6.0 Hz), 2.68 (t, 1H, J=5.7 Hz), 2.56 (s, 3H), 2.55-2.44 (m, 1H), 2.06-0.91 (m, 21H), 0.83-0.63 (m, 20H) ppm.

$^{13}$C NMR (95% H$_2$O/5% D$_2$O): 181.6, 181.1, 175.2, 174.1, 173.3, 172.8, 170.5, 161.7, 141.5, 127.5, 62.9, 62.3, 59.2, 58.3, 56.4, 52.7, 50.3, 50.7, 49.9, 44.8, 42.5, 40.1, 38.7, 37.0, 35.8, 35.6, 31.8, 30.2, 25.1, 24.6, 24.4, 24.0, 21.85, 21.3, 20.7, 18.4, 17.6, 16.6, 14.6, 9.80 ppm.

FT-IR: ν=1201 (m), 1425 (m), 1502 (m), 1611 (s) cm$^{-1}$.

ESI-MS: Calculated for C$_{42}$H$_{70}$N$_{11}$O$_{14}$Pt ([M+H$^+$]$^+$) 1147, Found: m/z 1147.1.

Compound 5: Yield: 11 mg (24%).

$^1$H NMR (95% H$_2$O/5% D$_2$O): 8.40 (s, 1H), 8.36 (d, 1H, J=7.7 Hz), 8.29 (t, 2H, J=7.7 Hz), 5.66-5.35 (m, NH$_2$), 4.47 (m, 1H), 4.24 (t, 1H, J=7.7 Hz), 4.00 (t, 1H, J=8.1 Hz), 2.83-2.66 (m, 3H), 2.59-2.46 (m, 1H), 2.29-2.11 (m, 1H), 2.07-1.66 (m, 7H), 1.51-1.33 (m, 4H), 1.27-0.92 (m, 8H), 0.89-0.62 (m, 14H) ppm.

$^{13}$C NMR (95% H$_2$O/5% D$_2$O): 181.3, 181.1, 174.8, 173.2, 172.6, 161.8, 141.5, 127.4, 62.8, 62.3, 59.5, 58.5, 56.4, 50.6, 50.0, 36.5, 36.2, 35.6, 31.7, 30.1, 25.0, 24.8, 23.9, 23.8, 20.6, 18.2, 17.8, 14.7, 10.1 ppm.

FT-IR: ν=1394 (m), 1411 (m), 1501 (s), 1515 (s), 2960 (w), 3270 (w) cm$^{-1}$. ESI-

MS: Calculated for C$_{31}$H$_{51}$N$_8$O$_{11}$Pt ([M+H$^+$]$^+$) 906.33, Found: m/z 906.3.

Compound 6: Yield: 12 mg (22.1%).

$^1$H NMR (95% H$_2$O/5% D$_2$O): 8.39 (s, 1H), 8.35 (d, 1H, J=7.9 Hz), 8.28 (s, 1H), 7.48 (s, 1H), 6.99 (s, 1H), 5.63-5.38 (m, NH$_2$), 4.23 (t, 1H, J=8.1 Hz), 4.16-4.08 (m, 1H), 3.95 (t, 1H, J=8.1 Hz), 2.89-2.78 (m, 2H), 2.76-2.66 (m, 1H), 2.54-2.43 (m, 1H), 2.28-2.13 (m, 1H), 2.07-0.93 (m, 24H), 0.88-0.64 (m, 14H) ppm.

$^{13}$C NMR (95% H$_2$O/5% D$_2$O): 181.35, 181.09, 176.23, 173.33, 173.23, 161.94, 141.53, 127.39, 62.83, 62.33, 59.65, 58.47, 56.40, 53.37, 50.63, 39.35, 36.46, 35.56, 31.77, 30.34, 29.96, 29.57, 26.34, 25.09, 24.81, 23.91, 23.81, 22.03, 20.75, 18.24, 17.95, 14.66, 10.15 ppm.

FT-IR: ν=1392 (m), 1413 (m), 1583 (s), 1608 (s) cm$^{-1}$.

ESI-MS: Calculated for C$_{33}$H$_{59}$N$_{10}$O$_8$Pt ([M+H$^+$]$^+$) 918, Found: m/z 918.2.

Complex 7: Yield: 29 (25%)

$^1$H NMR (95% H$_2$O/5% D$_2$O): 8.72-8.00 (m, 7H), 7.55 (s, 1H), 7.00 (s, 1H), 4.50-3.70 (m, 12H), 2.83 (s, 2H), 2.63-2.45 (m, 1H), 2.00-0.93 (m, 23H), 0.92-0.46 (m, 20H)

$^{13}$C NMR (95% H$_2$O/5% D$_2$O): 181.4, 181.3, 176.1, 175.4, 174.5, 173.4, 172.9, 171.3, 162.0, 141.5, 127.4, 59.2, 58.2, 56.5, 53.2, 52.7, 50.4, 49.9, 42.4, 39.7, 39.4, 35.6, 35.4, 30.3, 30.1, 26.2, 25.3, 24.5, 24.3, 22.0, 21.9, 21.0, 20.7, 18.3, 17.7, 16.4, 14.6, 9.7 ppm.

Complex 8: Yield: 28 (67%)

$^1$H NMR (95% H$_2$O/5% D$_2$O): 8.48-8.40 (m, 2H), 8.32 (d, 1H, J=8.5 Hz), 8.16 (d, 1H, J=7.5 Hz), 4.50-4.3.5 (m, 3H), 4.20 (t, 1H, J=7.7 Hz), 4.06-3.83 (m, 6H), 2.78-2.45 (m, 4H), 1.99-1.87 (m, 1H), 1.86-1.71 (m, 4H), 1.47-1.35 (m, 1H), 1.33-1.20 (m, 1H), 1.14 (s, 3H), 0.84-0.62 (m, 12H)

$^{13}$C NMR (95% H$_2$O/5% D$_2$O): 181.4, 181.3, 173.4, 172.4, 162.0, 141.6, 127.4, 59.5, 58.9, 56.5, 50.5, 36.0, 35.4, 30.0, 25.2, 24.8, 20.5, 18.3, 17.7, 14.7, 10.0 ppm.

NMR Assignment for Compounds 3 and 5
$^{1}$H and $^{13}$C Chemical Shifts for Compound 2 (1 mM in d$_{7}$-DMF):
Peptide Moiety:

|  | C' | Cα | Cβ | Cγ$_1$ | Cγ$_2$ | Cδ | Cε | H | Hα | Hβ | Hγ$_1$ | Hγ$_2$ | Hδ |
|---|---|---|---|---|---|---|---|---|---|---|---|---|---|
| Leu | 169.2 | 58.7 | 41.8 | 23.1 |  | 18.1 |  | 7.8 | 4.3 | 1.7, 1.8 | 1.4 |  | 0.9 |
| Ile | 172.6 | 58.2 | 36.9 | 23.9 | 19.3 | 10.8 |  | 8.3 | 4.4 | 1.9 | 1.4 | 0.9 | 0.8 |
| Val | 171.9 | 58.8 | 31.6 | 21.6 |  |  |  | 8 | 4.3 | 2.1 | 0.9 |  |  |
| Ala | 173.4 | 49.8 | 17.5 |  |  |  |  | 8.2 | 4.3 | 1.4 |  |  |  |
| Gly | 169.2 | 43.0 |  |  |  |  |  | 8.4 | 3.9, 3.8 |  |  |  |  |
| Lys |  | 52.0 |  |  |  | 29.7 |  | 8.4 | 4.8 | 1.7 |  | 1.8 |  |

1R,2R-DACH and the Linker:

|  | C12 | C36 | C45 | H12 | H361 | H362 | H451 | H452 | NH1 | NH2 |
|---|---|---|---|---|---|---|---|---|---|---|
| DACH | 50.6 | 32 | 32.1 | 4.6 | 1.7 | 1.8 | 1.3 | 1.9 | 5.3 | 6.1 |

|  | C4 | C5 | C7 | C$_{Az1}$ | CO | H4 | H5 | H$_{Az1}$ | H7 |
|---|---|---|---|---|---|---|---|---|---|
| linker | 30.8 | 24.7 | 17.3 | 126.9 | 178.4 | 2.1 | 1.6 | 7.8 | 1.4 |

$^{1}$H and $^{13}$C Chemical Shifts for Compound 4 (3 mM in d$_{7}$-DMF):
Peptide Moiety

|  | C' | Cα | Cβ | Cγ$_1$ | Cγ$_2$ | Cδ | Cε | H | Hα | Hβ | Hγ$_1$ | Hγ$_2$ | Hδ |
|---|---|---|---|---|---|---|---|---|---|---|---|---|---|
| Ile | 171.1 | 57 | 38.2 | 24.7 | 15.4 | 10.8 |  | 8.1 | 4.6 | 1.9 | 1.1 | 0.8 | 0.7 |
| Val | 171.2 | 58.3 | 30.9 | 19 | 17.6 |  |  | 8.3 | 4.3 | 2.0 | 0.8 | 0.7 |  |
| Asp | 171.3 | 57.1 | 38 |  |  |  |  | 8.0 | 4.5 | 2.6 |  |  |  |

For 1R,2R-DACH and the Linker

|  | C12 | C36 | C45 | H12 | H361 | H362 | H451 | H452 | NH1 | NH2 |
|---|---|---|---|---|---|---|---|---|---|---|
| DACH | 50.6 | 32.2 | 32.1 | 4.4 | 1.3 | 1.9 | 1.4 | 1.9 | 5.3 | 6.1 |

|  | C4 | C5 | C7 | C$_{Az1}$ | CO | H4 | H5 | H$_{Az1}$ | H7 |
|---|---|---|---|---|---|---|---|---|---|
| linker | 35.8 | 24.4 | 17.3 | 126.9 | 178.4 | 2.1 | 1.6 | 7.8 | 1.2 |

FESEM:

Hydrogel samples were shock frozen and kept at −80° C. Frozen samples were then freeze-dried. Lyophilized samples were fixed onto a sample holder using a carbon conductive tape and sputtered with platinum from both the top and the sides in a JEOL JFC-1600 High Resolution Sputter Coater. The coating current was 20 mA and the process lasted for 50 sec. The surface of interest was then examined with a JEOL JSM-7400F Field Emission Scanning Electron Microscopy (FESEM) system using an accelerating voltage of 2 kV.

3. Drug Release Study

All drug release studies were carried out in 24-well transwell plates (Corning Transwell® 6.5 mm, 8.0 μM with a polycarbonate membrane insert) using 100 μL of gel in the transwell and 400 μL of DMEM in the peripheral well.

Drug Release Study in the Presence of Cells

HeLa cells (3500 cells/transwell) were seeded onto 24-well transwell plates in 100 μL DMEM supplemented with 10% FBS and 1% Pen-strep (growth medium). 400 μL of the growth medium was added to the peripheral well, giving a total volume of 500 μL. The cells were incubated overnight after which all the medium was removed. 100 μL of Ac-LIVAGK-NH$_2$ (SEQ ID NO. 16 acylated and amidated) gel (15 mg/mL in 1×PBS) containing either 45 μM of compound 2, 45 μM of oxaliplatin or no drug, was added on top of the cells in the transwell and 400 μL of the growth medium was added to the peripheral well. The release of platinum was studied by sampling 400 μL of medium at 1 h, 2 h, 4 h, 8 h, 1 d, 2 d, 3 d, and 4 d. Each time the hydrogel was untouched and only the medium surrounding the transwell was replenished. At the end of the release study, the residual gels were dissolved in 400 μL MilliQ water to determine the total drug concentration.

Figure 12:
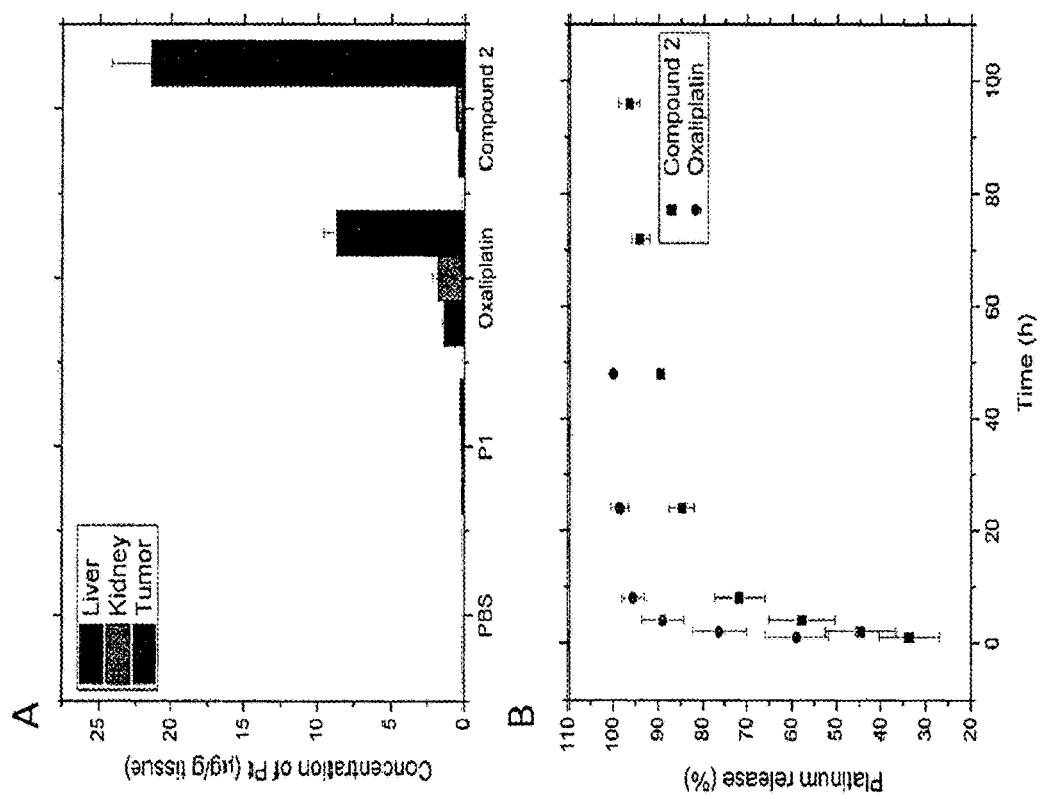
FIG. 12. Bio-distribution and drug release profiles
(A) Bio-distribution profiles of the injected compounds in the liver, kidney and tumor of the treated animals. (B) In vitro drug release profile of the oxaliplatin-peptide conjugate and the free drug, in the presence of HeLa cells cultured in a 24-well transwell plate. Platinum concentration was measured using ICP-MS. At least three triplicates were taken for each data point.

The concentration of released platinum was measured by inductively coupled plasma mass spectrometry (ICP-MS). See FIG. 12b.

Drug Release Study without Cells

Figure 11:
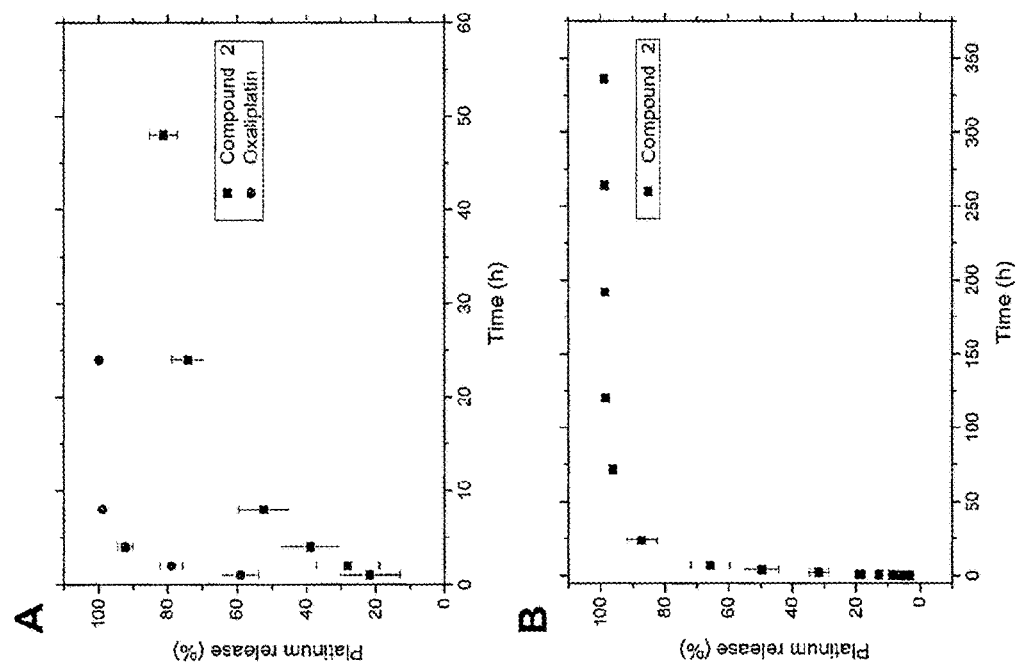
FIG. 11: Platinum release of compound 3 and oxaliplatin control over a period of two days (A) and of a hybrid hydrogel containing 10 wt % of compound 3 over a period of 14 days (B).

The experiment was conducted in the same way as described above; with the exception that no cells were seeded onto the transwells and the DMEM medium did not contain FBS and pen-strep. At the end of the release study, the residual gels were dissolved in 400 μL MilliQ water to determine the total drug concentration. Three replicates were used and ICP-MS measurements were performed to determine the amount of drug released at each time point. See FIG. 11a Long-Term Drug Release Study Long-term drug release studies were carried out in 24-well transwell plates at 37° C. using PBS buffer as the solvent system. For this purpose, three gels containing 10% of compound 2 and 90% of Ac-LIVAGK-NH$_2$ (SEQ ID NO. 16 acylated and amidated) (total concentration of 15 mg/mL) were independently prepared by completely dissolving compound 2 and the parent peptide in 90% of water and then adding 10×PBS, giving a 1×PBS solution. 100 μL of each gel was added to the transwell and 500 μL of PBS was added to the surrounding well. Samples were taken at different time points and the drug release was determined by inductively coupled plasma mass spectrometry (ICP-MS) analysis. At the end of the release study, the residual gels were dissolved in 500 μL PBS to determine the total drug concentration. See FIG. 11b Inductively Coupled Plasma Mass Spectrometry (ICP-MS) Analysis to Determine Platinum Concentration All ICP-MS analyses were performed on a Perkin Elmer Elan DRC II instrument and the $^{195}$Pt isotope was used for quantification.

All samples containing growth medium were digested with nitric acid (68% suprapur, Merck) in a 1:1 ratio by volume overnight, prior to ICP-MS analysis. All nitric acid containing samples were diluted to a suitable concentration for ICP-MS analysis. All other samples were measured without nitric acid treatment, and each sample was diluted depending on the platinum concentration. Calibration was conducted using an external standard (Sigma-Aldrich) between 1-200 ppb. The concentrations of the samples were calculated based on the calibration curve plotted using Elan software, and was used to calculate the accumulative release profile as a percentage.

4. Cell Culture.

Human cervical carcinoma cell line HeLa, human colon carcinoma cell line SW480 and mouse breast cancer cell line 4T1 were purchased from the American Type Culture Collection (Manassas, Va., USA). The cell lines were cultured in DME medium (Biopolis shared facilities, A*STAR, SG) supplemented with 10% heat inactivated fetal bovine serum and 1% of mixture of penicillin and streptomycin (Invitrogen, CA, U.S.A). The cells were maintained in a 75 mL cell culture flask (Nunc) at 37° C. in a humidified incubator with 95% air and 5% CO$_2$.

5. Cell Proliferation Assay

Cytotoxicity was determined by means of a colorimetric microculture assay (MTs assay, MTS=3-(4,5-Dimethylthiazol-2-yl)-2,5-diphenyltetrazolium bromide) For this purpose, HeLa, SW480, and 4T1 cells were harvested from culture flasks by trypsinization and seeded into 96-well microculture plates in cell densities of 3.5×10$^3$ cells/well. The cells were allowed to attach for 8 h. Subsequently, cells were exposed to serial dilutions of the test compounds in 150 μL/well complete culture medium for 96 h. Then 25 uL of CellTiter 96® Aqueous one solution reagent was added to the cells, followed by incubation for 2 h at 37° C. After incubation, the absorbance was measured at a wavelength of 499 nm using a microplate reader. The quantity of vital cells was expressed in terms of T/C values in comparison to untreated control microcultures, and 50% inhibitory concentrations (IC$_{50}$) were calculated from concentration-effect curves by a nonlinear curve fit using Origin Lab 7.5.

6. Cell Cycle Analysis:

Cells (3×10$^6$ cells) were seeded into 10 cm petridishes and allowed to recover for 24 h. The medium was exchanged to serum free DME medium and the cells were allowed to synchronize for 24 h. The medium was later changed to DME medium containing 10% heat inactivated fetal bovine serum and 1% of mixture of penicillin and streptomycin (Invitrogen, CA, U.S.A). Cells were exposed to 10 μM of the test compounds for 96 h. Control and treated cells were collected, washed with PBS, fixed in 70% ice-cold ethanol, and stored at −20° C. To determine cell cycle distributions, cells were transferred to a PBS solution, incubated with 10 μg/mL RNase A for 30 min at 37° C., and treated with 5 μg/mL propidium iodide for 30 min. Fluorescence of individual cells was measured by flow cytometry, 7. Caspase 3/7 Assay:

Caspase 3/7 activity in HeLa, SW480, and 4T1 cells was measured using a Caspase-Glo® 3/7 assay (Promega). In short, cells were plated in a white-walled 96-well as described for the cell proliferation assay. The cells were exposed to different concentrations of the test compounds for 24, 48, 72, and 96 h. Subsequently 100 μL of fresh medium was added followed by 100 μL Caspase-Glo® 3/7 Reagent. The resulting solution was mixed and incubated for 3 h. Luminescence reading was taken on a TECAN Infinite M200 96 well plate reader at 560 nm.

8. In Vivo Study to Evaluate Therapeutic Efficacy

Adult female Balb/c mice used in this study (weight 20 g; aged 6-8 weeks) were provided by Biological Resource Center (BRC), A*Star, Biopolis, Singapore. For tumor establishment, 1×10$^6$ mouse 4T1 breast cancer cells were injected subcutaneously into the flank of Balb/c mice (designated as day 0). To investigate the effect of the mixture of Oxaliplatin and hydrogel, the tumor-inoculated animals were divided into 4 groups (n=9 per group) on day 7 post-tumor inoculation and received an intratumor injection of sample solutions: phosphate buffered saline (PBS), Ac-LIVAGK-NH$_2$ (SEQ ID NO. 16 acylated and amidated) (12.5 mg/mL) oxaliplatin (15 mg/kg), 3 (44 mg/kg) and Ac-LIVAGK-NH$_2$ (SEQ ID NO. 16 acylated and amidated) (12.5 mg/mL). 100 μL of each sample were injected directly into the tumor. The hydrogels were prepared prior to injection by dissolving the peptide in 1×PBS and vortexing for 1 min. The sample containing 3 was prepared in a similar manner; 3 was dissolved in 1×PBS and the resulting solution was added to the peptide and vortexed for 1 min. A solid hydrogel was observed about 10 min after sample preparation, to allow in situ gelation inside the tumor.

Tumor volume was determined by measurement with an electronic digital vernier caliper. Readings were taken once a week until day 28 post-tumor inoculation. The ellipsoid volume of the tumor (mm$^3$) was then calculated using the formula: Volume=(Width)×(Length)×(height)×π/6.

All handling and care of animals was carried out in accordance with the Guidelines on the Care and Use of Animals for Scientific Purposes issued by the National Advisory Committee for Laboratory Animal Research, Singapore.

Data are represented as mean±SE. The statistical significance of differences was determined by the analysis of variance (ANOVA) with replication followed by Fisher's Least Significant Difference post hoc analysis. A P-value of <0.05 was considered to be statistically significant.

9. Measuring Platinum Content in Tumor and Organ Samples

Ammonia solution (25% suprapur) and nitric acid (68% suprapur) were purchased from Merck. H$_2$O$_2$ (30% (w/w) and the platinum standards were purchased from Sigma-Aldrich.

Liver, kidney and tumor tissues were cut into small pieces and rinsed in ice-cold PBS. The kidney, liver and tumor sections were accurately weighed and transferred into a glass vial and treated as described previously.[6] Briefly, these tissues were digested with 0.4 ml of nitric acid (68% (v/v) and 0.8 ml of $H_2O_2$ (30% (v/v). The mixture was placed in an 80° C. water bath for 1 h, to get sufficient digestion. While cooling, 0.4 ml of ammonia water (25-28% (v/v) was added to neutralize the excess acid, and the mixture was diluted to a final volume of 2.0 ml. After vortexing, the mixture was filtered using a 0.2 μm filter. 200 μl of the filtered samples were diluted to a final volume of 10 ml using Milli-Q water. The diluted samples were used for analyzing the platinum content by ICP-MS. All experiments were carried out on a Perkin Elmer Elan DRC II ICP-MS instrument. See FIG. 12a.

10. Statistical Evaluation

Tumor Volume

Day 7

| Group Name | N | Missing | Mean | Std Dev | SEM |
|---|---|---|---|---|---|
| PBS | 9 | 0 | 87.932 | 45.075 | 15.025 |
| Ac-LK6-NH2 | 9 | 0 | 52.556 | 32.184 | 10.728 |
| Oxaliplatin | 9 | 0 | 61.938 | 42.224 | 14.075 |
| 3 + Ac-LK6-NH2 | 9 | 0 | 84.641 | 45.924 | 15.308 |
| Source of Variation | DF | SS | MS | F | P |
| Between Groups | 3 | 8034.344 | 2678.115 | 1.539 | 0.223 |
| Residual | 32 | 55675.438 | 1739.857 | | |
| Total | 35 | 63709.782 | | | |

The differences in the mean values among the treatment groups are not great enough to exclude the possibility that the difference is due to random sampling variability; there is not a statistically significant difference (P = 0.223).
Power of performed test with alpha = 0.050:0.144
The power of the performed test (0.144) is below the desired power of 0.800.
Less than desired power indicates you are less likely to detect a difference when one actually exists.
Negative results should be interpreted cautiously.

LK6 is SEQ ID NO. 16

Day 14

| Group Name | N | Missing | Mean | Std Dev | SEM |
|---|---|---|---|---|---|
| PBS | 9 | 0 | 388.691 | 241.541 | 80.514 |
| Ac-LK6-NH2 | 9 | 0 | 236.319 | 90.924 | 30.308 |
| Oxaliplatin | 9 | 0 | 135.101 | 63.650 | 21.217 |
| 3 + Ac-LK6-NH2 | 9 | 0 | 163.451 | 100.345 | 33.448 |
| Source of Variation | DF | SS | MS | F | P |
| Between Groups | 3 | 347887.073 | 115962.358 | 5.746 | 0.003 |
| Residual | 32 | 645838.386 | 20182.450 | | |
| Total | 35 | 993725.459 | | | |

The differences in the mean values among the treatment groups are greater than would be expected by chance; there is a statistically significant difference (P = 0.003).
Power of performed test with alpha = 0.050:0.867
All Pairwise Multiple Comparison Procedures (Holm-Sidak method):
Overall significance level = 0.05

Comparisons for factor:

| Comparison | Diff of Means | t | Unadjusted P | Critical Level | Significant? |
|---|---|---|---|---|---|
| PBS vs. Oxaliplatin | 253.590 | 3.787 | 0.000635 | 0.009 | Yes |
| PBS vs. 3 + Ac-LK6-NH | 225.240 | 3.363 | 0.00201 | 0.010 | Yes |
| PBS vs. Ac-LK6-NH2 | 152.372 | 2.275 | 0.0297 | 0.013 | No |
| Ac-LK6-NH2 vs. Oxali | 101.218 | 1.511 | 0.141 | 0.017 | No |
| Ac-LK6-NH2 vs. 3 + Ac | 72.868 | 1.088 | 0.285 | 0.025 | No |
| 3 + Ac-LK6-NH2 vs. Ox | 28.350 | 0.423 | 0.675 | 0.050 | No |

LK6 is SEQ ID NO. 16

Day 21

| Group Name | N | Missing | Mean | Std Dev | SEM |
|---|---|---|---|---|---|
| PBS | 9 | 0 | 676.963 | 222.409 | 74.136 |
| LK6 | 9 | 0 | 583.982 | 196.922 | 65.641 |
| OXAL | 9 | 0 | 96.493 | 65.969 | 21.990 |
| OLK6 | 9 | 0 | 435.156 | 180.942 | 60.314 |
| Source of Variation | DF | SS | MS | F | P |
| Between Groups | 3 | 1751731.523 | 583910.508 | 18.635 | <0.001 |
| Residual | 32 | 1002688.947 | 31334.030 | | |
| Total | 35 | 2754420.470 | | | |

The differences in the mean values among the treatment groups are greater than would be expected by chance; there is a statistically significant difference (P = <0.001).
Power or performed test with alpha = 0.050:1.000
All Pairwise Multiple Comparison Procedures (Holm-Sidak method):
Overall significance level = 0.05

Comparisons for factor:

| Comparison | Diff of Means | t | Unadjusted P | Critical Level | Significant? |
|---|---|---|---|---|---|
| PBS vs. OXAL | 580.470 | 6.956 | 0.0000000704 | 0.009 | Yes |
| LK6 vs. OXAL | 487.488 | 5.842 | 0.00000172 | 0.010 | Yes |
| OLK6 vs. OXAL | 338.663 | 4.059 | 0.000297 | 0.013 | Yes |
| PBS vs. OKL6 | 241.807 | 2.898 | 0.00673 | 0.017 | Yes |
| LK6 vs. OKL6 | 148.825 | 1.784 | 0.0840 | 0.025 | No |
| PBS vs. LK6 | 92.982 | 1.114 | 0.273 | 0.050 | No |

LK6 is SEQ ID NO. 16

Day 28

| Group Name | N | Missing | Mean | Std Dev | SEM |
|---|---|---|---|---|---|
| PBS | 9 | 0 | 1106.266 | 446.815 | 148.938 |
| Ac-LK6-NH2 | 9 | 0 | 1400.703 | 570.088 | 190.029 |
| Oxaliplatin | 9 | 0 | 250.650 | 277.625 | 92.542 |
| 3 + Ac-LK6-NH2 | 9 | 0 | 700.723 | 378.256 | 126.085 |
| Source of Variation | DF | SS | MS | F | P |
| Between Groups | 3 | 6746391.610 | 2248797.203 | 12.077 | <0.001 |
| Residual | 32 | 5958379.127 | 186199.348 | | |
| Total | 35 | 12704770.737 | | | |

The differences in the mean values among the treatment groups are greater than would be expected by chance; there is a statistically significant difference (P = <0.001).
Power or performed test with alpha = 0.050:0.999
All Pairwise Multiple Comparison Procedures (Holm-Sidak method):
Overall significance level = 0.05

Comparisons for factor:

| Comparison | Diff of Means | t | Unadjusted P | Critical Level | Significant? |
|---|---|---|---|---|---|
| Ac-LK6-NH2 vs. Oxali | 1150.053 | 5.654 | 0.00000296 | 0.009 | Yes |
| PBS vs. Oxaliplatin | 855.616 | 4.206 | 0.000196 | 0.010 | Yes |

-continued

| | | | | | |
|---|---|---|---|---|---|
| Ac-LK6-NH2 vs. 3 + Ac | 699.980 | 3.441 | 0.00163 | 0.013 | Yes |
| 3 + Ac-LK6-NH2 vs. Ox | 450.073 | 2.213 | 0.0342 | 0.017 | No |
| PBS vs. 3 + Ac-LK6-NH | 405.543 | 1.994 | 0.0548 | 0.025 | No |
| Ac-LK6-NH2 vs. PBS | 294.437 | 1.447 | 0.157 | 0.050 | No |

LK6 is SEQ ID NO. 16
Statistical Evaluation
Day 20

| Group Name | N | Missing | Mean | Std Dev | SEM |
|---|---|---|---|---|---|
| PBS | 9 | 0 | 22.567 | 1.405 | 0.468 |
| Ac-LK6-NH2 | 9 | 0 | 22.586 | 1.118 | 0.373 |
| Oxaliplatin | 9 | 0 | 19.754 | 1.110 | 0.370 |
| 3 + Ac-Lk6-NH2 | 9 | 0 | 22.526 | 1.146 | 0.382 |

| Source of Variation | DF | SS | MS | F | P |
|---|---|---|---|---|---|
| Between Groups | 3 | 53.132 | 17.711 | 12.277 | <0.001 |
| Residual | 32 | 46.163 | 1.443 | | |
| Total | 35 | 99.294 | | | |

The differences in the mean values among the treatment groups are greater than would be expected by chance; there is a statistically significant difference (P = <0.001).
Power of performed test with alpha = 0.050:0.999
All Pairwise Multiple Comparison Procedures (Holm-Sidak method):
Overall significance level = 0.05

Comparisons for factor:

| Comparison | Diff of Means | t | Unadjusted P | Critical Level | Significant? |
|---|---|---|---|---|---|
| Ac-LK6-NH2 vs. Oxali | 2.831 | 5.000 | 0.0000199 | 0.009 | Yes |
| PBS vs Oxaliplatin | 2.813 | 4.967 | 0.0000218 | 0.010 | Yes |
| 3 + Ac-Lk6-NH2 vs. Oxa | 2.772 | 4.896 | 0.0000269 | 0.013 | Yes |
| Ac-Lk6-NH2 vs. 3 + Ac- | 0.0593 | 0.105 | 0.917 | 0.017 | No |
| PBS vs. 3 + Ac-Lk6-NH2 | 0.0407 | 0.0720 | 0.943 | 0.025 | No |
| Ac-LK6-NH2 vs. PBS | 0.0186 | 0.0328 | 0.974 | 0.050 | No |

LK6 is SEQ ID NO. 16
Day 28

| Group Name | N | Missing | Mean | Std Dev | SEM |
|---|---|---|---|---|---|
| PBS | 9 | 0 | 22.335 | 1.469 | 0.490 |
| Ac-LK6-NH2 | 9 | 0 | 22.576 | 1.252 | 0.417 |
| Oxaliplatin | 9 | 0 | 20.593 | 0.894 | 0.298 |
| 3 + Ac-LK6-NH2 | 9 | 0 | 22.820 | 1.657 | 0.552 |

| Source of Variation | DF | SS | MS | F | P |
|---|---|---|---|---|---|
| Between Groups | 3 | 27.615 | 9.205 | 5.065 | 0.006 |
| Residual | 32 | 58.152 | 1.817 | | |
| Total | 35 | 85.767 | | | |

The differences in the mean values among the treatment groups are greater than would be expected by chance; there is a statistically significant difference (P = 0.006).
Power of performed test with alpha = 0.050:0.801
All Pairwise Multiple Comparison Procedures (Holm-Sidak method):
Overall significance level = 0.05

Comparisons for factor:

| Comparison | Diff of Means | t | Unadjusted P | Critical Level | Significant? |
|---|---|---|---|---|---|
| 3 + Ac-LK6-NH2 vs. Oxa | 2.227 | 3.504 | 0.00138 | 0.009 | Yes |
| Ac-LK6-NH2 vs. Oxalip | 1.982 | 3.119 | 0.00382 | 0.010 | Yes |
| PBS vs. Oxaliplatin | 1.742 | 2.741 | 0.00995 | 0.013 | Yes |
| 3 + Ac-LK6-NH2 vs. PBS | 0.485 | 0.763 | 0.451 | 0.017 | No |
| 3 + Ac-LK6-NH2 vs. Ac- | 0.244 | 0.385 | 0.703 | 0.025 | No |
| Ac-LK6-NH2 vs. PBS | 0.241 | 0.379 | 0.708 | 0.050 | No |

LK6 is SEQ ID NO. 16

11. Synthesis of Catechol Peptide Analogs Through Click Chemistry

Materials and Methods:

The solid phase peptide synthesis of LIVAGKK-NH$_2$ (SEQ ID NO. 57 amidated) and AIVAGS-NH$_2$ (SEQ ID NO. 19 amidated) commenced with Fmoc-Lys(Boc)-functionalised Rink amide resin (GL Biochem) or Fmoc-Ser(tBu) Rink amide resin (GL Biochem) respectively following standard peptide synthesis protocols.[3] The de-protection of Fmoc was achieved by treating the resin with piperidine in DMF. The supernatant was filtered off and the resin washed with DMF. Coupling of the appropriate Fmoc-protected amino acid to the resin was done by treating the resin with a combined solution of the amino acid (3 equivalent), TBTU (3 equivalent) and DIPEA (3 equivalent) in DMF. The filtering-cum-washing, de-protection, and coupling cycle was then repeated until all the amino acids of the peptide were linked. In the final step, coupling of an alkyne group to the N-terminus was achieved by treating the resin with a combined solution of propiolic acid (2 equivalent) and HATU (2 equivalent) in DMF without the addition of DIPEA. After coupling, the resin was washed with a 10 wt % solution of DIPEA in DMF.[4] The final coupling step was repeated until the Kaiser test showed negative. After final washing of the resin with DMF and CH$_2$Cl$_2$, the resin was dried in vacuum. Subsequently, the N-propiolyl-peptide was cleaved from the resin by treating it with TFA. This step removed the O$^t$Bu protecting groups on Asp and Lys as well. The N-propiolyl-peptide was then precipitated from TFA by the addition of diethyl ether. After filtration, the N-propiolyl-peptide was further purified by HPLC.

Figure 15:
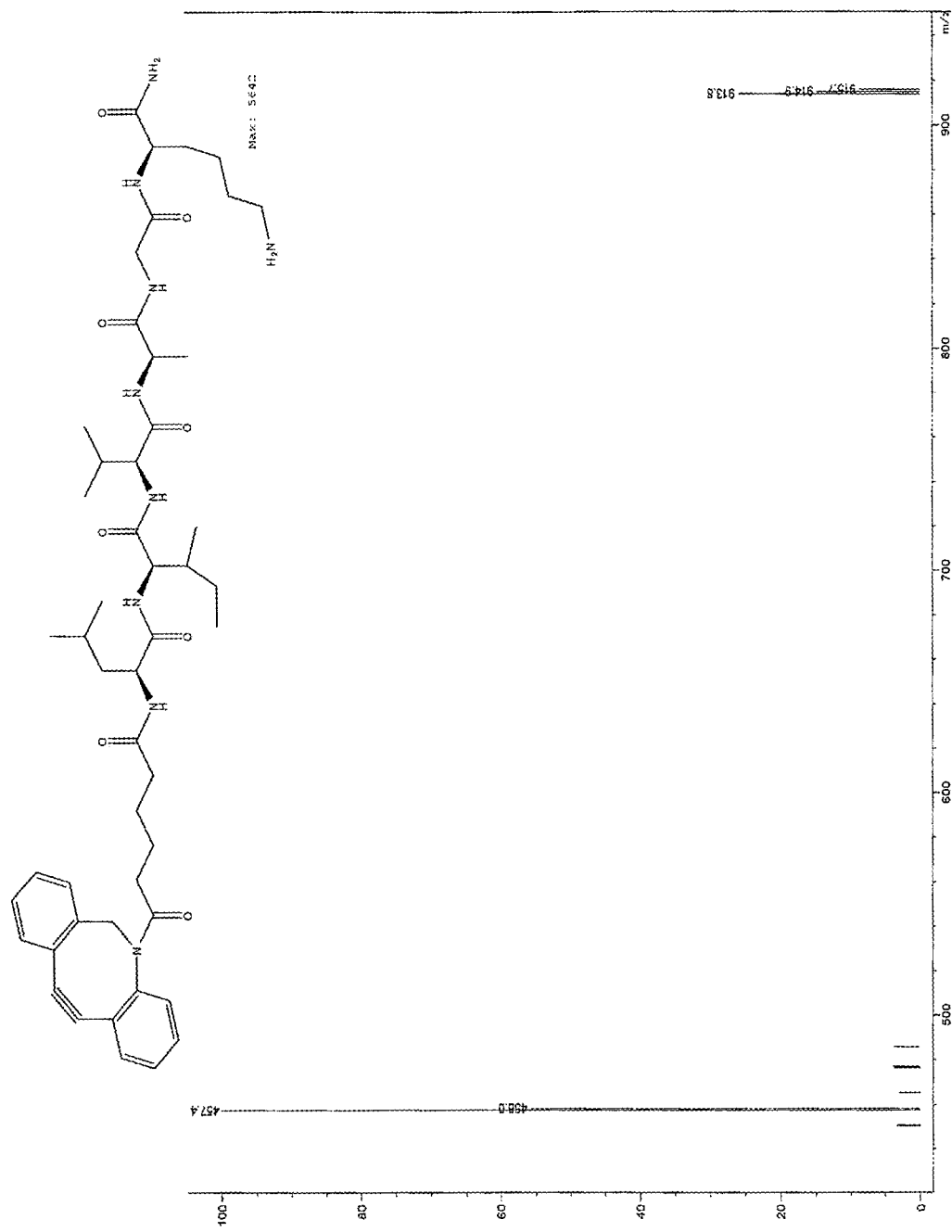
Figure 16:
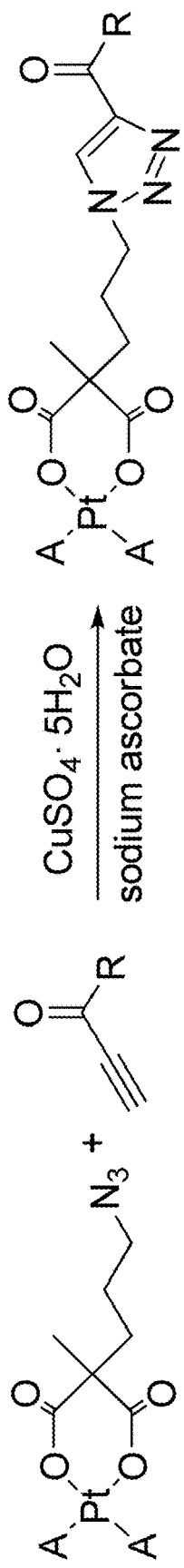
FIG. 16. Synthesis of platinum peptide conjugates.

DBCO-LK$_6$-NH$_2$:

The DBCO containing peptide (FIG. 15) was synthesized following standard peptide synthesis protocols.[3] DBCO-acid was coupled using TBTU, HOBt and DIPEA using 1.3 equivalent of DBCO-acid in respect to the resin loading. Cleaving and purification of the final compound was performed as reported above. Yield 22%

ESI-MS: Calculated for $C_{49}H_{72}N_9O_8$ ([M+H$^+$]$^+$) 914.55, Found: m/z 913.8.

Figure 13:
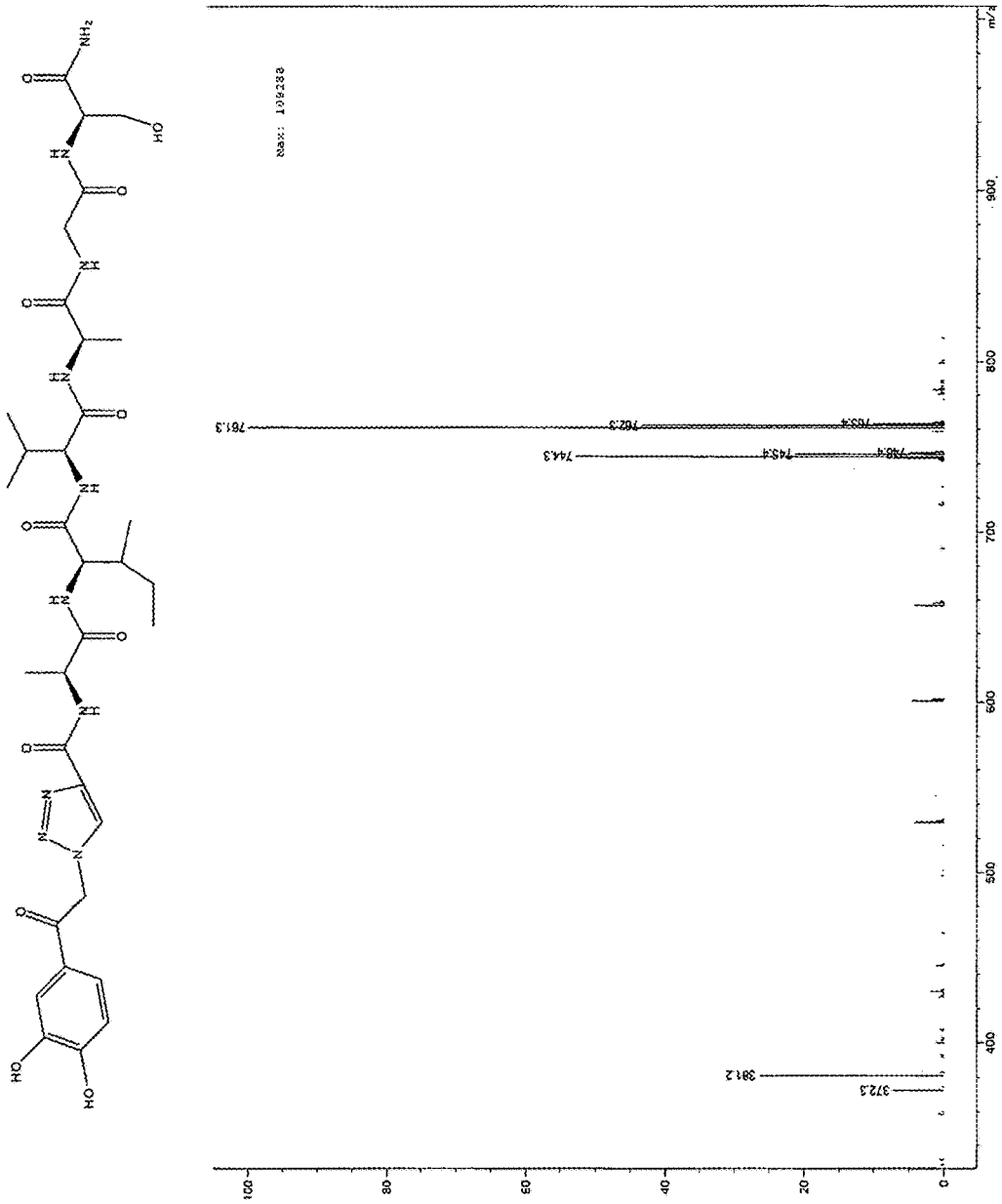
FIG. 13. Chemical structure and MS spectrum of a catechol -AIVAGS-NH$_2$ (SEQ ID NO. 19 amidated) analog FIG. 14. Chemical structure and MS spectrum of a catechol -LIVAGK-NH$_2$ (SEQ ID NO 16 amidated) analog FIG. 15. Chemical structure and MS spectrum of DBCO -LIVAGK-NH$_2$ (SEQ ID NO 16 amidated)
Figure 14:
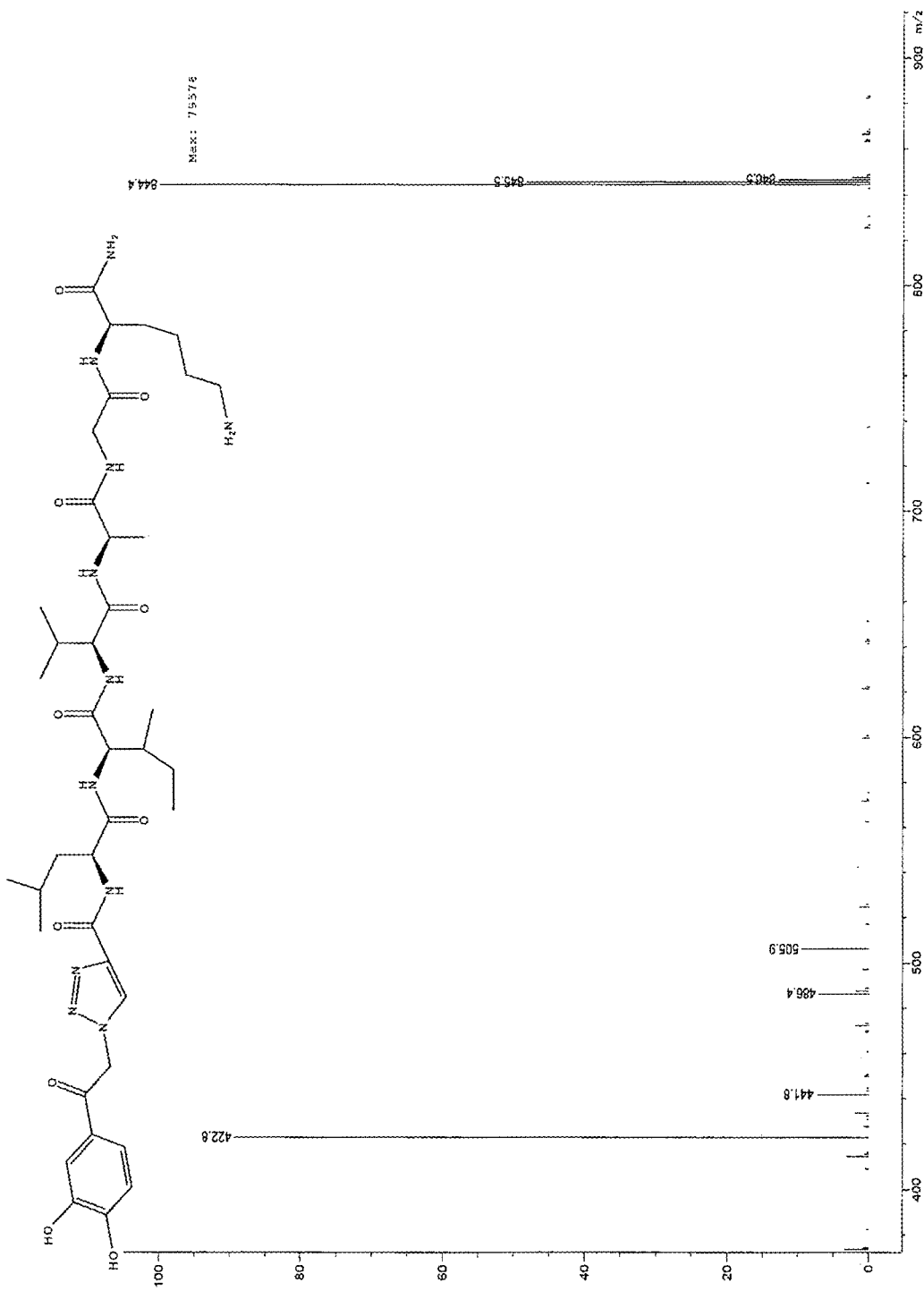

Click Reaction Between 2-azido-3' 4'-dihydroxyacetophenone and N-propiolyl-Peptides General Procedure:

An equimolar amount of peptide and metal compound was suspended in a 1:1 mixture of MilliQ water and tBuOH. To increase the solubility about 10% DMF was added. Subsequently 10 mol % of sodium ascorbate dissolved in a minimum of water was added followed by 1 mol % CuSO4.5H2O dissolved water. The resulting solution was allowed to react overnight and the presence of the catechol peptide conjugate was confirmed by HPLC-MS (see FIGS. 13 and 14)

Exemplary embodiments of the invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A hydrogel comprising a first peptide having the general formula $$B^*\text{-}Z_p\text{-}(X)_m\text{-}(Y)_n\text{-}Z'_q \text{ or } Z_p\text{-}(X)_m\text{-}(Y)_n\text{-}Z'_q\text{-}B^* \text{ or } B^*\text{-}Z_p\text{-}(X)_m\text{-}(Y)_n\text{-}Z'_q\text{-}B^*$$

wherein
B* is a bioactive agent comprising anti-cancer therapeutic;
X is, at each occurrence, independently selected from an aliphatic amino acid, an aliphatic amino acid derivative and a glycine;
Y is, at each occurrence, independently selected from a polar amino acid and a polar amino acid derivative;
Z is an N-terminal protecting group;
Z' is a C-terminal protecting group;
m is an integer selected from 2 to 6;
n is selected from 1 or 2; and
p and q are independently selected from 0 or 1,
wherein said hydrogel further comprises a second peptide having the general formula $$Z\text{-}(X)_m\text{-}(Y)_n\text{-}Z'_q,$$

wherein said bioactive agent is covalently linked to the N-terminus and/or the C-terminus of said first peptide by means of a click chemistry reaction and the release of the bioactive agent is triggered via hydrolysis of the hydrogel, and wherein the covalent attachment of the bioactive agent to the first peptide and the release of the bioactive agent via hydrolysis are capable of achieving sustained or controlled release delivery of said bioactive agent wherein said second peptide is used as a matrix, and wherein the hydrogel comprises 10 wt % of the first peptide and 90 wt % of the second peptide.

2. The hydrogel of claim 1, wherein said first peptide has the general formula $$B^*\text{-}(X)_m\text{-}(Y)_n\text{-}Z'_q.$$

3. The hydrogel of claim 1, wherein said anti-cancer therapeutic is selected from the group consisting of nucleic acids, DNA, RNA, small RNAs, miRNA, mRNA, siRNA, rRNA, snRNA, snoRNA and analogs thereof, (poly)peptides, peptidomimetics, neutral or anionic or cationic polymers, virus particles, (poly)saccharides, oligosaccharides, glycans, vitamins, hormones, steroids, growth factors, sialic acids, antigens, antibodies, anti-inflammatory molecules, vaccines, drugs, prodrugs, catechols, biotin, lipids and lipid analogs, antibodies, nanoparticles, organometallic compounds and other organic or inorganic compounds, complexes, composites and nanomaterials.

4. The hydrogel of claim 1, wherein said anti-cancer therapeutic is selected from the group consisting of oxaliplatin, cisplatin, carboplatin, doxorubicin, daunorubicin, clyclophosphamide, 5-fluorouracile, chlorambucil, vincristine, methotrexate, hydroxyurea, bleomecyn, topotecan, irinotecan, dactinomycin, docetaxel, vinblastine, paclitaxel, imatinib, herceptin and other monoclonal or polyclonal antibodies.

5. The hydrogel of claim 1, wherein said bioactive agent is covalently linked to the N-terminus and/or the C-terminus of said first peptide via a linking group comprising a moiety selected from the group consisting of a triazole group, a cyclohexene group, a thioether group, a succinimide group, an isoxazole group and analogs thereof, a isoxazolidine group and analogs thereof, and a pyrazoline group.

6. The hydrogel of claim 1, wherein said click chemistry reaction is a [3+2] cycloaddition reaction, a Diels-Alder reaction, a thiol-ene reaction, a thiol-Michael addition reaction, a thiol-vinylsulfone reaction, a Staudinger reaction.

7. The hydrogel of claim 1, wherein the hydrophobicity decreases from the N-terminus to the C-terminus of said peptide.

8. The hydrogel of claim 1, wherein said aliphatic amino acid and aliphatic amino acid derivative are selected from the group consisting of alanine (Ala, A), homoallylglycine, homopropargylglycine, isoleucine (Ile, I), norleucine, leucine (Leu, L) and valine (Val, V).

9. The hydrogel of claim 1, wherein said polar amino acid and polar amino acid derivative are selected from the group consisting of aspartic acid (Asp, D), asparagine (Asn, N), glutamic acid (Glu, E), glutamine (Gln, Q), 5-N-ethyl-glutamine (theanine), citrulline, thio-citrulline, cysteine (Cys, C), homocysteine, methionine (Met, M), ethionine, selenomethionine, telluromethionine, serine (Ser, S), homoserine, arginine (Arg, R), homoarginine, threonine (Thr, T), allo-threonine, lysine (Lys, K), hydroxylysine, N(6)-carboxymethyllysine, ornithine (Orn), 2,4-diaminobutyric acid (Dab), 2,4-diaminopropionic acid (Dap), histidine (His, H), azido-alanine, azido-homoalanine, azido-ornithine and azido-lysine.

10. The hydrogel of claim 1, wherein m is selected from 2 to 5.

11. The hydrogel of claim 1, wherein m+n is <7 or m+n is <6.

12. The hydrogel of claim 1, wherein $(X)_m\text{-}(Y)_n$ is selected from the group consisting of

| | |
|---|---|
| SEQ ID NO: 1 | LIVAGDD |
| SEQ ID NO: 2 | LIVAGDE |
| SEQ ID NO: 3 | LIVAGED |
| SEQ ID NO: 4 | LIVAGEE |
| SEQ ID NO: 5 | LIVAGKC |
| SEQ ID NO: 6 | LIVAGSC |
| SEQ ID NO: 7 | AIVAGKC |
| SEQ ID NO: 8 | AIVAGSC |
| SEQ ID NO: 9 | LIVAGC |
| SEQ ID NO: 10 | LIVAGD |
| SEQ ID NO: 11 | ILVAGD |
| SEQ ID NO: 12 | LIVAAD |
| SEQ ID NO: 13 | LAVAGD |
| SEQ ID NO: 14 | AIVAGD |
| SEQ ID NO: 15 | LIVAGE |
| SEQ ID NO: 16 | LIVAGK |
| SEQ ID NO: 17 | LIVAGS |
| SEQ ID NO: 18 | ILVAGS |
| SEQ ID NO: 19 | AIVAGS |
| SEQ ID NO: 20 | LIVAGT |
| SEQ ID NO: 21 | AIVAGT |
| SEQ ID NO: 22 | LIVAD |
| SEQ ID NO: 23 | LIVGD |
| SEQ ID NO: 24 | IVAD |
| SEQ ID NO: 25 | IIID |
| SEQ ID NO: 26 | IIIK |
| SEQ ID NO: 43 | IVD |
| SEQ ID NO: 44 | IID |
| SEQ ID NO: 45 | LVE |
| SEQ ID NO: 46 | IVE |
| SEQ ID NO: 47 | LVD |
| SEQ ID NO: 48 | VIE |
| SEQ ID NO: 49 | VID |
| SEQ ID NO: 50 | VLD |
| SEQ ID NO: 51 | VLE |
| SEQ ID NO: 52 | LLE |
| SEQ ID NO: 53 | LLD |
| SEQ ID NO: 54 | IIE |
| SEQ ID NO: 55 | IVK |
| SEQ ID NO: 56 | IV(Orn) |
| SEQ ID NO: 57 | IV(Dab) |
| SEQ ID NO: 58 | IV(Dap) |
| SEQ ID NO: 59 | IVS |
| SEQ ID NO: 60 | LVS |
| SEQ ID NO: 61 | LVK |
| SEQ ID NO: 62 | LV(Orn) |
| SEQ ID NO: 63 | LV(Dab) |
| SEQ ID NO: 64 | LV(Dap) |
| SEQ ID NO: 27 | ILVAGK |
| SEQ ID NO: 28 | ILVAG(Orn) |
| SEQ ID NO: 29 | ILVAG(Dab) |
| SEQ ID NO: 30 | ILVAG(Dap) |
| SEQ ID NO: 31 | ILVAGS |
| SEQ ID NO: 32 | ILVAGKC |

AIVAGK                      SEQ ID NO: 33

AIVAG(Orn)                  SEQ ID NO: 34

AIVAG(Dab)                  SEQ ID NO: 35

AIVAG(Dap)                  SEQ ID NO: 36

LIVAG(Orn)                  SEQ ID NO: 37

LIVAG(Dab)                  SEQ ID NO: 38

LIVAG(Dap)                  SEQ ID NO: 39

III(Orn)                    SEQ ID NO: 40

III(Dab)                    SEQ ID NO: 41
and

III(Dap).                   SEQ ID NO: 42

13. The hydrogel of claim 1, wherein said N-terminal protecting group is an acetyl group.

14. The hydrogel of claim 1, wherein said N-terminal protecting group is a peptidomimetic molecule, including natural and synthetic amino acid derivatives, wherein the N-terminus of said peptidomimetic molecule may be modified with a functional group selected from the group consisting of carboxylic acid, amide, alcohol, aldehyde, amine, imine, nitrile, an urea analog, thiol, phosphate, carbonate, sulfate, nitrate, maleimide, vinyl sulfone, azide, alkyne, alkene, carbohydrate, imide, peroxide, ester, thioester, aryl, ketone, sulphite, nitrite, phosphonate and silane.

15. The hydrogel of claim 1, wherein the C-terminal protecting group is an amide group comprising the formula —CONHR or —CONRR', with R and R' being selected from the group consisting of H, unsubstituted or substituted alkyls, and unsubstituted or substituted aryls.

16. The hydrogel of claim 1, wherein the C-terminal protecting group is an ester group comprising the formula —CO$_2$R, with R being selected from the group consisting of H, unsubstituted or substituted alkyls, and unsubstituted or substituted aryls.

17. The hydrogel of claim 1, wherein said C-terminal protecting group is a peptidomimetic molecule, including natural and synthetic amino acid derivatives, wherein the C-terminus of said peptidomimetic molecule may be modified with a functional group selected from the group consisting of carboxylic acid, amide, alcohol, aldehyde, amine, imine, nitrile, an urea analog, thiol, phosphate, carbonate, sulfate, nitrate, maleimide, vinyl sulfone, azide, alkyne, alkene, carbohydrate, imide, peroxide, ester, thioester, aryl, ketone, sulphite, nitrite, phosphonate and silane.

18. The hydrogel of claim 1, wherein said second peptide is capable of forming said hydrogel via self-assembly.

19. The hydrogel of claim 1, wherein said first peptide is capable of forming said hydrogel via self-assembly.

20. The hydrogel of claim 1, wherein the hydrogel is characterized by a storage modulus G' to loss modulus G" ratio that is greater than 2.

21. The hydrogel of claim 1, wherein the hydrogel is characterized by a storage modulus G' in the range of from 100 Pa to 100,000 Pa at a frequency in the range of from 0.001 Hz to 16 Hz.

22. The hydrogel of claim 1, wherein the hydrogel is injectable and gels in situ.

23. A device for drug delivery comprising a hydrogel of claim 1.

24. An implant comprising a hydrogel of claim 1.

25. A pharmaceutical or cosmetic composition comprising a hydrogel of claim 1.

26. A kit comprising a first container with a first peptide as defined in claim 1 and a second container with an aqueous solution, wherein said first container further contains a second peptide as defined in claim 1, or wherein said kit further comprises a third container with a second peptide as defined in claim 1.

27. The hydrogel according to claim 1, wherein p is 0.

28. The hydrogel according to claim 6, wherein said click chemistry reaction further comprises 1,3-dipolar cycloaddition reaction.

29. The hydrogel according to claim 28, wherein said 1,3-dipolar cycloaddition reaction is selected from the group comprising Cu(I)-catalyzed 1,3-dipolar cycloaddition reaction and strained promoted 1,3-dipolar cycloaddition reaction.

30. The hydrogel according claim 18, wherein the self-assembly is an antiparallel self-assembly.

31. The hydrogel according to claim 19, wherein the self-assembly is an antiparallel self-assembly.

32. The hydrogel according to claim 21, wherein the frequency is in the range of from 0.01 Hz to 0.2 Hz.

33. The hydrogel according to claim 23, wherein the drug delivery is sustained or controlled release drug delivery.

* * * * *

UNITED STATES PATENT AND TRADEMARK OFFICE
CERTIFICATE OF CORRECTION

PATENT NO. : 10,117,946 B2  
APPLICATION NO. : 14/655223  
DATED : November 6, 2018  
INVENTOR(S) : Michael Reithofer et al.

Page 1 of 2

It is certified that error appears in the above-identified patent and that said Letters Patent is hereby corrected as shown below:

Column 72, Line 66 to Column 75, Line 26 (Claim 12) should read:

12. The hydrogel of claim 1, wherein $(X)_m\text{-}(Y)_n$ is selected from the group consisting of

| | |
|---|---|
| LIVAGDD | SEQ ID NO: 1 |
| LIVAGDE | SEQ ID NO: 2 |
| LIVAGED | SEQ ID NO: 3 |
| LIVAGEE | SEQ ID NO: 4 |
| LIVAGKC | SEQ ID NO: 5 |
| LIVAGSC | SEQ ID NO: 6 |
| AIVAGKC | SEQ ID NO: 7 |
| AIVAGSC | SEQ ID NO: 8 |
| LIVAGC | SEQ ID NO: 9 |
| LIVAGD | SEQ ID NO: 10 |
| ILVAGD | SEQ ID NO: 11 |
| LIVAAD | SEQ ID NO: 12 |
| LAVAGD | SEQ ID NO: 13 |
| AIVAGD | SEQ ID NO: 14 |
| LIVAGE | SEQ ID NO: 15 |
| LIVAGK | SEQ ID NO: 16 |
| LIVAGS | SEQ ID NO: 17 |
| ILVAGS | SEQ ID NO: 18 |
| AIVAGS | SEQ ID NO: 19 |
| LIVAGT | SEQ ID NO: 20 |
| AIVAGT | SEQ ID NO: 21 |

Signed and Sealed this  
Nineteenth Day of March, 2019

Andrei Iancu  
*Director of the United States Patent and Trademark Office*

| | |
|---|---|
| LIVAD | SEQ ID NO: 22 |
| LIVGD | SEQ ID NO: 23 |
| IVAD | SEQ ID NO: 24 |
| IIID | SEQ ID NO: 25 |
| IIIK | SEQ ID NO: 26 |
| IVD | SEQ ID NO: 58 |
| IID | SEQ ID NO: 59 |
| LVE | SEQ ID NO: 60 |
| IVE | SEQ ID NO: 61 |
| LVD | SEQ ID NO: 62 |
| VIE | SEQ ID NO: 63 |
| VID | SEQ ID NO: 64 |
| VLD | SEQ ID NO: 65 |
| VLE | SEQ ID NO: 66 |
| LLE | SEQ ID NO: 67 |
| LLD | SEQ ID NO: 68 |
| IIE | SEQ ID NO: 69 |
| IVK | SEQ ID NO: 70 |
| IV(Orn) | SEQ ID NO: 71 |
| IV(Dab) | SEQ ID NO: 72 |
| IV(Dap) | SEQ ID NO: 73 |
| IVS | SEQ ID NO: 74 |
| LVS | SEQ ID NO: 75 |
| LVK | SEQ ID NO: 76 |
| LV(Orn) | SEQ ID NO: 77 |
| LV(Dab) | SEQ ID NO: 78 |
| LV(Dap) | SEQ ID NO: 79 |
| ILVAGK | SEQ ID NO: 27 |
| ILVAG(Orn) | SEQ ID NO: 28 |
| ILVAG(Dab) | SEQ ID NO: 29 |
| ILVAG(Dap) | SEQ ID NO: 30 |
| ILVAGS | SEQ ID NO: 31 |
| ILVAGKC | SEQ ID NO: 32 |
| AIVAGK | SEQ ID NO: 33 |
| AIVAG(Orn) | SEQ ID NO: 34 |
| AIVAG(Dab) | SEQ ID NO: 35 |
| AIVAG(Dap) | SEQ ID NO: 36 |
| LIVAG(Orn) | SEQ ID NO: 37 |
| LIVAG(Dab) | SEQ ID NO: 38 |
| LIVAG(Dap) | SEQ ID NO: 39 |
| III(Orn) | SEQ ID NO: 40 |
| III(Dab) | SEQ ID NO: 41 and |
| III(Dap) | SEQ ID NO: 42. |

SEQUENCE LISTING

```
<160> NUMBER OF SEQ ID NOS: 79

<210> SEQ ID NO 1
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 1

Leu Ile Val Ala Gly Asp Asp
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 2

Leu Ile Val Ala Gly Asp Glu
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 3

Leu Ile Val Ala Gly Glu Asp
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 4

Leu Ile Val Ala Gly Glu Glu
1               5
```

```
<210> SEQ ID NO 5
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 5

Leu Ile Val Ala Gly Lys Cys
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 6

Leu Ile Val Ala Gly Ser Cys
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 7

Ala Ile Val Ala Gly Lys Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 8

Ala Ile Val Ala Gly Ser Cys
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 9

Leu Ile Val Ala Gly Cys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 10

Leu Ile Val Ala Gly Asp
1               5

<210> SEQ ID NO 11
```

```
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 11

Ile Leu Val Ala Gly Asp
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 12

Leu Ile Val Ala Ala Asp
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 13

Leu Ala Val Ala Gly Asp
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 14

Ala Ile Val Ala Gly Asp
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 15

Leu Ile Val Ala Gly Glu
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 16

Leu Ile Val Ala Gly Lys
1               5

<210> SEQ ID NO 17
<211> LENGTH: 6
```

```
<212> TYPE: PRT
<213> ORGANISM: Artificial Sequence
<220> FEATURE:
<223> OTHER INFORMATION: Synthetic Polypeptide

<400> SEQUENCE: 17

Leu Ile Val Ala Gly Ser
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 18

Ile Leu Val Ala Gly Ser
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 19

Ala Ile Val Ala Gly Ser
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 20

Leu Ile Val Ala Gly Thr
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 21

Ala Ile Val Ala Gly Thr
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 22

Leu Ile Val Ala Asp
1               5

<210> SEQ ID NO 23
<211> LENGTH: 5
<212> TYPE: PRT
```

<213> ORGANISM: Artificial Sequence
<220> FEATURE:
<223> OTHER INFORMATION: Synthetic Polypeptide

<400> SEQUENCE: 23

Leu Ile Val Gly Asp
1               5

<210> SEQ ID NO 24
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 24

Ile Val Ala Asp
1

<210> SEQ ID NO 25
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 25

Ile Ile Ile Asp
1

<210> SEQ ID NO 26
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 26

Ile Ile Ile Lys
1

<210> SEQ ID NO 27
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 27

Ile Leu Val Ala Gly Lys
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Orn

<400> SEQUENCE: 28

Ile Leu Val Ala Gly Xaa
1               5

```
<210> SEQ ID NO 29
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (6)..(6)
<223> OTHER INFORMATION: Xaa is Dab

<400> SEQUENCE: 29

Ile Leu Val Ala Gly Xaa
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Dap

<400> SEQUENCE: 30

Ile Leu Val Ala Gly Xaa
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 31

Ile Leu Val Ala Gly Ser
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 32

Ile Leu Val Ala Gly Lys Cys
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 33

Ala Ile Val Ala Gly Lys
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: misc_feature
<222> LOCATION: (6)..(6)
<223> OTHER INFORMATION: Xaa is Orn

<400> SEQUENCE: 34

Ala Ile Val Ala Gly Xaa
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Dab

<400> SEQUENCE: 35

Ala Ile Val Ala Gly Xaa
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Dap

<400> SEQUENCE: 36

Ala Ile Val Ala Gly Xaa
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Orn

<400> SEQUENCE: 37

Leu Ile Val Ala Gly Xaa
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Dab

<400> SEQUENCE: 38

Leu Ile Val Ala Gly Xaa
1               5
```

```
<210> SEQ ID NO 39
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (6)..(6)
<223> OTHER INFORMATION: Xaa is Dap

<400> SEQUENCE: 39

Leu Ile Val Ala Gly Xaa
1               5

<210> SEQ ID NO 40
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa is Orn

<400> SEQUENCE: 40

Ile Ile Ile Xaa
1

<210> SEQ ID NO 41
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa is Dab

<400> SEQUENCE: 41

Ile Ile Ile Xaa
1

<210> SEQ ID NO 42
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa is Dap

<400> SEQUENCE: 42

Ile Ile Ile Xaa
1

<210> SEQ ID NO 43
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 43

Leu Ile Val Ala Gly
1               5
```

<210> SEQ ID NO 44
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 44

Ile Leu Val Ala Gly
1               5

<210> SEQ ID NO 45
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 45

Ile Leu Val Ala
1

<210> SEQ ID NO 46
<211> LENGTH: 4
<212> TYPE: PRT
<213> ORGANISM: Artificial Sequence
<220> FEATURE:
<223> OTHER INFORMATION: Synthetic Polynucleotide

<400> SEQUENCE: 46

Leu Ile Val Ala
1

<210> SEQ ID NO 47
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 47

Ile Val Ala Gly
1

<210> SEQ ID NO 48
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 48

Leu Val Ala Gly
1

<210> SEQ ID NO 49
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 49

Leu Ile Ala Gly
1

```
<210> SEQ ID NO 50
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 50

Leu Ile Val Gly
1

<210> SEQ ID NO 51
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 51

Ile Leu Ala Gly
1

<210> SEQ ID NO 52
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 52

Ile Leu Val Gly
1

<210> SEQ ID NO 53
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 53

Ala Ser Met Thr Gly Gly Gln Gln Met Gly
1               5                   10

<210> SEQ ID NO 54
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 54

Pro Glu Asp Pro Glu Asp
1               5

<210> SEQ ID NO 55
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 55

Glu Gln Lys Leu Ile Ser Glu Glu Asp Leu
1               5                   10
```

```
<210> SEQ ID NO 56
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 56

Tyr Pro Tyr Asp Val Pro Asp Tyr Ala
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 57

Leu Ile Val Ala Gly Lys Lys
1               5

<210> SEQ ID NO 58
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 58

Ile Val Asp
1

<210> SEQ ID NO 59
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 59

Ile Ile Asp
1

<210> SEQ ID NO 60
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 60

Leu Val Glu
1

<210> SEQ ID NO 61
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 61

Ile Val Glu
1

<210> SEQ ID NO 62
```

```
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 62

Leu Val Asp
1

<210> SEQ ID NO 63
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 63

Val Ile Glu
1

<210> SEQ ID NO 64
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 64

Val Ile Asp
1

<210> SEQ ID NO 65
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 65

Val Leu Asp
1

<210> SEQ ID NO 66
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 66

Val Leu Glu
1

<210> SEQ ID NO 67
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 67

Leu Leu Glu
1

<210> SEQ ID NO 68
<211> LENGTH: 3
```

```
<212> TYPE: PRT
<213> ORGANISM: Artificial Sequence
<220> FEATURE:
<223> OTHER INFORMATION: Synthetic Polypeptide

<400> SEQUENCE: 68

Leu Leu Asp
1

<210> SEQ ID NO 69
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 69

Ile Ile Glu
1

<210> SEQ ID NO 70
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 70

Ile Val Lys
1

<210> SEQ ID NO 71
<211> LENGTH: 3
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Orn

<400> SEQUENCE: 71

Ile Val Xaa
1

<210> SEQ ID NO 72
<211> LENGTH: 3
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Dab

<400> SEQUENCE: 72

Ile Val Xaa
1

<210> SEQ ID NO 73
<211> LENGTH: 3
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

```
<222> LOCATION: (3)..(3)
<223> OTHER INFORMATION: Xaa is Dap

<400> SEQUENCE: 73

Ile Val Xaa
1

<210> SEQ ID NO 74
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 74

Ile Val Ser
1

<210> SEQ ID NO 75
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 75

Leu Val Ser
1

<210> SEQ ID NO 76
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 76

Leu Val Lys
1

<210> SEQ ID NO 77
<211> LENGTH: 3
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Orn

<400> SEQUENCE: 77

Leu Val Xaa
1

<210> SEQ ID NO 78
<211> LENGTH: 3
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Dab

<400> SEQUENCE: 78

Leu Val Xaa
```

```
1

<210> SEQ ID NO 79
<211> LENGTH: 3
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (3)..(3)
<223> OTHER INFORMATION: Xaa is Dap

<400> SEQUENCE: 79

Leu Val Xaa
1
```